(12) United States Patent
Epstein et al.

(10) Patent No.: US 8,962,859 B2
(45) Date of Patent: Feb. 24, 2015

(54) SPIRO-AMINO-IMIDAZO-FUSED HETEROCYCLIC COMPOUNDS AS BETA-SECRETASE MODULATORS AND METHODS OF USE

(75) Inventors: Oleg Epstein, Belmont, MA (US); Ryan White, Somerville, MA (US); Vinod F. Patel, Acton, MA (US); Jason Brooks Human, Boston, MA (US)

(73) Assignee: Amgen Inc., Thousand Oaks, CA (US)

( * ) Notice: Subject to any disclaimer, the term of this patent is extended or adjusted under 35 U.S.C. 154(b) by 0 days.

(21) Appl. No.: 13/982,096

(22) PCT Filed: Feb. 13, 2012

(86) PCT No.: PCT/US2012/024918
§ 371 (c)(1),
(2), (4) Date: Oct. 22, 2013

(87) PCT Pub. No.: WO2012/112462
PCT Pub. Date: Aug. 23, 2012

(65) Prior Publication Data
US 2014/0038954 A1 Feb. 6, 2014

Related U.S. Application Data

(60) Provisional application No. 61/443,192, filed on Feb. 15, 2011.

(51) Int. Cl.
| | | |
|---|---|---|
| C07D 487/10 | (2006.01) | |
| C07D 313/00 | (2006.01) | |
| C07D 491/20 | (2006.01) | |
| A61K 31/353 | (2006.01) | |

(52) U.S. Cl.
CPC ............ *C07D 491/20* (2013.01); *A61K 31/353* (2013.01)
USPC ...................................... 548/301.1; 549/344

(58) Field of Classification Search
CPC .................................................. C07D 487/10
USPC ...................................... 548/301.1; 549/344
See application file for complete search history.

(56) References Cited

U.S. PATENT DOCUMENTS

| | | | |
|---|---|---|---|
| 5,441,870 A | 8/1995 | Seubert et al. | |
| 5,712,130 A | 1/1998 | Hajko et al. | |
| 5,942,400 A | 8/1999 | Anderson | |
| 8,426,447 B2 * | 4/2013 | White et al. | ............... 514/336 |
| 2005/0282825 A1 | 12/2005 | Malamas et al. | |
| 2006/0111370 A1 | 5/2006 | Zhu et al. | |
| 2007/0004786 A1 | 1/2007 | Malamas et al. | |
| 2007/0027199 A1 | 2/2007 | Malamas et al. | |
| 2007/0072925 A1 | 3/2007 | Malamas et al. | |
| 2007/0203116 A1 | 8/2007 | Quagliato et al. | |
| 2007/0287692 A1 | 12/2007 | Wu et al. | |
| 2008/0200445 A1 | 8/2008 | Zhu et al. | |

FOREIGN PATENT DOCUMENTS

| | | |
|---|---|---|
| EP | 01942105 A1 | 7/2008 |
| WO | 00/17369 A2 | 3/2000 |
| WO | 2005/058311 A1 | 6/2005 |
| WO | 2005/097767 A1 | 10/2005 |
| WO | 2006/009655 A1 | 1/2006 |
| WO | 2006009655 A1 | 1/2006 |
| WO | 2006/041404 A1 | 4/2006 |
| WO | 2006/076284 A2 | 7/2006 |
| WO | 2006/083760 A1 | 8/2006 |
| WO | 2006/138230 A3 | 12/2006 |
| WO | 2006/138265 A1 | 12/2006 |

(Continued)

OTHER PUBLICATIONS

Joachim et al., *Alz. Dis. Assoc. Dis.*, 6:7-34 (1992).
Selkoe, *Neuron*, 6:487 (1991).
Seubert et al., *Nature*, 359:325-327 (1992).
Citron, *Trends in Pharmacological Sciences*, 25(2):92-97 (2004).
Shankar, G.M., *Nature Medicine* (Jun. 22, 2008) online doi 10:1038 nm 1782.
Sinha et al., *Nature*, 402:537-554 (1999) (p. 510).
Sabbagh, M. et al., *Alz. Dis. Rev.* 3:1-19 (1997).
Cole, S.L., Vasser, R., *Molecular Degeneration* 2:22, 2007.
Luo et al., *Nature Neuroscience*, 4:231-232 (2001).
*Expert Opin. Pharmacother.* (2009), 10 (10).
*Clin. Neuropharmacol.* 2007; 30 (pp. 317-325).
*Neurology*, 2006, 66 (pp. 602-624).
Berge et al., *J. Pharm. Sci.*, 66:1 (1977).
*J. Neurosci.*, Nov. 16, 2011:31(46):16507-16516.
*Neuron* 68, 428-441, Nov. 4, 2010.

*Primary Examiner* — Nizal Chandrakumar
(74) *Attorney, Agent, or Firm* — G. Prabhakar Reddy

(57) ABSTRACT

The present invention provides a new class of compounds useful for the modulation of beta-secretase enzyme (BACE) activity. The compounds have a general Formula I:

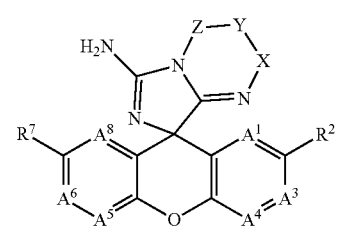

wherein variables $A^1$, $A^3$, $A^5$, $A^6$, $A^8$, $R^2$, $R^7$, X, Y and Z of Formula I are defined herein. The invention also provides pharmaceutical compositions comprising the compounds, and corresponding uses of the compounds and compositions for treatment of disorders and/or conditions related to plaque formation and deposition, resulting from the activity of BACE. Such BACE mediated disorders include, for example, Alzheimer's Disease, cognitive deficits and impairments, schizophrenia and other central nervous system conditions and disorders. The invention further provides compounds of Formulas II and III, and of sub-formulas of Formulas I, II and III, intermediates and processes and methods useful for the preparation of compounds of Formulas I-III.

12 Claims, No Drawings

(56) References Cited

FOREIGN PATENT DOCUMENTS

| | | |
|---|---|---|
| WO | 2007/011810 A1 | 1/2007 |
| WO | 2007/011833 A2 | 1/2007 |
| WO | 2007/038271 A1 | 4/2007 |
| WO | 2007/049532 A1 | 5/2007 |
| WO | 2007/058602 A2 | 5/2007 |
| WO | 2007/100536 A1 | 7/2007 |
| WO | 2007/114771 A1 | 10/2007 |
| WO | 2008/054698 A2 | 5/2008 |
| WO | 2008/076045 A1 | 6/2008 |
| WO | 2008/076046 A1 | 6/2008 |
| WO | 2008/092785 A1 | 8/2008 |
| WO | 2008/103351 A3 | 8/2008 |
| WO | 2008/108378 A2 | 9/2008 |
| WO | 2008/118379 A2 | 10/2008 |
| WO | 2008/133273 A1 | 11/2008 |
| WO | 2008/133274 A1 | 11/2008 |
| WO | 2008/150217 A1 | 12/2008 |
| WO | 2009/091016 A1 | 1/2009 |
| WO | 2009/134617 A1 | 4/2009 |
| WO | 2010/021680 A2 | 2/2010 |
| WO | 2010/105179 A2 | 9/2010 |
| WO | 2010/128058 A1 | 11/2010 |
| WO | 2011123674 A1 | 10/2011 |
| WO | 2011130741 A1 | 10/2011 |
| WO | 2012019056 A1 | 2/2012 |
| WO | 2010030954 A1 | 3/2012 |
| WO | 2012040641 A1 | 3/2012 |

* cited by examiner

SPIRO-AMINO-IMIDAZO-FUSED HETEROCYCLIC COMPOUNDS AS BETA-SECRETASE MODULATORS AND METHODS OF USE

RELATED APPLICATIONS

This application is a US national stage application under 35 U.S.C. §371 of International Application No. PCT/US2012/024918, having an international filing date of Feb. 13, 2012, which claims the benefit of, and priority to, U.S. Provisional Application No. 61/443,192, filed on Feb. 15, 2011, each specification of which is hereby incorporated herein by reference in its entirety.

FIELD OF THE INVENTION

The invention relates generally to pharmaceutically active compounds, pharmaceutical compositions and methods of use thereof, to treat beta-secretase mediated diseases and conditions, including, without limitation, Alzheimer's disease, plaque formation and related central nervous system (CNS) disorders.

BACKGROUND OF THE INVENTION

Alzheimer's disease (AD) affects greater than 12 million aging people worldwide, and importantly, the number affected continues to grow. AD accounts for the majority of dementia clinically diagnosed after the age of 60. AD is generally characterized by the progressive decline of memory, reasoning, judgement and orientation. As the disease progresses, motor, sensory, and vocal abilities are affected until there is global impairment of multiple cognitive functions. The loss of cognitive function occurs gradually, typically leading to a diminished cognition of self, family and friends. Patients with severe cognitive impairment and/or diagnosed as end-stage AD are generally bedridden, incontinent, and dependent on custodial care. The AD patient eventually dies in about nine to ten years, on average, after initial diagnosis. Due to the incapacitating, generally humiliating and ultimately fatal effects of AD, there is a need to effectively treat AD upon diagnosis.

AD is characterized by two major physiological changes in the brain. The first change, beta amyloid plaque formation, supports the "amyloid cascade hypothesis" which conveys the thought that AD is caused by the formation of characteristic beta amyloid peptide (A-beta), or A-beta fragments thereof, deposits in the brain (commonly referred to as beta amyloid "plaques" or "plaque deposits") and in cerebral blood vessels (beta amyloid angiopathy). A wealth of evidence suggests that beta-amyloid and accompanying amyloid plaque formation is central to the pathophysiology of AD and is likely to play an early role in this intractable neurodegenerative disorder. The second change in AD is the formation of intraneuronal tangles, consisting of an aggregate form of the protein tau. Besides being found in patients with AD, intraneuronal tangles are also found in other dementia-inducing disorders. Joachim et al., *Alz. Dis. Assoc. Dis.*, 6:7-34 (1992).

Several lines of evidence indicate that progressive cerebral deposition of A-beta plays a seminal role in the pathogenisis of AD and can precede cognitive symptoms by years or even decades. Selkoe, *Neuron*, 6:487 (1991). Release of A-beta from neuronal cells grown in culture and the presence of A-beta in cerebrospinal fluid (CSF) of both normal individuals and AD patients has been demonstrated. Seubert et al., *Nature*, 359:325-327 (1992). Autopsies of AD patients have revealed large numbers of lesions comprising these 2 factors in areas of the human brain believed to be important for memory and cognition.

Smaller numbers of these lesions in a more restricted anatomical distribution are found in the brains of most aged humans who do not have clinical AD. Amyloid containing plaques and vascular amyloid angiopathy were also found in the brains of individuals with Down's Syndrome, Hereditary Cerebral Hemorrhage with Amyloidosis of the Dutch-type (HCHWA-D), and other neurodegenerative disorders.

It has been hypothesized that A-beta formation is a causative precursor or factor in the development of AD. More specifically, deposition of A-beta in areas of the brain responsible for cognitive factors is believed to be a major factor in the development of AD. Beta amyloid plaques are primarily composed of amyloid beta peptide (A-beta peptide). A-beta peptide is derived from the proteolytic cleavage of a large transmembrane amyloid precursor protein (APP), and is a peptide ranging in about 39-42 amino acid residues. A-beta 42 (42 amino acids long) is thought to be the major component of these plaque deposits in the brains of Alzheimer's Disease patients. Citron, *Trends in Pharmacological Sciences*, 25(2):92-97 (2004).

Similar plaques appear in some variants of Lewy body dementia and in inclusion body myositis, a muscle disease. Aβ also forms aggregates coating cerebral blood vessels in cerebral amyloid angiopathy. These plaques are composed of a tangle of regularly ordered fibrillar aggregates called amyloid fibers, a protein fold shared by other peptides such as prions associated with protein misfolding diseases. Research on laboratory rats suggest that the two-molecule, soluble form of the peptide is a causative agent in the development of Alzheimer's and that the two-molecule form is the smallest synaptotoxic species of soluble amyloid beta oligomer. Shankar, G. M., *Nature Medicine* (Jun. 22, 2008) online doi 10:1038 nm 1782.

Several aspartyl proteases, including beta-secretase and gamma-secretase, are thought to be involved in the processing or cleavage of APP, resulting in the formation of A-beta peptide. Beta secretase (BACE, also commonly referred to as memapsin) is thought to first cleave APP to generate two fragments: (1) a first N-terminus fragment (beta APP) and (2) a second C-99 fragment, which is subsequently cleaved by gamma secretase to generate the A-beta peptide. APP has also found to be cleaved by alpha-secretase to produce alpha-sAPP, a secreted form of APP that does not result in beta-amyloid plaque formation. This alternate pathway precludes the formation of A-beta peptide. A description of the proteolytic processing fragments of APP is found, for example, in U.S. Pat. Nos. 5,441,870, 5,712,130 and 5,942,400.

BACE is an aspartyl protease enzyme comprising 501 amino acids and responsible for processing APP at the beta-secretase specific cleavage site. BACE is present in two forms, BACE 1 and BACE 2, designated as such depending upon the specific cleavage site of APP. Beta secretase is described in Sinha et al., *Nature*, 402:537-554 (1999) (p510) and PCT application WO 2000/17369. It has been proposed that A-beta peptide accumulates as a result of APP processing by BACE. Moreover, in vivo processing of APP at the beta secretase cleavage site is thought to be a rate-limiting step in A-beta production. Sabbagh, M. et al., *Alz. Dis. Rev.* 3:1-19 (1997). Thus, inhibition of the BACE enzyme activity is desirable for the treatment of AD.

Studies have shown that the inhibition of BACE may be linked to the treatment of AD. The BACE enzyme is essential for the generation of beta-amyloid or A-beta. BACE knockout mice do not produce beta-amyloid and are free from Alzheimer's associated pathologies including neuronal loss and certain memory deficits. Cole, S. L., Vasser, R., *Molecular Degeneration* 2:22, 2007. When crossed with transgenic mice that over express APP, the progeny of BACE deficient mice show reduced amounts of A-beta in brain extracts as compares with control animals (Luo et al., *Nature Neuroscience*, 4:231-232 (2001)). The fact that BACE initiates the formation of beta-amyloid, and the observation that BACE levels are elevated in this disease provide direct and compelling reasons to develop therapies directed at BACE inhibition thus reducing beta-amyloid and its associated toxicities. To this end, inhibition of beta secretase activity and a corresponding reduction of A-beta in the brain should provide a therapeutic method for treating AD and other beta amyloid or plaque related disorders.

Consequently, the approach of regulating or reducing the formation of A-beta peptide formation and deposition as a potential treatment for AD has received tremendous attention and belief from both researchers and investors alike. A small molecule gamma-secretase inhibitor, LY450139 ("Semagacestat"), an A-beta lowering agent, is in phase II and Phase III clinical trials for the treatment of Alzheimer's Disease. The pharmacokinetics of semagacestat in plasma, as well as the plasma and cerebral spinal fluid (CSF) A-Beta peptide levels as pharmacodynamic responses to semagacestat administration were evaluated in healthy human subjects in single and multiple doses, and pharmacokinetic and pharmacodynamic changes were also assessed in mild to moderate AD patients in two (2) clinical trials (*Expert Opin. Pharmacother.* (2009), 10 (10); *Clin. Neuropharmacol.* 2007; 30 (pgs 317-325); and *Neurology,* 2006, 66 (pgs 602-624)).

Additional approaches have been taken in attempts to treat AD and plaque-related disorders. One such approach to reduce the formation of plaque on the brain involves the inhibition of and, therefore, the reduction of BACE activity. For example, each of the following PCT publications: WO 07/058602, WO 10/021680, WO 10/105179, WO 06/041404, WO 07/114771, WO 08/076045, WO 08/076046, WO 08/150217, WO 07/038271, WO 09/091016, WO 08/108378, WO 09/134617, WO 05/097767, WO 08/092785, WO 06/138265, WO 08/103351, WO 06/138230, WO 08/200445, WO 06/111370, WO 07/287692, WO 05/058311, EP 01942105, WO 08/133273, WO 08/133274, WO 07/049532, US20070027199, WO 07/038271, US20070072925, US20070203116, US20050282826, WO 08/118379, WO 06/076284, US20070004786, WO 06/083760, WO 07/011810, WO 07/011833, WO 08/054698 and WO10/128058, describe inhibitors of BACE, useful for treating AD and other beta-secretase mediated disorders.

Despite the many efforts and resources directed to researching A-beta lowering agents, there remains a need to identify safe and efficacious treatment agents for AD.

BRIEF DESCRIPTION OF THE INVENTION

The present invention provides a new class of compounds useful for the modulation of beta secretase activity, and as treatment of AD. Particularly, the compounds of the invention are useful for the regulation or reduction of the formation of A-beta peptide and, consequently, the regulation and/or reduction of formation of beta amyloid plaque both on the brain, as well as in the CNS. To this end, the compounds are useful for the treatment of AD and other beta secretase and/or plaque-related and/or mediated disorders. For example, the compounds are useful for the prophylaxis and/or treatment, acute and/or chronic, of AD and other diseases or conditions involving the deposition or accumulation of beta amyloid peptide, and formation of plaque, on the brain.

The compounds provided by the invention, including stereoisomers, tautomers, hydrates, solvates and pharmaceutically acceptable salts thereof, are generally defined by Formula I

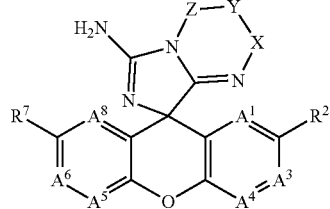

wherein each of $A^1$, $A^3$, $A^4$, $A^5$, $A^6$, $R^2$, $R^7$, X, Y and Z of Formula I are defined below. The invention also provides procedures for making compounds of Formula, and sub-Formulas thereof, as well as intermediates useful in such procedures.

The invention further provides pharmaceutical compositions comprising compounds of the invention, methods for the treatment of beta secretase mediated diseases using both the compounds and compositions of the invention. For example, and in one embodiment, the invention provides a pharmaceutical composition comprising an effective dosage amount of a compound of Formula I in association with at least one pharmaceutically acceptable excipient.

The foregoing merely summarizes certain aspects of the invention and is not intended, nor should it be construed, as limiting the invention in any way. All patents and other publications recited herein are hereby incorporated by reference in their entirety.

DETAILED DESCRIPTION OF THE INVENTION

In one embodiment of the invention, there are provided compounds, including stereoisomers, tautomers, hydrates, solvates and pharmaceutically acceptable salts thereof, which are generally defined by Formula I:

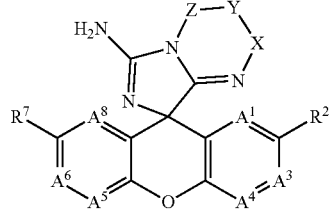

wherein
$A^1$ is $CR^1$ or N;
$A^3$ is $CR^3$ or N;
$A^4$ is $CR^4$ or N;
$A^5$ is $CR^5$ or N;
$A^6$ is $CR^6$ or N;
$A^8$ is $CR^8$ or N, provided that no more than one of $A^1$, $A^3$, $A^4$, $A^5$, $A^6$ and $A^8$ is N;
each of $R^1$, $R^4$, $R^5$ and $R^8$, independently, is H, F, Cl, Br, $CF_3$, $OCF_3$, $C_{1-6}$-alkyl, CN, OH, —$OC_{1-6}$-alkyl, —$S(O)_oC_{1-6}$-alkyl, —$NHC_{1-6}$-alkyl or —$C(O)C_{1-6}$-alkyl, wherein the $C_{1-6}$-alkyl and $C_{1-6}$-alkyl portion of —$OC_{1-6}$-alkyl, —$S(O)_oC_{1-6}$-alkyl, —$NHC_{1-6}$-alkyl and —$C(O)C_{1-6}$-alkyl are optionally substituted with 1-3 substituents of F, oxo or OH;

$R^2$ is Cl, Br, $C_{1-6}$-alkyl, $C_{2-4}$alkenyl, $C_{2-4}$alkynyl, CN, —$OC_{1-6}$alkyl, —$SC_{1-6}$alkyl, —$NHC_{1-6}$alkyl, —$N(C_{1-3}$alkyl$)_2$, —NH-phenyl, —NH-benzyl, phenyl, pyridyl, pyrimidyl, pyrazinyl, pyridazinyl, pyrazolyl, isoxazolyl, thiazolyl, pyranyl, dihydropyranyl, tetrahydropyranyl, furanyl, dihydrofuranyl, tetrahydrofuranyl, pyrrolyl, pyrrolidinyl, tetrahydropyrrolyl, piperidinyl, piperazinyl, morpholinyl, azetidinyl, 8-oxo-3-aza-bicyclo[3.2.1]oct-3-yl, aza-bicyclo[2.2.1]hept-5-yl, 2-oxo-7-aza-[3,5]-spironon-7-yl, cyclopentyl, cyclohexyl or —$Si(CH_3)_3$, wherein the $C_{1-6}$-alkyl, $C_{2-4}$alkenyl, $C_{2-4}$alkynyl, —$OC_{1-6}$alkyl, —$SC_{1-6}$alkyl, —$NHC_{1-6}$alkyl, —$N(C_{1-3}$alkyl$)_2$, —NH-phenyl, —NH-benzyl, phenyl, pyridyl, pyrimidyl, pyrazinyl, pyridazinyl, pyrazolyl, isoxazolyl, thiazolyl, pyranyl, dihydropyranyl, tetrahydropyranyl, furanyl, dihydrofuranyl, tetrahydrofuranyl, -pyrrolidinyl, piperidinyl, piperazinyl, morpholinyl, azetidinyl, 8-oxo-3-aza-bicyclo[3.2.1]oct-3-yl, aza-bicyclo[2.2.1]hept-5-yl, 2-oxo-7-aza-[3,5]-spironon-7-yl, cyclopentyl and cyclohexyl are optionally substituted, independently, with 1-5 substituents of $R^9$;

each of $R^3$ and $R^6$, independently, is H, halo, haloalkyl, haloalkoxyl, $C_{1-6}$-alkyl, CN, OH, $OC_{1-6}$-alkyl, $S(O)_oC_{1-6}$-alkyl, $NHC_{1-6}$-alkyl or $C(O)C_{1-6}$-alkyl;

$R^7$ is $C_{1-6}$-alkyl, $C_{2-4}$alkenyl, $C_{2-4}$alkynyl, CN, —$OC_{1-6}$alkyl, —$SC_{1-6}$alkyl, —$NHC_{1-6}$alkyl, —$N(C_{1-3}$alkyl$)_2$, —NHC(=O)$R^9$, —C(=O)NH$R^9$, —NHS(O)$_2R^9$, —S(O)$_2$NH$R^9$, —NH-phenyl, —NH-benzyl, phenyl, pyridyl, pyrimidyl, pyrazinyl, pyridazinyl, pyrazolyl, isoxazolyl, thiazolyl, pyranyl, dihydropyranyl, tetrahydropyranyl, furanyl, dihydrofuranyl, tetrahydrofuranyl, pyrrolyl, pyrrolidinyl, tetrahydropyrrolyl, piperidinyl, piperazinyl, morpholinyl, azetidinyl, 8-oxo-3-aza-bicyclo[3.2.1]oct-3-yl, aza-bicyclo[2.2.1]hept-5-yl, 2-oxo-7-aza-[3,5]-spironon-7-yl, cyclopentyl or cyclohexyl, wherein the $C_{1-6}$-alkyl, $C_{2-4}$alkenyl, $C_{2-4}$alkynyl, —$OC_{1-6}$alkyl, —$SC_{1-6}$alkyl, —$NHC_{1-6}$alkyl, —$N(C_{1-3}$alkyl$)_2$, —NHC(=O)$R^9$, —C(=O)NH$R^9$, —NHS(O)$_2R^9$, —S(O)$_2$NH$R^9$, —NH-phenyl, —NH-benzyl, phenyl, pyridyl, pyrimidyl, pyrazinyl, pyridazinyl, pyrazolyl, isoxazolyl, thiazolyl, pyranyl, dihydropyranyl, tetrahydropyranyl, furanyl, dihydrofuranyl, tetrahydrofuranyl, pyrrolidinyl, piperidinyl, piperazinyl, morpholinyl, azetidinyl, 8-oxo-3-aza-bicyclo[3.2.1]oct-3-yl, aza-bicyclo[2.2.1]hept-5-yl, 2-oxo-7-aza-[3,5]-spironon-7-yl, cyclopentyl and cyclohexyl are optionally substituted, independently, with 1-5 substituents of $R^9$;

each $R^9$, independently, is halo, haloalkyl, CN, OH, NO$_2$, NH$_2$, acetyl, —C(O)NHCH$_3$, oxo, $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, phenyl, pyridyl, pyrimidyl, pyrazinyl, pyridazinyl, pyrazolyl, isoxazolyl, thiazolyl, morpholinyl, pyrazolyl, isoxazolyl, dihydropyranyl, pyrrolyl, pyrrolidinyl, tetrahydropyrrolyl, piperazinyl, oxetanyl or dioxolyl, wherein each of the $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, phenyl, pyridyl, pyrimidyl, pyrazinyl, pyridazinyl, pyrazolyl, isoxazolyl, thiazolyl, morpholinyl, pyrazolyl, isoxazolyl, dihydropyranyl, pyrrolidinyl, oxetanyl or dioxolyl, is optionally substituted independently with 1-5 substituents of F, Cl, CN, NO$_2$, NH$_2$, OH, oxo, methyl, methoxyl, ethyl, ethoxyl, propyl, propoxyl, isopropyl, isopropoxyl, cyclopropyl, cyclopropylmethoxyl, butyl, butoxyl, isobutoxyl, tert-butoxyl, isobutyl, sec-butyl, tert-butyl, $C_{1-3}$alkylamino-, $C_{1-3}$dialkylamino, $C_{1-3}$thioalkoxyl, or oxetanyl; and —X—Y—Z— taken together is —$CR^{10}R^{10}$—$CR^{10}R^{10}$—$CR^{10}R^{10}$; or —Z— is absent and —X—Y— taken together is —$CR^{10}R^{10}$—$CR^{10}R^{10}$, —$CR^{10}$=$CR^{10}$—, —$NR^{11}$—$CHR^{10}$— or —$CHR^{10}$—$NR^{11}$—, wherein each $R^{10}$, independently, is H, F, Cl, Br, CF$_3$, OCF$_3$, $C_{1-6}$alkyl, CN, OH, —$OC_{1-6}$-alkyl, —$S(O)_oC_{1-6}$-alkyl, —$NHC_{1-6}$-alkyl or —$C(O)C_{1-6}$-alkyl, wherein the $C_{1-6}$-alkyl and $C_{1-6}$-alkyl portion of —$OC_{1-6}$-alkyl, —$S(O)_oC_{1-6}$-alkyl, —$NHC_{1-6}$-alkyl and —$C(O)C_{1-6}$-alkyl are optionally substituted with 1-3 substituents of F, oxo or OH; and each $R^{11}$, independently, is H, $C_{1-6}$-alkyl or CN.

In another embodiment of the present invention, the compounds, and solvates, tautomers, hydrates, stereoisomers and pharmaceutically acceptable salts thereof, are defined by Formula I, wherein $A^1$ is $CR^1$ or N;
$A^3$ is $CR^3$ or N;
$A^4$ is $CR^4$ or N;
$A^5$ is $CR^5$ or N;
$A^6$ is $CR^6$ or N;
$A^8$ is $CR^8$ or N, provided that no more than one of $A^1$, $A^3$, $A^4$, $A^5$, $A^6$ and $A^8$ is N;

each of $R^1$, $R^4$, $R^5$ and $R^8$, independently, is H, F, Cl, Br, CF$_3$, OCF$_3$, $C_{1-6}$alkyl, CN, OH, —$OC_{1-6}$-alkyl, —$S(O)_oC_{1-6}$-alkyl, —$NHC_{1-6}$-alkyl or —$C(O)C_{1-6}$-alkyl, wherein the $C_{1-6}$-alkyl and $C_{1-6}$-alkyl portion of —$OC_{1-6}$-alkyl, —$S(O)_oC_{1-6}$-alkyl, —$NHC_{1-6}$-alkyl and —$C(O)C_{1-6}$-alkyl are optionally substituted with 1-3 substituents of F, oxo or OH;

$R^2$ is Cl, Br, $C_{1-6}$-alkyl, $C_{2-4}$alkenyl, $C_{2-4}$alkynyl, CN, —$OC_{1-6}$alkyl, —$SC_{1-5}$alkyl, —$NHC_{1-6}$alkyl, —$N(C_{1-3}$alkyl$)_2$, —NH-phenyl, —NH-benzyl, phenyl, pyridyl, pyrimidyl, pyrazinyl, pyridazinyl, pyrazolyl, isoxazolyl, thiazolyl, pyranyl, dihydropyranyl, tetrahydropyranyl, furanyl, dihydrofuranyl, tetrahydrofuranyl, pyrrolyl, pyrrolidinyl, tetrahydropyrrolyl, piperidinyl, piperazinyl, morpholinyl, azetidinyl, 8-oxo-3-aza-bicyclo[3.2.1]oct-3-yl, aza-bicyclo[2.2.1]hept-5-yl, 2-oxo-7-aza-[3,5]-spironon-7-yl, cyclopentyl, cyclohexyl or —$Si(CH_3)_3$, wherein the $C_{1-6}$-alkyl, $C_{2-4}$alkenyl, $C_{2-4}$alkynyl, —$OC_{1-6}$alkyl, —$SC_{1-6}$alkyl, —$NHC_{1-6}$alkyl, —$N(C_{1-3}$alkyl$)_2$, —NH-phenyl, —NH-benzyl, phenyl, pyridyl, pyrimidyl, pyrazinyl, pyridazinyl, pyrazolyl, isoxazolyl, thiazolyl, pyranyl, dihydropyranyl, tetrahydropyranyl, furanyl, dihydrofuranyl, tetrahydrofuranyl, pyrrolidinyl, piperidinyl, piperazinyl, morpholinyl, azetidinyl, 8-oxo-3-aza-bicyclo[3.2.1]oct-3-yl, aza-bicyclo[2.2.1]hept-5-yl, 2-oxo-7-aza-[3,5]-spironon-7-yl, cyclopentyl and cyclohexyl are optionally substituted, independently, with 1-5 substituents of $R^9$;

each of $R^3$ and $R^6$, independently, is H, halo, haloalkyl, haloalkoxyl, $C_{1-6}$-alkyl, CN, OH, $OC_{1-6}$-alkyl, $S(O)_oC_{1-6}$-alkyl, $NHC_{1-6}$-alkyl or $C(O)C_{1-6}$-alkyl;

$R^7$ is $C_{1-6}$-alkyl, $C_{2-4}$alkenyl, $C_{2-4}$alkynyl, CN, —$OC_{1-6}$alkyl, —$SC_{1-6}$alkyl, —$NHC_{1-6}$alkyl, —$N(C_{1-3}$alkyl$)_2$, —NH-phenyl, —NH-benzyl, phenyl, pyridyl, pyrimidyl, pyrazinyl, pyridazinyl, pyrazolyl, isoxazolyl, thiazolyl, pyranyl, dihydropyranyl, tetrahydropyranyl, furanyl, dihydrofuranyl, tetrahydrofuranyl, pyrrolyl, pyrrolidinyl, tetrahydropyrrolyl, piperidinyl, piperazinyl, morpholinyl, azetidinyl, 8-oxo-3-aza-bicyclo[3.2.1]oct-3-yl, aza-bicyclo[2.2.1]hept-5-yl, 2-oxo-7-aza-[3,5]-spironon-7-yl, cyclopentyl or cyclohexyl, wherein the $C_{1-6}$-alkyl, $C_{2-4}$alkenyl, $C_{2-4}$alkynyl, —$OC_{1-6}$alkyl, —$SC_{1-6}$alkyl, —$NHC_{1-6}$alkyl, —$N(C_{1-3}$alkyl$)_2$, —NH-phenyl, —NH-benzyl, phenyl, pyridyl, pyrimidyl, pyrazinyl, pyridazinyl, pyrazolyl, isoxazolyl, thiazolyl, pyranyl, dihydropyranyl, tetrahydropyranyl, furanyl, dihydrofuranyl, tetrahydrofuranyl, pyrrolidinyl, piperidinyl, piperazinyl, morpholinyl, azetidinyl, 8-oxo-3-aza-bicyclo[3.2.1]oct-3-yl, aza-bicyclo[2.2.1]hept-5-yl, 2-oxo-7-aza-[3,5]-spironon-7-yl, cyclopentyl and cyclohexyl are optionally substituted, independently, with 1-5 substituents of $R^9$;

each $R^9$, independently, is halo, haloalkyl, CN, OH, $NO_2$, $NH_2$, acetyl, —C(O)$NHCH_3$, oxo, $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, morpholinyl, pyrazolyl, isoxazolyl, dihydropyranyl, pyrrolyl, pyrrolidinyl, tetrahydropyrrolyl, piperazinyl, oxetanyl or dioxolyl, wherein each of the $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, morpholinyl, pyrazolyl, isoxazolyl, dihydropyranyl, pyrrolidinyl, oxetanyl or dioxolyl, is optionally substituted independently with 1-5 substituents of F, Cl, CN, $NO_2$, $NH_2$, OH, oxo, methyl, methoxyl, ethyl, ethoxyl, propyl, propoxyl, isopropyl, isopropoxyl, cyclopropyl, cyclopropylmethoxyl, butyl, butoxyl, isobutoxyl, tert-butoxyl, isobutyl, sec-butyl, tert-butyl, $C_{1-3}$alkylamino, $C_{1-3}$dialkylamino, $C_{1-3}$thioalkoxyl, or oxetanyl; and —X—Y—Z— taken together is —$CR^{10}R^{10}$—$CR^{10}R^{10}$—$CR^{10}R^{10}$—; or —Z— is absent and —X—Y— taken together is —$CR^{10}R^{10}$—$CR^{10}R^{10}$, —$CR^{10}$=$CR^{10}$—, —$NR^{11}CHR^{10}$— or —$CHR^{10}$—$NR^{11}$—, wherein
each $R^{10}$, independently, is H, F, Cl, Br, $CF_3$, $OCF_3$, $C_{1-6}$alkyl, CN, OH, —$OC_{1-6}$alkyl, —$S(O)_oC_{1-6}$ alkyl, —$NHC_{1-6}$alkyl or —$C(O)C_{1-6}$alkyl, wherein the $C_{1-6}$alkyl and $C_{1-6}$alkyl portion of —$OC_{1-6}$alkyl, —$S(O)_oC_{1-6}$-alkyl, —$NHC_{1-6}$alkyl and —$C(O)C_{1-6}$alkyl are optionally substituted with 1-3 substituents of F, oxo or OH; and each $R^{11}$, independently, is H, $C_{1-6}$-alkyl or CN.

In another embodiment of the present invention, the compounds, and solvates, tautomers, hydrates, stereoisomers and pharmaceutically acceptable salts thereof, are defined by Formula I, wherein each of $R^1$, $R^4$, $R^5$ and $R^8$, independently, is H, F, Cl, $CF_3$, $OCF_3$, methyl, ethyl, CN, OH, $OCH_3$, $SCH_3$, $NHCH_3$ or $C(O)CH_3$;

one of $R^2$ and $R^7$, independently, is phenyl, pyridyl, pyrimidyl, pyrazinyl, pyridazinyl, pyrazolyl, isoxazolyl, thiazolyl, pyranyl, dihydropyranyl, tetrahydropyranyl, furanyl, dihydrofuranyl, tetrahydrofuranyl, pyrrolyl, pyrrolidinyl, tetrahydropyrrolyl, piperidinyl, piperazinyl, morpholinyl, azetidinyl, 8-oxo-3-aza-bicyclo[3.2.1]oct-3-yl, aza-bicyclo[2.2.1]hept-5-yl, 2-oxo-7-aza-[3,5]-spironon-7-yl, cyclopentyl, cyclohexyl or —$Si(CH_3)_3$, wherein the phenyl, pyridyl, pyrimidyl, pyrazinyl, pyridazinyl, pyrazolyl, isoxazolyl, thiazolyl, pyranyl, dihydropyranyl, tetrahydropyranyl, furanyl, dihydrofuranyl, tetrahydrofuranyl, pyrrolidinyl, piperidinyl, piperazinyl, morpholinyl, azetidinyl, 8-oxo-3-aza-bicyclo[3.2.1]oct-3-yl, aza-bicyclo[2.2.1]hept-5-yl, 2-oxo-7-aza-[3,5]-spironon-7-yl, cyclopentyl and cyclohexyl are optionally substituted, independently, with 1-3 substituents of $R^9$;

the other of $R^2$ and $R^7$, independently, is $C_{1-6}$-alkyl, $C_{2-4}$alkenyl, $C_{2-4}$alkynyl, CN, —$OC_{1-6}$ alkyl, —$SC_{1-6}$alkyl, —$NHC_{1-6}$alkyl, —$N(C_{1-3}$alkyl$)_2$, —$NHC(=O)R^9$, —$C(=O)NHR^9$, —$NHS(O)_2R^9$, —$S(O)_2NHR^9$, —$NHC_{1-6}$alkyl, —$N(C_{1-3}$alkyl$)_2$, —NH-phenyl or —NH-benzyl, wherein the $C_{1-6}$-alkyl, $C_{2-4}$alkenyl, $C_{2-4}$alkynyl, CN, —$OC_{1-6}$alkyl, —$SC_{1-6}$alkyl, —$NHC_{1-6}$alkyl, —$N(C_{1-3}$alkyl$)_2$, —$NHC(=O)R^9$, —$C(=O)NHR^9$, —$NHS(O)_2R^9$, —$S(O)_2NHR^9$, —NH-phenyl and —NH-benzyl are optionally substituted, independently, with 1-3 substituents of $R^9$;

each of $R^3$ and $R^6$, independently, is H, halo, haloalkyl, haloalkoxyl, $C_{1-6}$-alkyl, CN, OH, $OC_{1-6}$-alkyl, $SC_{1-6}$-alkyl, $NHC_{1-6}$-alkyl or $C(O)C_{1-6}$-alkyl; and —X—Y—Z— taken together is —$CR^{10}R^{10}$—$CR^{10}R^{10}$—$CR^{10}R^{10}$—; or —Z— is absent and —X—Y— taken together is —$CR^{10}R^{10}$—$CR^{10}R^{10}$, —$CR^{10}$=$CR^{10}$—, —$NR^{11}$—$CHR^{10}$— or —$CHR^{10}$—$NR^{11}$—, wherein
each $R^{10}$, independently, is H, F, Cl, Br, $CF_3$, $OCF_3$, $C_{1-6}$-alkyl, CN, OH, —$OC_{1-6}$-alkyl, —$S(O)_oC_{1-6}$-alkyl, —$NHC_{1-6}$-alkyl or —$C(O)C_{1-6}$-alkyl, wherein the $C_{1-6}$-alkyl and $C_{1-6}$-alkyl portion of —$OC_{1-6}$-alkyl, —$S(O)_oC_{1-6}$-alkyl, —$NHC_{1-6}$-alkyl and —$C(O)C_{1-6}$-alkyl are optionally substituted with 1-3 substituents of F, oxo or OH; and each $R^{11}$, independently, is H, $C_{1-6}$-alkyl or CN, in conjunction with any of the above or below embodiments.

In another embodiment of the present invention, the compounds, and solvates, tautomers, hydrates, stereoisomers and pharmaceutically acceptable salts thereof, are defined by Formula I, wherein $A^1$ is CH or CF;
$A^3$ is CH, CF or N;
$A^4$ is CH, CF or N;
$A^5$ is CH;
$A^6$ is CH;
$A^8$ is CH;

$R^2$ is $C_{3-6}$-alkyl, $C_{2-4}$alkynyl, —$OC_{1-6}$alkyl, —$SC_{1-6}$alkyl, phenyl, pyridyl, pyrimidyl, pyrazinyl, pyridazinyl, dihydropyranyl, tetrahydropyranyl, pyrrolidinyl, piperidinyl, morpholinyl or 8-oxo-3-aza-bicyclo[3.2.1]oct-3-yl, wherein the $C_{3-6}$-alkyl, $C_{2-4}$alkynyl, —$OC_{1-6}$alkyl, —$SC_{1-6}$alkyl, phenyl, pyridyl, pyrimidyl, pyrazinyl, pyridazinyl, dihydropyranyl, tetrahydropyranyl, pyrrolidinyl, piperidinyl, morpholinyl and 8-oxo-3-aza-bicyclo[3.2.1]oct-3-yl, are optionally substituted, independently, with 1-5 substituents of $R^9$;

$R^7$ is $C_{2-4}$alkynyl, —$OC_{1-6}$alkyl, phenyl, pyridyl, pyrimidyl, pyrazinyl or pyridazinyl, wherein the $C_{2-4}$alkynyl, —$OC_{1-6}$alkyl, pyridyl, pyrimidyl, pyrazinyl and pyridazinyl are optionally substituted, independently, with 1-3 substituents of $R^9$;

each $R^9$, independently, is halo, haloalkyl, CN, OH, $NO_2$, $NH_2$, acetyl, —C(O)$NHCH_3$, oxo, $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, morpholinyl, pyrazolyl, isoxazolyl, dihydropyranyl, pyrrolyl, pyrrolidinyl, tetrahydropyrrolyl, piperazinyl, oxetanyl or dioxolyl, wherein each of the $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, morpholinyl, pyrazolyl, isoxazolyl, dihydropyranyl, pyrrolidinyl, oxetanyl or dioxolyl, is optionally substituted independently with 1-5 substituents of F, Cl, CN, $NO_2$, $NH_2$, OH, oxo, methyl, methoxyl, ethyl, ethoxyl, propyl, propoxyl, isopropyl, isopropoxyl, cyclopropyl, cyclopropylmethoxyl, butyl, butoxyl, isobutoxyl, tert-butoxyl, isobutyl, sec-butyl, tert-butyl, $C_{1-3}$alkylamino-, $C_{1-3}$dialkylamino, $C_{1-3}$thioalkoxyl, or oxetanyl; and —X—Y—Z— taken together is —$CR^{10}R^{10}$—$CR^{10}R^{10}$—$CR^{10}R^{10}$—; or —Z— is absent and —X—Y— taken together is —$CR^{10}R^{10}$—$CR^{10}R^{10}$, —$CR^{10}$=$CR^{10}$—, —$NR^{11}$—$CHR^{10}$— or —$CHR^{10}$—$NR^{11}$—, wherein each $R^{10}$, independently, is H, F, Cl, Br, $CF_3$, $OCF_3$, $C_{1-6}$-alkyl, CN, OH, —OC$_{1-6}$-alkyl, —S(O)$_o$C$_{1-6}$-alkyl, —NHC$_{1-6}$-alkyl or —C(O)C$_{1-6}$-alkyl, wherein the C$_{1-6}$-alkyl and C$_{1-6}$-alkyl portion of —OC$_{1-6}$-alkyl, —S(O)$_o$C$_{1-6}$alkyl, —NHC$_{1-6}$-alkyl and —C(O)C$_{1-6}$-alkyl are optionally substituted with 1-3 substituents of F, oxo or OH, and each R$^{11}$, independently, is H, C$_{1-6}$-alkyl or CN.

In another embodiment of the present invention, the compounds, and hydrates, solvates, tautomers, stereoisomers and pharmaceutically acceptable salts thereof, are defined by Formula II

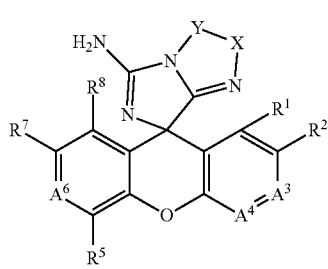

II wherein
  A$^3$ is CR$^3$ or N;
  A$^4$ is CR$^4$ or N;
  A$^6$ is CR$^6$ or N, provided that no more than one of A$^3$, A$^4$ and A$^6$ is N;
  each of R$^3$, R$^4$, R$^5$ and R$^8$, independently, is H, F, Cl, Br, CF$_3$, OCF$_3$, C$_{1-6}$-alkyl, CN, OH, —OC$_{1-6}$-alkyl, —S(O)$_o$ C$_{1-6}$-alkyl, —NHC$_{1-6}$-alkyl or —C(O)C$_{1-6}$-alkyl, wherein the C$_{1-6}$-alkyl and C$_{1-6}$-alkyl portion of —OC$_{1-6}$alkyl, —S(O)$_o$C$_{1-6}$-alkyl, —NHC$_{1-6}$-alkyl and —C(O)C$_{1-6}$-alkyl are optionally substituted with 1-3 substituents of F, oxo or OH;
  R$^2$ is Cl, Br, C$_{1-6}$-alkyl, C$_{2-4}$alkenyl, C$_{2-4}$alkynyl, CN, —OC$_{1-6}$alkyl, —SC$_{1-6}$alkyl, —NHC$_{1-6}$alkyl, —N(C$_{1-3}$alkyl)$_2$, —NH-phenyl, —NH-benzyl, phenyl, pyridyl, pyrimidyl, pyrazinyl, pyridazinyl, pyrazolyl, isoxazolyl, thiazolyl, pyranyl, dihydropyranyl, tetrahydropyranyl, furanyl, dihydrofuranyl, tetrahydropyranyl, pyrrolyl, pyrrolidinyl, tetrahydropyrrolyl, piperidinyl, piperazinyl, morpholinyl, azetidinyl, 8-oxo-3-aza-bicyclo[3.2.1]oct-3-yl, am-bicyclo [2.2.1]hept-5-yl, 2-oxo-7-aza-[3,5]-spironon-7-yl, cyclopentyl, cyclohexyl or —Si(CH$_3$)$_3$, wherein the C$_{1-6}$-alkyl, C$_{2-4}$alkenyl, C$_{2-4}$alkynyl, —OC$_{1-6}$alkyl, —SC$_{1-6}$alkyl, —NHC$_{1-6}$alkyl, —N(C$_{1-3}$alkyl)$_2$, —NH-phenyl, —NH-benzyl, phenyl, pyridyl, pyrimidyl, pyrazinyl, pyridazinyl, pyrazolyl, isoxazolyl, thiazolyl, pyranyl, dihydropyranyl, tetrahydropyranyl, furanyl, dihydrofuranyl, tetrahydropyranyl, pyrrolidinyl, piperidinyl, piperazinyl, morpholinyl, azetidinyl, 8-oxo-3-aza-bicyclo[3.2.1]oct-3-yl, aza-bicyclo[2.2.1]hept-5-yl, 2-oxo-7-aza-[3,5]-spironon-7-yl, cyclopentyl and cyclohexyl are optionally substituted, independently, with 1-5 substituents of R$^9$;
  each of R$^3$ and R$^6$, independently, is H, halo, haloalkyl, haloalkoxyl, C$_{1-6}$-alkyl, CN, OH, OC$_{1-6}$-alkyl, S(O)$_o$C$_{1-6}$-alkyl, NHC$_{1-6}$-alkyl or C(O)C$_{1-6}$-alkyl;
  R$^7$ is C$_{1-6}$-alkyl, C$_{2-4}$alkenyl, C$_{2-4}$alkynyl, CN, —OC$_{1-6}$alkyl, —SC$_{1-6}$alkyl, —NHC$_{1-6}$alkyl, —N(C$_{1-3}$alkyl)$_2$, —NHC(=O)R$^9$, —C(=O)NHR$^9$, —NHS(O)$_2$R$^9$, —S(O)$_2$NHR$^9$, —NH-phenyl, —NH-benzyl, phenyl, pyridyl, pyrimidyl, pyrazinyl, pyridazinyl, pyrazolyl, isoxazolyl, thiazolyl, pyranyl, dihydropyranyl, tetrahydropyranyl, furanyl, dihydrofuranyl, tetrahydrofuranyl, pyrrolyl, pyrrolidinyl, tetrahydropyrrolyl, piperidinyl, piperazinyl, morpholinyl, azetidinyl, 8-oxo-3-aza-bicyclo[3.2.1]oct-3-yl, aza-bicyclo[2.2.1]hept-5-yl, 2-oxo-7-aza-[3,5]-spironon-7-yl, cyclopentyl or cyclohexyl, wherein the C$_{1-6}$-alkyl, C$_{2-4}$alkenyl, C$_{2-4}$alkynyl, —OC$_{1-6}$alkyl, —SC$_{1-6}$alkyl, —NHC$_{1-6}$alkyl, —N(C$_{1-3}$alkyl)$_2$, —NHC(=O)R$^9$, —C(=O)NHR$^9$, —NHS(O)$_2$R$^9$, —S(O)$_2$NHR$^9$, —NH-phenyl, —NH-benzyl, phenyl, pyridyl, pyrimidyl, pyrazinyl, pyridazinyl, pyrazolyl, isoxazolyl, thiazolyl, pyranyl, dihydropyranyl, tetrahydropyranyl, furanyl, dihydrofuranyl, tetrahydrofuranyl, pyrrolidinyl, piperidinyl, piperazinyl, morpholinyl, azetidinyl, 8-oxo-3-aza-bicyclo[3.2.1]oct-3-yl, aza-bicyclo[2.2.1]hept-5-yl, 2-oxo-7-aza-[3,5]-spironon-7-yl, cyclopentyl and cyclohexyl are optionally substituted, independently, with 1-5 substituents of R$^9$;
  each R$^9$, independently, is halo, haloalkyl, CN, OH, NO$_2$, NH$_2$, acetyl, —C(O)NHCH$_3$, oxo, C$_{1-6}$alkyl, C$_{2-6}$alkenyl, C$_{2-6}$alkynyl, C$_{3-6}$cycloalkyl, C$_{1-6}$alkylamino-, C$_{1-6}$dialkylamino-, C$_{1-6}$alkoxyl, C$_{1-6}$thioalkoxyl, phenyl, pyridyl, pyrimidyl, pyrazinyl, pyridazinyl, pyrazolyl, isoxazolyl, thiazolyl, morpholinyl, pyrazolyl, isoxazolyl, dihydropyranyl, pyrrolyl, pyrrolidinyl, tetrahydropyrrolyl, piperazinyl, oxetanyl or dioxolyl, wherein each of the C$_{1-6}$alkyl, C$_{2-6}$alkenyl, C$_{2-6}$alkynyl, C$_{3-6}$cycloalkyl, C$_{1-6}$alkylamino-, C$_{1-6}$dialkylamino-, C$_{1-6}$alkoxyl, C$_{1-6}$thioalkoxyl, phenyl, pyridyl, pyrimidyl, pyrazinyl, pyridazinyl, pyrazolyl, isoxazolyl, thiazolyl, morpholinyl, pyrazolyl, isoxazolyl, dihydropyranyl, pyrrolidinyl, oxetanyl or dioxolyl, is optionally substituted independently with 1-5 substituents of F, Cl, CN, NO$_2$, NH$_2$, OH, oxo, methyl, methoxyl, ethyl, ethoxyl, propyl, propoxyl, isopropyl, isopropoxyl, cyclopropyl, cyclopropylmethoxyl, butyl, butoxyl, isobutoxyl, tert-butoxyl, isobutyl, sec-butyl, tert-butyl, C$_{1-3}$alkylamino-, C$_{1-3}$dialkylamino, C$_{1-3}$thioalkoxyl, or oxetanyl; and
  —X—Y— taken together is —CHR$^{10}$—CHR$^{10}$—, —CR$^{10}$=CR$^{10}$—, —NR$^{11}$—CHR$^{10}$— or —CHR$^{10}$—NR$^{11}$—, wherein
    each R$^{10}$, independently, is H, F, Cl, Br, CF$_3$, OCF$_3$, C$_{1-6}$-alkyl, CN, OH, —OC$_{1-6}$-alkyl, —S(O)$_o$C$_{1-6}$-alkyl, —NHC$_{1-6}$-alkyl or —C(O)C$_{1-6}$-alkyl, wherein the C$_{1-6}$-alkyl and C$_{1-6}$-alkyl portion of —OC$_{1-6}$-alkyl, —S(O)$_o$C$_{1-6}$-alkyl, —NHC$_{1-6}$-alkyl and —C(O)C$_{1-6}$-alkyl are optionally substituted with 1-3 substituents of F, oxo or OH;
    and each R$^{11}$, independently, is H, C$_{1-6}$-alkyl or CN.

In another embodiment of the present invention, the compounds, and solvates, tautomers, stereoisomers and pharmaceutically acceptable salts thereof, are defined by Formula II-A

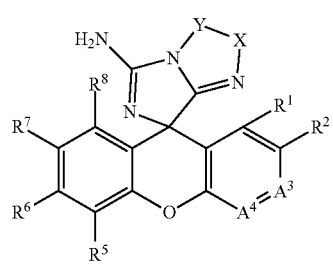

II-A wherein each of A$^3$, A$^4$, R$^1$, R$^2$, R$^5$, R$^6$, R$^7$, R$^8$, X and Y is as defined above with respect to Formula I or Formula II.

In another embodiment of the present invention, the compounds, and hydrates, solvates, tautomers, stereoisomers and pharmaceutically acceptable salts thereof, are defined by Formula II-B

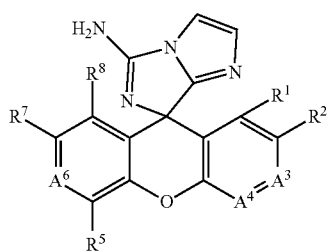

wherein $A^3$ is $CR^3$ or N;

$A^4$ is $CR^4$ or N;

$A^6$ is $CR^6$ or N, provided that no more than one of $A^3$, $A^4$ and $A^6$ is N;

each of $R^1$, $R^4$, $R^5$ and $R^8$, independently, is H, F, Cl, Br, $CF_3$, $OCF_3$, $C_{1-6}$-alkyl, CN, OH, —$OC_{1-6}$-alkyl, —$S(O)_o$$C_{1-6}$-alkyl, —$NHC_{1-6}$-alkyl or —$C(O)C_{1-6}$-alkyl, wherein the $C_{1-6}$-alkyl and $C_{1-6}$-alkyl portion of —$OC_{1-6}$-alkyl, —$S(O)_o$$C_{1-6}$-alkyl, —$NHC_{1-6}$-alkyl and —$C(O)C_{1-6}$-alkyl are optionally substituted with 1-3 substituents of F, oxo or OH;

$R^2$ is Cl, Br, $C_{1-6}$-alkyl, $C_{2-4}$alkenyl, $C_{2-4}$alkynyl, CN, —$OC_{1-6}$alkyl, —$SC_{1-6}$alkyl, —$NHC_{1-6}$alkyl, —$N(C_{1-3}$alkyl$)_2$, —NH-phenyl, —NH-benzyl, phenyl, pyridyl, pyrimidyl, pyrazinyl, pyridazinyl, pyrazolyl, isoxazolyl, thiazolyl, pyranyl, dihydropyranyl, tetrahydropyranyl, furanyl, dihydrofuranyl, tetrahydrofuranyl, pyrrolyl, pyrrolidinyl, tetrahydropyrrolyl, piperidinyl, piperazinyl, morpholinyl, azetidinyl, 8-oxo-3-aza-bicyclo[3.2.1]oct-3-yl, aza-bicyclo[2.2.1]hept-5-yl, 2-oxo-7-aza-[3,5]-spironon-7-yl, cyclopentyl, cyclohexyl or —$Si(CH_3)_3$, wherein the $C_{1-6}$-alkyl, $C_{2-4}$alkenyl, $C_{2-4}$alkynyl, —$OC_{1-6}$alkyl, —$SC_{1-6}$alkyl, —$NHC_{1-6}$alkyl, —$N(C_{1-3}$alkyl$)_2$, —NH-phenyl, —NH-benzyl, phenyl, pyridyl, pyrimidyl, pyrazinyl, pyridazinyl, pyrazolyl, isoxazolyl, thiazolyl, pyranyl, dihydropyranyl, tetrahydropyranyl, furanyl, dihydrofuranyl, tetrahydrofuranyl, pyrrolidinyl, piperidinyl, piperazinyl, morpholinyl, azetidinyl, 8-oxo-3-aza-bicyclo[3.2.1]oct-3-yl, aza-bicyclo[2.2.1]hept-5-yl, 2-oxo-7-aza-[3,5]-spironon-7-yl, cyclopentyl and cyclohexyl are optionally substituted; independently, with 1-5 substituents of $R^9$;

each of $R^3$ and $R^6$, independently, is H, halo, haloalkyl, haloalkoxyl, $C_{1-6}$-alkyl, CN, OH, $OC_{1-6}$-alkyl, $S(O)_o$$C_{1-6}$-alkyl, $NHC_{1-6}$-alkyl or $C(O)C_{1-6}$-alkyl;

$R^7$ is $C_{1-6}$-alkyl, $C_{2-4}$alkenyl, $C_{2-4}$alkynyl, CN, —$OC_{1-6}$alkyl, —$SC_{1-6}$alkyl, —$NHC_{1-6}$alkyl, —$N(C_{1-3}$alkyl$)_2$, —NHC(=O)$R^9$, —C(=O)NH$R^9$, —NHS(O)$_2$$R^9$, —S(O)$_2$NH$R^9$, —NH-phenyl, —NH-benzyl, phenyl, pyridyl, pyrimidyl, pyrazinyl, pyridazinyl, pyrazolyl, isoxazolyl, thiazolyl, pyranyl, dihydropyranyl, tetrahydropyranyl, furanyl, dihydrofuranyl, tetrahydrofuranyl, pyrrolyl, pyrrolidinyl, tetrahydropyrrolyl, piperidinyl, piperazinyl, morpholinyl, azetidinyl, 8-oxo-3-aza-bicyclo[3.2.1]oct-3-yl, aza-bicyclo[2.2.1]hept-5-yl, 2-oxo-7-aza-[3,5]-spironon-7-yl, cyclopentyl or cyclohexyl, wherein the $C_{1-6}$-alkyl, $C_{2-4}$alkenyl, $C_{2-4}$alkynyl, —$OC_{1-6}$alkyl, —$SC_{1-6}$alkyl, —$NHC_{1-6}$alkyl, —$N(C_{1-3}$alkyl$)_2$, —NHC(=O)$R^9$, —C(O)NH$R^9$, —NHS(O)$_2$$R^9$, —S(O)$_2$NH$R^9$, —NH-phenyl, —NH-benzyl, phenyl, pyridyl, pyrimidyl, pyrazinyl, pyridazinyl, pyrazolyl, isoxazolyl, thiazolyl, pyranyl, dihydropyranyl, tetrahydropyranyl, furanyl, dihydrofuranyl, tetrahydrofuranyl, pyrrolidinyl, piperidinyl, piperazinyl, morpholinyl, azetidinyl, 8-oxo-3-aza-bicyclo[3.2.1]oct-3-yl, aza-bicyclo[2.2.1]hept-5-yl, 2-oxo-7-aza-[3,5]-spironon-7-yl, cyclopentyl and cyclohexyl are optionally substituted, independently, with 1-5 substituents of $R^9$;

each $R^9$, independently, is halo, haloalkyl, CN, OH, $NO_2$, $NH_2$, acetyl, —C(O)NHCH$_3$, oxo, $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, phenyl, pyridyl, pyrimidyl, pyrazinyl, pyridazinyl, pyrazolyl, isoxazolyl, thiazolyl, morpholinyl, pyrazolyl, isoxazolyl, dihydropyranyl, pyrrolyl, pyrrolidinyl, tetrahydropyrrolyl, piperazinyl, oxetanyl or dioxolyl, wherein each of the $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, phenyl, pyridyl, pyrimidyl, pyrazinyl, pyridazinyl, pyrazolyl, isoxazolyl, thiazolyl, morpholinyl, pyrazolyl, isoxazolyl, dihydropyranyl, pyrrolidinyl, oxetanyl or dioxolyl, is optionally substituted independently with 1-5 substituents of F, Cl, CN, $NO_2$, $NH_2$, OH, oxo, methyl, methoxyl, ethyl, ethoxyl, propyl, propoxyl, isopropyl, isopropoxyl, cyclopropyl, cyclopropylmethoxyl, butyl, butoxyl, isobutoxyl, tert-butoxyl, isobutyl, sec-butyl, tert-butyl, $C_{1-3}$alkylamino-, $C_{1-3}$dialkylamino, $C_{1-3}$thioalkoxyl, or oxetanyl; and —X—Y— taken together is —CHR$^{10}$—CHR$^{10}$—, —CR$^{10}$=CR$^{10}$—, —NR$^{10}$—CHR$^{10}$— or —CHR$^{10}$—NR$^{10}$—, wherein each $R^{10}$, independently, is H, F, Cl, Br, CF$_3$, OCF$_3$, $C_{1-6}$-alkyl, CN, OH, —$OC_{1-6}$-alkyl, —S(O)$_o$$C_{1-6}$-alkyl, —NHC$_{1-6}$-alkyl or —C(O)C$_{1-6}$-alkyl, wherein the $C_{1-6}$-alkyl and $C_{1-6}$-alkyl portion of —$OC_{1-6}$-alkyl, —S(O)$_o$$C_{1-6}$-alkyl, —NHC$_{1-6}$-alkyl and —C(O)C$_{1-6}$-alkyl are optionally substituted with 1-3 substituents of F, oxo or OH; and each $R^{11}$, independently, is H, $C_{1-6}$-alkyl or CN.

In another embodiment of the present invention, the compounds, and hydrates, solvates, tautomers, stereoisomers and pharmaceutically acceptable salts thereof, are defined by Formula III

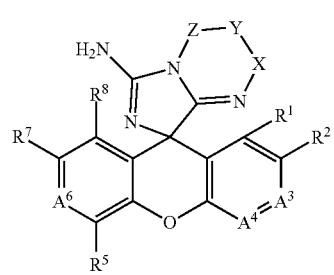

wherein $A^3$ is $CR^3$ or N;

$A^4$ is $CR^4$ or N;

$A^6$ is $CR^6$ or N, provided that no more than one of $A^3$, $A^4$ and $A^6$ is N;

each of $R^1$, $R^4$, $R^5$ and $R^8$, independently, is H, F, Cl, Br, $CF_3$, $OCF_3$, $C_{1-6}$-alkyl, CN, OH, —$OC_{1-6}$-alkyl, —S(O)$_o$$C_{1-6}$-alkyl, —NHC$_{1-6}$-alkyl or —C(O)C$_{1-6}$-alkyl, wherein the $C_{1-6}$-alkyl and $C_{1-6}$-alkyl portion of —$OC_{1-6}$- alkyl, —S(O)$_o$C$_{1-6}$-alkyl, —NHC$_{1-6}$-alkyl and —C(O)C$_{1-6}$-alkyl are optionally substituted with 1-3 substituents of F, oxo or OH;

R$^2$ is Cl, Br, C$_{1-6}$-alkyl, C$_{2-4}$alkenyl, C$_{2-4}$alkynyl, CN, OC$_{1-6}$alkyl, —SC$_{1-6}$alkyl, —NHC$_{1-6}$alkyl, —N(C$_{1-3}$alkyl)$_2$, —NH-phenyl, —NH-benzyl, phenyl, pyridyl, pyrimidyl, pyrazinyl, pyridazinyl, pyrazolyl, isoxazolyl, thiazolyl, pyranyl, dihydropyranyl, tetrahydropyranyl, furanyl, dihydrofuranyl, tetrahydrofuranyl, pyrrolyl, pyrrolidinyl, tetrahydropyrrolyl, piperidinyl, piperazinyl, morpholinyl, azetidinyl, 8-oxo-3-aza-bicyclo[3.2.1]oct-3-yl, aza-bicyclo[2.2.1]hept-5-yl, 2-oxo-7-aza-[3,5]-spironon-7-yl, cyclopentyl, cyclohexyl or —Si(CH$_3$)$_3$, wherein the C$_{1-6}$-alkyl, C$_{2-4}$alkenyl, C$_{2-4}$alkynyl, —OC$_{1-6}$alkyl, —SC$_{1-6}$alkyl, —NHC$_{1-6}$alkyl, —N(C$_{1-3}$alkyl)$_2$, —NH-phenyl, —NH-benzyl, phenyl, pyridyl, pyrimidyl, pyrazinyl, pyridazinyl, pyrazolyl, isoxazolyl, thiazolyl, pyranyl, dihydropyranyl, tetrahydropyranyl, furanyl, dihydrofuranyl, tetrahydrofuranyl, pyrrolidinyl, piperidinyl, piperazinyl, morpholinyl, azetidinyl, 8-oxo-3-aza-bicyclo[3.2.1]oct-3-yl, aza-bicyclo[2.2.1]hept-5-yl, 2-oxo-7-aza-[3,5]-spironon-7-yl, cyclopentyl and cyclohexyl are optionally substituted, independently, with 1-5 substituents of R$^9$;

each of R$^3$ and R$^6$, independently, is H, halo, haloalkyl, haloalkoxy, C$_{1-6}$-alkyl, CN, OH, OC$_{1-6}$-alkyl, S(O)$_o$C$_{1-6}$-alkyl, NHC$_{1-6}$-alkyl or C(O)C$_{1-6}$-alkyl;

R$^7$ is C$_{1-6}$-alkyl, C$_{2-4}$alkenyl, C$_{2-4}$alkynyl, CN, —OC$_{1-6}$alkyl, —SC$_{1-6}$alkyl, —NHC$_{1-6}$alkyl, —N(C$_{1-3}$alkyl)$_2$, —NHC(=O)R$^9$, —C(=O)NHR$^9$, —NHS(O)$_2$R$^9$, —S(O)$_2$NHR$^9$, —NH-phenyl, —NH-benzyl, phenyl, pyridyl, pyrimidyl, pyrazinyl, pyridazinyl, pyrazolyl, isoxazolyl, thiazolyl, pyranyl, dihydropyranyl, tetrahydropyranyl, furanyl, dihydrofuranyl, tetrahydrofuranyl, pyrrolyl, pyrrolidinyl, tetrahydropyrrolyl, piperidinyl, piperazinyl, morpholinyl, azetidinyl, 8-oxo-3-aza-bicyclo[3.2.1]oct-3-yl, aza-bicyclo[2.2.1]hept-5-yl, 2-oxo-7-aza-[3,5]-spironon-7-yl, cyclopentyl or cyclohexyl, wherein the C$_{1-6}$-alkyl, C$_{2-4}$alkenyl, C$_{2-4}$alkynyl, —OC$_{1-6}$alkyl, —SC$_{1-6}$alkyl, —NHC$_{1-6}$alkyl, —N(C$_{1-3}$alkyl)$_2$, —NHC(=O)R$^9$, —C(=O)NHR$^9$, —NHS(O)$_2$R$^9$, —S(O)$_2$NHR$^9$, —NH-phenyl, —NH-benzyl, phenyl, pyridyl, pyrimidyl, pyrazinyl, pyridazinyl, pyrazolyl, isoxazolyl, thiazolyl, pyranyl, dihydropyranyl, tetrahydropyranyl, furanyl, dihydrofuranyl, tetrahydrofuranyl, pyrrolidinyl, piperidinyl, piperazinyl, morpholinyl, azetidinyl, 8-oxo-3-aza-bicyclo[3.2.1]oct-3-yl, aza-bicyclo[2.2.1]hept-5-yl, 2-oxo-7-aza-[3,5]-spironon-7-yl, cyclopentyl and cyclohexyl are optionally substituted, independently, with 1-5 substituents of R$^9$;

each R$^9$, independently, is halo, haloalkyl, CN, OH, NO$_2$, NH$_2$, acetyl, —C(O)NHCH$_3$, oxo, C$_{1-6}$alkyl, C$_{2-6}$alkenyl, C$_{2-6}$alkynyl, C$_{3-6}$cycloalkyl, C$_{1-6}$alkylamino-, C$_{1-6}$dialkylamino-, C$_{1-6}$alkoxyl, C$_{1-6}$thioalkoxyl, phenyl, pyridyl, pyrimidyl, pyrazinyl, pyridazinyl, pyrazolyl, isoxazolyl, thiazolyl, morpholinyl, pyrazolyl, isoxazolyl, dihydropyranyl, pyrrolyl, pyrrolidinyl, tetrahydropyrrolyl, piperazinyl, oxetanyl or dioxolyl, wherein each of the C$_{1-6}$alkyl, C$_{2-6}$alkenyl, C$_{2-6}$alkynyl, C$_{3-6}$cycloalkyl, C$_{1-6}$alkylamino-, C$_{1-6}$dialkylamino-, C$_{1-6}$alkoxyl, C$_{1-6}$thioalkoxyl, phenyl, pyridyl, pyrimidyl, pyrazinyl, pyridazinyl, pyrazolyl, isoxazolyl, thiazolyl, morpholinyl, pyrazolyl, isoxazolyl, dihydropyranyl, pyrrolidinyl, oxetanyl or dioxolyl, is optionally substituted independently with 1-5 substituents of F, Cl, CN, NO$_2$, NH$_2$, OH, oxo, methyl, methoxyl, ethyl, ethoxyl, propyl, propoxyl, isopropyl, isopropoxyl, cyclopropyl, cyclopropylmethoxyl, butyl, butoxyl, isobutoxyl, tert-butoxyl, isobutyl, sec-butyl, tert-butyl, C$_{1-3}$alkylamino-, C$_{1-3}$dialkylamino, C$_{1-3}$thioalkoxyl, or oxetanyl; and —X—Y—Z— taken together is —CR$^{10}$R$^{10}$—CR$^{10}$R$^{10}$—CR$^{10}$R$^{10}$, wherein each R$^{10}$, independently, is H, F, Cl, Br, CF$_3$, OCF$_3$, C$_{1-6}$-alkyl, CN, OH, —OC$_{1-6}$-alkyl, —S(O)$_o$C$_{1-6}$-alkyl, —NHC$_{1-6}$-alkyl or —C(O)C$_{1-6}$-alkyl, wherein the C$_{1-6}$-alkyl and C$_{1-6}$-alkyl portion of —OC$_{1-6}$-alkyl, —S(O)$_o$C$_{1-6}$-alkyl, —NHC$_{1-6}$-alkyl and —C(O)C$_{1-6}$-alkyl are optionally substituted with 1-3 substituents of F, oxo or OH.

The present invention contemplates that the various different embodiments of Formulas I, II and III, and sub-Formulas thereof, described herein, may comprise the following embodiments with respect to individual variables of A$^1$, A$^3$, A$^4$, A$^5$, A$^6$, A$^8$, R$^2$, R$^7$, X, Y and/or Z where applicable, as described below. Hence, these embodiments with respect to individual variables A$^1$, A$^3$, A$^4$, A$^5$, A$^6$, A$^8$, R$^2$, R$^7$, X, Y and Z, where applicable, may be applied "in conjunction with any of the other {above and below} embodiments" to create various embodiments of general Formulas I, II and III and each sub-formula thereof, which are not literally described herein.

In another embodiment, the invention includes compounds wherein A$^1$ is CH, CF or N, in conjunction with any of the above or below embodiments.

In another embodiment, the invention includes compounds wherein A$^1$ is CH or CF, in conjunction with any of the above or below embodiments.

In another embodiment, the invention includes compounds wherein A$^1$ is CF, in conjunction with any of the above or below embodiments.

In another embodiment, the invention includes compounds wherein A$^1$ is N, in conjunction with any of the above or below embodiments.

In another embodiment, the invention includes compounds wherein A$^3$ is CH, CF or N, in conjunction with any of the above or below embodiments.

In another embodiment, the invention includes compounds wherein A$^3$ is CH or N, in conjunction with any of the above or below embodiments.

In another embodiment, the invention includes compounds wherein A$^3$ is CH or CF, in conjunction with any of the above or below embodiments.

In another embodiment, the invention includes compounds wherein A$^3$ is CF, in conjunction with any of the above or below embodiments.

In another embodiment, the invention includes compounds wherein A$^3$ is N, in conjunction with any of the above or below embodiments.

In another embodiment, the invention includes compounds wherein A$^4$ is CH, CF or N, in conjunction with any of the above or below embodiments.

In another embodiment, the invention includes compounds wherein A$^4$ is CH or CF, in conjunction with any of the above or below embodiments.

In another embodiment, the invention includes compounds wherein A$^4$ is CF or N, in conjunction with any of the above or below embodiments.

In another embodiment, the invention includes compounds wherein A$^4$ is CH or N, in conjunction with any of the above or below embodiments.

In another embodiment, the invention includes compounds wherein A$^4$ is CF, in conjunction with any of the above or below embodiments.

In another embodiment, the invention includes compounds wherein A$^4$ is N, in conjunction with any of the above or below embodiments.

In another embodiment, the invention includes compounds wherein A$^5$ is CH, CF or N, in conjunction with any of the above or below embodiments.

In another embodiment, the invention includes compounds wherein $A^5$ is CH or CF, in conjunction with any of the above or below embodiments.

In another embodiment, the invention includes Compounds wherein $A^5$ is N, in conjunction with any of the above or below embodiments.

In another embodiment, the invention includes compounds wherein $A^6$ is $CR^6$ wherein $R^6$ is H, F, Br or

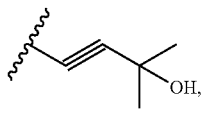

or $A^6$ is N, in conjunction with any of the above or below embodiments.

In another embodiment, the invention includes compounds wherein $A^6$ is CH, in conjunction with any of the above or below embodiments.

In another embodiment, the invention includes compounds wherein $A^6$ is N, in conjunction with any of the above or below embodiments.

In another embodiment, the invention includes compounds wherein $A^8$ is $CR^8$ wherein $R^8$ is F, Br or

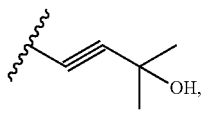 [SMILES: *C#CC(C)(C)O]

in conjunction with any of the above or below embodiments.

In another embodiment, the invention includes compounds wherein $A^8$ is CH, CF or N, in conjunction with any of the above or below embodiments.

In another embodiment, the invention includes compounds wherein $A^8$ is CH or CF, in conjunction with any of the above or below embodiments.

In another embodiment, the invention includes compounds wherein $A^8$ is N, in conjunction with any of the above or below embodiments.

In another embodiment, the invention includes compounds wherein $A^1$ is $CR^1$ or N, $A^3$ is $CR^3$ or N, $A^4$ is $CR^4$ or N, $A^5$ is $CR^5$ or N, $A^6$ is $CR^6$ or N and $A^8$ is $CR^8$ or N, provided that no more than one of $A^1, A^3, A^4, A^5, A^6$ and $A^8$ is N, in conjunction with any of the above or below embodiments.

In another embodiment, the invention includes compounds wherein $A^1$ is $CR^1$, $A^3$ is $CR^3$ or N, $A^4$ is $CR^4$ or N, $A^5$ is $CR^5$, $A^6$ is $CR^6$ and $A^8$ is $CR^8$, provided that no more than one of $A^3$ and $A^4$ is N, in conjunction with any of the above or below embodiments.

In another embodiment, the invention includes compounds wherein $A^1$ is $CR^1$, $A^3$ is N, $A^4$ is $CR^4$, $A^5$ is $CR^5$, $A^6$ is $CR^6$ and $A^8$ is $CR^8$, in conjunction with any of the above or below embodiments.

In another embodiment, the invention includes compounds wherein $A^1$ is $CR^1$, $A^3$ is $CR^3$, $A^4$ is N, $A^5$ is $CR^5$, $A^6$ is $CR^6$ and $A^8$ is $CR^8$, in conjunction with any of the above or below embodiments.

In another embodiment, the invention includes compounds wherein $A^1$ is $CR^1$, $A^3$ is $CR^3$, or N, $A^4$ is $CR^4$ or N, $A^5$ is $CR^5$, $A^6$ is $CR^6$ and $A^8$ is $CR^8$, wherein each of $R^1, R^4, R^5$ and $R^8$, independently, is H, F, Cl, Br, $CF_3$, $OCF_3$, $C_{1-6}$-alkyl, CN, OH, $-OC_{1-6}$-alkyl, $-S(O)_oC_{1-6}$-alkyl, $-NHC_{1-6}$-alkyl or $-C(O)C_{1-6}$-alkyl, wherein the $C_{1-6}$-alkyl and $C_{1-6}$-alkyl portion of $-OC_{1-6}$-alkyl, $-S(O)_oC_{1-6}$-alkyl, $-NHC_{1-6}$-alkyl and $-C(O)C_{1-6}$-alkyl are optionally substituted with 1-3 substituents of F, oxo or OH and each of $R^3$ and $R^6$, independently, is H, halo, haloalkyl, haloalkoxyl, $C_{1-6}$-alkyl, CN, OH, $OC_{1-6}$-alkyl, $S(O)_oC_{1-6}$-alkyl, $NHC_{1-6}$-alkyl or $C(O)C_{1-6}$-alkyl, provided that no more than one of $A^3$ and $A^4$ is N, in conjunction with any of the above or below embodiments.

In another embodiment, the invention includes compounds wherein $A^1$ is CH or CF, $A^3$ is CH, CF or N, $A^4$ is CH, CF or N, $A^5$ is CH, CF or N, $A^6$ is CH, CF or N, $A^8$ is CH or CF, and $R^{10}$ is H, $CH_3$, $C_2H_5$, propyl, butyl, acetyl or benzyl, in conjunction with any of the above or below embodiments.

In another embodiment, the invention includes compounds wherein $R^1$ is H, F, Cl, Br, $CF_3$, $OCF_3$, $C_{1-6}$-alkyl, CN, OH, $-OC_{1-6}$-alkyl, $-S(O)_oC_{1-6}$-alkyl, $-NHC_{1-6}$-alkyl or $-C(O)C_{1-6}$-alkyl, wherein the $C_{1-6}$-alkyl and $C_{1-6}$-alkyl portion of $-OC_{1-6}$-alkyl, $-S(O)_oC_{1-6}$-alkyl, $-NHC_{1-6}$-alkyl and $-C(O)C_{1-6}$-alkyl are optionally substituted with 1-3 substituents of F, oxo or OH, in conjunction with any of the above or below embodiments.

In another embodiment, the invention includes compounds wherein $R^1$ is H, F, Cl, $CF_3$, $OCF_3$, methyl, ethyl, CN, OH, $OCH_3$, $SCH_3$, $NHCH_3$ or $C(O)CH_3$, in conjunction with any of the above or below embodiments.

In another embodiment, the invention includes compounds wherein $R^1$ is H, F, methyl, CN or OH, in conjunction with any of the above or below embodiments.

In another embodiment, the invention includes compounds wherein $R^1$ is H or F, in conjunction with any of the above or below embodiments.

In another embodiment, the invention includes compounds wherein $R^1$ is H, in conjunction with any of the above or below embodiments.

In another embodiment, the invention includes compounds wherein $R^2$ is Cl, Br, $C_{1-6}$-alkyl, $C_{2-4}$alkenyl, $C_{2-4}$alkynyl, CN, $-OC_{1-6}$alkyl, $-SC_{1-6}$alkyl, $-NHC_{1-6}$alkyl, $-N(C_{1-3}$alkyl$)_2$, $-NH$-phenyl, $-NH$-benzyl, phenyl, pyridyl, pyrimidyl, pyrazinyl; pyridazinyl, pyrazolyl, isoxazolyl, thiazolyl, pyranyl, dihydropyranyl, tetrahydropyranyl, furanyl, dihydrofuranyl, tetrahydrofuranyl, pyrrolidinyl, piperidinyl, piperazinyl, morpholinyl, azetidinyl, 8-oxo-3-aza-bicyclo[3.2.1]oct-3-yl, aza-bicyclo[2.2.1]hept-5-yl, 2-oxo-7-aza-[3,5]-spironon-7-yl, cyclopentyl, cyclohexyl or $-Si(CH_3)_3$, wherein the $C_{1-6}$alkyl, $C_{2-4}$alkenyl, $C_{2-4}$alkynyl, $-SC_{1-6}$alkyl, $-SC_{1-6}$alkyl, $-NHC_{1-6}$alkyl, $-N(C_{1-3}$alkyl$)_2$, $-NH$-phenyl, $-NH$-benzyl, phenyl, pyridyl, pyrimidyl, pyrazinyl, pyridazinyl, pyrazolyl, isoxazolyl, thiazolyl, pyranyl, dihydropyranyl, tetrahydropyranyl, furanyl, dihydrofuranyl, tetrahydrofuranyl, pyrrolidinyl, piperidinyl, piperazinyl, morpholinyl, azetidinyl, 8-oxo-3-aza-bicyclo[3.2.1]oct-3-yl, aza-bicyclo[2.2.1]hept-5-yl, 2-oxo-7-aza-[3,5]-spironon-7-yl, cyclopentyl and cyclohexyl are optionally substituted, independently, with 1-5 substituents of $R^9$, in conjunction with any of the above or below embodiments.

In another embodiment, the invention includes compounds wherein $R^2$ is $C_{1-6}$-alkyl, $C_{2-4}$alkenyl, $C_{2-4}$alkynyl, $-OC_{1-6}$alkyl, phenyl, pyridyl, pyrimidyl, pyrazinyl, pyridazinyl, pyrazolyl, isoxazolyl, thiazolyl, pyranyl, dihydropyranyl, tetrahydropyranyl, furanyl, dihydrofuranyl, tetrahydropyranyl, pyrrolidinyl, tetrahydropyrrolyl, piperidinyl, piperazinyl, morpholinyl, azetidinyl, 8-oxo-3-aza-bicyclo[3.2.1]oct-3-yl, aza-bicyclo[2.2.1]hept-5-yl, 2-oxo-7-aza-[3,5]-spironon-7-yl, cyclopentyl, cyclohexyl or $-Si(CH_3)_3$, wherein the $C_{1-6}$-alkyl, $C_{2-4}$alkenyl, $C_{2-4}$alkynyl, $-OC_{1-6}$alkyl, phenyl, pyridyl, pyrimidyl, pyrazinyl, pyridazinyl, pyrazolyl, isoxazolyl, thiazolyl, pyranyl, dihydropyranyl, tetrahydropyranyl, furanyl, dihydrofuranyl, tetrahydrofuranyl, pyrrolidinyl, tetrahydropyrrolyl, piperidinyl, piperazinyl, morpholinyl, azetidinyl, 8-oxo-3-aza-bicyclo[3.2.1]oct-3-yl, aza-bicyclo[2.2.1]hept-5-yl, 2-oxo-7-aza-[3,5]-spironon-7-yl, cyclopentyl and cyclohexyl are optionally substituted, independently, with 1-3 substituents of $R^9$, in conjunction with any of the above or below embodiments.

In another embodiment, the invention includes compounds wherein $R^2$ is $C_{3-6}$-alkyl, $C_{3-8}$-cycloalkyl, $C_{2-4}$alkynyl, —$OC_{1-6}$alkyl, —$SC_{1-6}$alkyl, phenyl, pyridyl, pyrimidyl, pyrazinyl, pyridazinyl, dihydropyranyl, tetrahydropyranyl, pyrrolidinyl, tetrahydropyrrolyl, piperidinyl, morpholinyl or 8-oxo-3-aza-bicyclo[3.2.1]oct-3-yl, wherein the $C_{3-6}$-alkyl, $C_{3-8}$ cycloalkyl, $C_{2-4}$alkynyl, —$OC_{1-6}$alkyl, —$SC_{1-6}$alkyl, phenyl, pyridyl, pyrimidyl, pyrazinyl, pyridazinyl, dihydropyranyl, tetrahydropyranyl, pyrrolidinyl, tetrahydropyrrolyl, piperidinyl, morpholinyl and 8-oxo-3-aza-bicyclo[3.2.1]oct-3-yl are optionally substituted, independently, with 1-3 substituents of $R^9$, in conjunction with any of the above or below embodiments.

In another embodiment, the invention includes compounds wherein $R^2$ is $C_{2-4}$alkynyl, —$OC_{1-6}$alkyl, pyridyl, pyrimidyl, dihydropyranyl, tetrahydropyranyl, pyrrolidinyl, tetrahydropyrroly or piperidinyl, wherein the $C_{2-4}$alkynyl, —$OC_{1-6}$alkyl, pyridyl, pyrimidyl, dihydropyranyl, tetrahydropyranyl, pyrrolidinyl, tetrahydropyrroly and piperidinyl are optionally substituted, independently, with 1-3 substituents of $R^9$, in conjunction with any of the above or below embodiments.

In another embodiment, the invention includes compounds wherein $R^2$ is $C_{2-4}$alkynyl, —$OC_{1-6}$alkyl, pyridyl, dihydropyranyl, pyrrolidinyl, tetrahydropyrrolyl or piperidinyl, wherein the $C_{2-4}$alkynyl, —$OC_{1-6}$alkyl, pyridyl, dihydropyranyl, pyrrolidinyl, tetrahydropyrrolyl and piperidinyl are optionally substituted, independently, with 1-3 substituents of $R^9$, in conjunction with any of the above or below embodiments.

In another embodiment, the invention includes compounds wherein $R^2$ is $C_{1-6}$-alkyl, $C_{2-4}$alkenyl, $C_{2-4}$alkynyl, CN, —$OC_{1-6}$alkyl, —$SC_{1-6}$alkyl, —$NHC_{1-6}$alkyl, —$N(C_{1-3}$alkyl$)_2$, —NH-phenyl or —NH-benzyl, wherein the $C_{1-6}$-alkyl, $C_{2-4}$alkenyl, $C_{2-4}$alkynyl, CN, —$OC_{1-6}$alkyl, —$SC_{1-6}$alkyl, —$NHC_{1-6}$alkyl, —$N(C_{1-3}$alkyl$)_2$, —NH-phenyl and —NH-benzyl are optionally substituted, independently, with 1-3 substituents of $R^9$, in conjunction with any of the above or below embodiments.

In another embodiment, the invention includes compounds wherein $R^2$ is halo, haloalkyl, haloalkoxyl, $C_{1-6}$-alkyl, $C_{2-4}$alkenyl, $C_{2-4}$alkynyl, or a ring selected from phenyl, pyridyl, pyrimidyl, pyrazinyl, pyridazinyl, pyrazolyl, isoxazolyl, thiazolyl, pyranyl, dihydropyranyl, tetrahydropyranyl, furanyl, dihydropyranyl, tetrahydrofuranyl, pyrrolyl, pyrrolidinyl, tetrahydropyrrolyl, piperidinyl, piperazinyl, morpholinyl, azetidinyl, 8-oxo-3-aza-bicyclo[3.2.1]oct-3-yl, aza-bicyclo[2.2.1]hept-5-yl, 2-oxo-7-aza-[3,5]-spironon-7-yl, cyclobutyl, cyclopentyl or cyclohexyl, wherein the $C_{1-6}$-alkyl, $C_{2-4}$alkenyl, $C_{2-4}$alkynyl and ring are optionally substituted, independently, with 1-3 substituents of $R^9$, in conjunction with any of the above or below embodiments.

In another embodiment, the invention includes compounds wherein $R^3$ is H, halo, haloalkyl, haloalkoxyl, $C_{1-6}$-alkyl, CN, OH, $OC_{1-6}$-alkyl, $S(O)_o C_{1-6}$-alkyl, $NHC_{1-6}$-alkyl or $C(O)C_{1-6}$-alkyl, in conjunction with any of the above or below embodiments.

In another embodiment, the invention includes compounds wherein $R^3$ is H, F, Cl, Br, $CF_3$, $OCF_3$, $C_{1-6}$-alkyl, CN, OH, —$OC_{1-6}$-alkyl, —$S(O)_o C_{1-6}$-alkyl, —$NHC_{1-6}$-alkyl or —$C(O)C_{1-6}$-alkyl, wherein the $C_{1-6}$-alkyl and $C_{1-6}$-alkyl portion of —$OC_{1-6}$-alkyl, —$S(O)_o C_{1-6}$-alkyl, —$NHC_{1-6}$-alkyl and —$C(O)C_{1-6}$-alkyl are optionally substituted with 1-3 substituents of F, oxo or OH, in conjunction with any of the above or below embodiments.

In another embodiment, the invention includes compounds wherein $R^3$ is H, F, Cl, $CF_3$, $OCF_3$, methyl, ethyl, CN, OH, $OCH_3$, $SCH_3$, $NHCH_3$ or $C(O)CH_3$, in conjunction with any of the above or below embodiments.

In another embodiment, the invention includes compounds wherein $R^3$ is H, F, methyl, CN or OH, in conjunction with any of the above or below embodiments.

In another embodiment, the invention includes compounds wherein $R^3$ is H or F, in conjunction with any of the above or below embodiments.

In another embodiment, the invention includes compounds wherein $R^3$ is H, in conjunction with any of the above or below embodiments.

In another embodiment, the invention includes compounds wherein $R^4$ is H, F, Cl, Br, $CF_3$, $OCF_3$, $C_{1-6}$-alkyl, CN, OH, —$OC_{1-6}$-alkyl, —$S(O)_o C_{1-6}$-alkyl, —$NHC_{1-6}$-alkyl or —$C(O)C_{1-6}$-alkyl, wherein the $C_{1-6}$-alkyl and $C_{1-6}$-alkyl portion of —$OC_{1-6}$-alkyl, —$S(O)_o C_{1-6}$-alkyl, —$NHC_{1-6}$-alkyl and —$C(O)C_{1-6}$-alkyl are optionally substituted with 1-3 substituents of F, oxo or OH, in conjunction with any of the above or below embodiments.

In another embodiment, the invention includes compounds wherein $R^4$ is H, F, Cl, $CF_3$, $OCF_3$, methyl, ethyl, CN, OH, $OCH_3$, $SCH_3$, $NHCH_3$ or $C(O)CH_3$, in conjunction with any of the above or below embodiments.

In another embodiment, the invention includes compounds wherein $R^4$ is H, F, methyl, CN or OH, in conjunction with any of the above or below embodiments.

In another embodiment, the invention includes compounds wherein $R^4$ is H or F, in conjunction with any of the above or below embodiments.

In another embodiment, the invention includes compounds wherein $R^4$ is H, in conjunction with any of the above or below embodiments.

In another embodiment, the invention includes compounds wherein $R^5$ is H, F, Cl, Br, $CF_3$, $OCF_3$, $C_{1-6}$-alkyl, CN, OH, —$OC_{1-6}$-alkyl, —$S(O)_o C_{1-6}$-alkyl, —$NHC_{1-6}$-alkyl or —$C(O)C_{1-6}$-alkyl, wherein the $C_{1-6}$-alkyl and $C_{1-6}$-alkyl portion of —$OC_{1-6}$-alkyl, —$S(O)_o C_{1-6}$-alkyl, —$NHC_{1-6}$-alkyl and —$C(O)C_{1-6}$-alkyl are optionally substituted with 1-3 substituents of F, oxo or OH, in conjunction with any of the above or below embodiments.

In another embodiment, the invention includes compounds wherein $R^5$ is H, F, Cl, $CF_3$, $OCF_3$, methyl, ethyl, CN, OH, $OCH_3$, $SCH_3$, $NHCH_3$ or $C(O)CH_3$, in conjunction with any of the above or below embodiments.

In another embodiment, the invention includes compounds wherein $R^5$ is H, F, methyl, CN or OH, in conjunction with any of the above or below embodiments.

In another embodiment, the invention includes compounds wherein $R^5$ is H or F, in conjunction with any of the above or below embodiments.

In another embodiment, the invention includes compounds wherein $R^5$ is H, in conjunction with any of the above or below embodiments.

In another embodiment, the invention includes compounds wherein $R^6$ is H, halo, haloalkyl, haloalkoxyl, $C_{1-6}$-alkyl, CN, OH, $OC_{1-6}$-alkyl, $S(O)_o C_{1-6}$-alkyl, $NHC_{1-6}$-alkyl or $C(O)C_{1-6}$-alkyl, in conjunction with any of the above or below embodiments.

In another embodiment, the invention includes compounds wherein $R^6$ is H, F, Cl, Br, $CF_3$, $OCF_3$, $C_{1-6}$-alkyl, CN, OH, —$OC_{1-6}$-alkyl, —$S(O)_oC_{1-6}$-alkyl, —$NHC_{1-6}$-alkyl or —$C(O)C_{1-6}$-alkyl, wherein the $C_{1-6}$-alkyl and $C_{1-6}$-alkyl portion of —$OC_{1-6}$-alkyl, —$S(O)_oC_{1-6}$-alkyl, —$NHC_{1-6}$-alkyl and —$C(O)C_{1-6}$-alkyl are optionally substituted with 1-3 substituents of F, oxo or OH, in conjunction with any of the above or below embodiments.

In another embodiment, the invention includes compounds wherein $R^6$ is H, F, Cl, Br, $CF_3$, $OCF_3$, methyl, ethyl, CN, OH, $OCH_3$, $SCH_3$, $NHCH_3$ or $C(O)CH_3$, in conjunction with any of the above or below embodiments.

In another embodiment, the invention includes compounds wherein $R^6$ is H, F, methyl, CN or OH, in conjunction with any of the above or below embodiments.

In another embodiment, the invention includes compounds wherein $R^6$ is H or F, in conjunction with any of the above or below embodiments.

In another embodiment, the invention includes compounds wherein $R^6$ is H, in conjunction with any of the above or below embodiments.

In another embodiment, the invention includes compounds wherein $R^7$ is Cl, Br, $C_{1-6}$-alkyl, $C_{2-4}$alkenyl, $C_{2-4}$alkynyl, CN, —$OC_{1-6}$alkyl, —$SC_{1-6}$alkyl, —$NHC_{1-6}$alkyl, —$N(C_{1-3}$alkyl$)_2$, —$NHC(=O)R^9$, —$C(=O)NHR^9$, —$NHS(O)_2R^9$, —$S(O)_2NHR^9$, —NH-phenyl, —NH-benzyl, phenyl, pyridyl, pyrimidyl, pyrazinyl, pyridazinyl, pyrazolyl, isoxazolyl, thiazolyl, pyranyl, dihydropyranyl, tetrahydropyranyl, furanyl, dihydrofuranyl, tetrahydrofuranyl, pyrrolidinyl, piperidinyl, piperazinyl, morpholinyl, azetidinyl, 8-oxo-3-aza-bicyclo[3.2.1]oct-3-yl, aza-bicyclo[2.2.1]hept-5-yl, 2-oxo-7-aza-[3,5]-spironon-7-yl, cyclopentyl or cyclohexyl, wherein the $C_{1-6}$-alkyl, $C_{2-4}$alkenyl, $C_{2-4}$alkynyl, —$OC_{1-6}$alkyl, —$SC_{1-6}$alkyl, —$NHC_{1-6}$alkyl, —$N(C_{1-3}$alkyl$)_2$, —$NHC(=O)R^9$, —$C(=O)NHR^9$, —$NHS(O)_2R^9$, —$S(O)_2NHR^9$, —NH-phenyl, —NH-benzyl, phenyl, pyridyl, pyrimidyl, pyrazinyl, pyridazinyl, pyrazolyl, isoxazolyl, thiazolyl, pyranyl, dihydropyranyl, tetrahydropyranyl, furanyl, dihydrofuranyl, tetrahydrofuranyl, pyrrolidinyl, piperidinyl, piperazinyl, morpholinyl, azetidinyl, 8-oxo-3-aza-bicyclo[3.2.1]oct-3-yl, aza-bicyclo[2.2.1]hept-5-yl, 2-oxo-7-aza-[3,5]-spironon-7-yl, cyclopentyl and cyclohexyl are optionally substituted, independently, with 1-5 substituents of $R^9$, in conjunction with any of the above or below embodiments.

In another embodiment, the invention includes compounds wherein $R^7$ is Cl, Br, $C_{1-6}$-alkyl, $C_{2-4}$alkenyl, $C_{2-4}$alkynyl, CN, —$OC_{1-6}$alkyl, —$SC_{1-6}$alkyl, —$NHC_{1-6}$alkyl, —$N(C_{1-3}$alkyl$)_2$, —NH-phenyl, —NH-benzyl, phenyl, pyridyl, pyrimidyl, pyrazinyl, pyridazinyl, pyrazolyl, isoxazolyl, thiazolyl, pyranyl, dihydropyranyl, tetrahydropyranyl, furanyl, dihydrofuranyl, tetrahydrofuranyl, pyrrolidinyl, piperidinyl, piperazinyl, morpholinyl, azetidinyl, 8-oxo-3-aza-bicyclo[3.2.1]oct-3-yl, aza-bicyclo[2.2.1]hept-5-yl, 2-oxo-7-aza-[3,5]-spironon-7-yl, cyclopentyl or cyclohexyl, wherein the $C_{1-6}$-alkyl, $C_{2-4}$alkenyl, $C_{2-4}$alkynyl, —$OC_{1-6}$alkyl, —$SC_{1-6}$alkyl, —$NHC_{1-6}$alkyl, —$N(C_{1-3}$alkyl$)_2$, —NH-phenyl, —NH-benzyl, phenyl, pyridyl, pyrimidyl, pyrazinyl, pyridazinyl, pyrazolyl, isoxazolyl, thiazolyl, pyranyl, dihydropyranyl, tetrahydropyranyl, furanyl, dihydrofuranyl, tetrahydrofuranyl, pyrrolidinyl, piperidinyl, piperazinyl, morpholinyl, azetidinyl, 8-oxo-3-aza-bicyclo[3.2.1]oct-3-yl, aza-bicyclo[2.2.1]hept-5-yl, 2-oxo-7-aza-[3,5]-spironon-7-yl, cyclopentyl and cyclohexyl are optionally substituted, independently, with 1-5 substituents of $R^9$, in conjunction with any of the above or below embodiments.

In another embodiment, the invention includes compounds wherein $R^7$ is phenyl, pyridyl, pyrimidyl, pyrazinyl, pyridazinyl, pyrazolyl, isoxazolyl, thiazolyl, pyranyl, dihydropyranyl, tetrahydropyranyl, furanyl, dihydrofuranyl, tetrahydrofuranyl, pyrrolyl, pyrrolidinyl, tetrahydropyrrolyl, piperidinyl, piperazinyl, morpholinyl, azetidinyl, 8-oxo-3-aza-bicyclo[3.2.1]oct-3-yl, aza-bicyclo[2.2.1]hept-5-yl, 2-oxo-7-aza-[3,5]-spironon-7-yl, cyclopentyl, cyclohexyl or —$Si(CH_3)_3$, wherein the phenyl, pyridyl, pyrimidyl, pyrazinyl; pyridazinyl, pyrazolyl, isoxazolyl, thiazolyl, pyranyl, dihydropyranyl, tetrahydropyranyl, furanyl, dihydrofuranyl, tetrahydrofuranyl, pyrrolidinyl, tetrahydropyrrolyl, piperidinyl, piperazinyl, morpholinyl, azetidinyl, 8-oxo-3-aza-bicyclo[3.2.1]oct-3-yl, aza-bicyclo[2.2.1]hept-5-yl, 2-oxo-7-aza-[3,5]-spironon-7-yl, cyclopentyl and cyclohexyl are optionally substituted, independently, with 1-3 substituents of $R^9$, in conjunction with any of the above or below embodiments.

In another embodiment, the invention includes compounds wherein $R^7$ is $C_{2-4}$alkynyl, —$OC_{1-6}$alkyl, —$NHC(=O)R^9$, —$C(=O)NHR^9$, —$NHS(O)_2R^9$, —$S(O)_2NHR^9$, phenyl, pyridyl, pyrimidyl, pyrazinyl or pyridazinyl, wherein the $C_{2-4}$alkynyl, —$OC_{1-6}$alkyl, —$NHC(=O)R^9$, —$C(=O)NHR^9$, —$NHS(O)_2R^9$, —$S(O)_2NHR^9$, phenyl, pyridyl, pyrimidyl, pyrazinyl and pyridazinyl are optionally substituted, independently, with 1-3 substituents of $R^9$, in conjunction with any of the above or below embodiments.

In another embodiment, the invention includes compounds wherein $R^7$ is $C_{2-4}$alkynyl, —$OC_{1-6}$alkyl, phenyl, pyridyl, pyrimidyl, pyrazinyl or pyridazinyl, wherein the $C_{2-4}$alkynyl, —$OC_{1-6}$alkyl, phenyl, pyridyl, pyrimidyl, pyrazinyl and pyridazinyl are optionally substituted, independently, with 1-3 substituents of $R^9$, in conjunction with any of the above or below embodiments.

In another embodiment, the invention includes compounds wherein $R^7$ is $C_{2-4}$alkynyl, —$OC_{1-6}$alkyl, phenyl, 3-pyridyl, 5-pyrimidyl, pyrazinyl or 2-pyridazinyl, wherein the $C_{2-4}$alkynyl, —$OC_{1-6}$alkyl, 3-pyridyl, 5-pyrimidyl, pyrazinyl and 2-pyridazinyl are optionally substituted, independently, with 1-3 substituents of $R^9$, in conjunction with any of the above or below embodiments.

In another embodiment, the invention includes compounds wherein $R^7$ is a ring selected from phenyl, pyridyl, pyrimidyl, pyrazinyl, pyridazinyl, pyrazolyl, isoxazolyl, thiazolyl, pyranyl, dihydropyranyl, tetrahydropyranyl, furanyl, dihydropyranyl, tetrahydrofuranyl, pyrrolidinyl, piperidinyl, piperazinyl, morpholinyl, said ring optionally substituted, independently, with 1-3 substituents of $R^9$, in conjunction with any of the above or below embodiments.

In another embodiment, the invention includes compounds wherein $R^7$ is a ring selected from phenyl, 3-pyridyl, 5-pyrimidyl or 2-pyridazinyl, said ring optionally substituted, independently, with 1-5 substituents of $R^9$, in conjunction with any of the above or below embodiments.

In another embodiment, the invention includes compounds wherein $R^7$ is phenyl, 3-pyridyl, 5-pyrimidyl or 2-pyridazinyl, each of which is optionally substituted with 1-5 substituents of F, Cl, Br, I, CN, $CF_3$, $C_2F_5$, haloalkoxyl, $C_{1-6}$-alkyl, CN, OH, $OC_{1-6}$-alkyl, $SC_{1-6}$-alkyl, oxetanyl or $C_{2-3}$alkynyl, in conjunction with any of the above or below embodiments.

In another embodiment, the invention includes compounds wherein $R^8$ is H, halo, haloalkyl, haloalkoxyl, $C_{1-6}$-alkyl, CN, OH, $OC_{1-6}$-alkyl, $S(O)_oC_{1-6}$-alkyl, $NHC_{1-6}$-alkyl or $C(O)C_{1-6}$-alkyl, in conjunction with any of the above or below embodiments.

In another embodiment, the invention includes compounds wherein $R^8$ is H, F, Cl, Br, $CF_3$, $OCF_3$, $C_{1-6}$-alkyl, CN, OH, —OC$_{1-6}$-alkyl, —S(O)$_o$C$_{1-6}$alkyl, —NHC$_{1-6}$alkyl or —C(O)C$_{1-6}$-alkyl, wherein the C$_{1-6}$-alkyl and C$_{1-6}$-alkyl portion of —OC$_{1-6}$-alkyl, —S(O)$_o$C$_{1-6}$-alkyl, —NHC$_{1-6}$-alkyl and —C(O)C$_{1-6}$-alkyl are optionally substituted with 1-3 substituents of F, oxo or OH, in conjunction with any of the above or below embodiments.

In another embodiment, the invention includes compounds wherein R$^8$ is H, F, Cl, CF$_3$, OCF$_3$, methyl, ethyl, CN, OH, OCH$_3$, SCH$_3$, NHCH$_3$ or C(O)CH$_3$, in conjunction with any of the above or below embodiments.

In another embodiment, the invention includes compounds wherein R$^8$ is H, F, methyl, CN or OH, in conjunction with any of the above or below embodiments.

In another embodiment, the invention includes compounds wherein R$^8$ is H or F, in conjunction with any of the above or below embodiments.

In another embodiment, the invention includes compounds wherein R$^8$ is H, in conjunction with any of the above or below embodiments.

In another embodiment, the invention includes compounds wherein each R$^1$, R$^4$, R$^5$ and R$^8$, independently, is F, Cl, CF$_3$, OCF$_3$, methyl, CN, OH, OCH$_3$, SCH$_3$, NHCH$_3$, oxetanyl or C$_{2-3}$alkynyl, in conjunction with any of the above or below embodiments.

In another embodiment, the invention includes compounds wherein each R$^9$, independently, is F, CF$_3$, CN, CH$_3$, —OCH$_3$, —SCH$_3$, —NHCH$_3$, oxetanyl or C$_{2-3}$alkynyl, in conjunction with any of the above or below embodiments.

In another embodiment, the invention includes compounds wherein each R$^9$, independently, is H, F, methyl, CN, OH, oxetanyl or C$_{2-3}$alkynyl, in conjunction with any of the above or below embodiments.

In another embodiment, the invention includes compounds wherein each R$^9$, independently, is H, C$_{1-6}$-alkyl, CN, —S(O)$_o$C$_{1-6}$-alkyl, —NHC$_{1-6}$ alkyl, —C(O)C$_{1-6}$-alkyl or benzyl, wherein the C$_{1-6}$-alkyl and C$_{1-6}$-alkyl portion of —OC$_{1-6}$-alkyl, —S(O)$_o$C$_{1-6}$-alkyl, or NHC$_{1-6}$-alkyl and —C(O)C$_{1-6}$-alkyl are optionally substituted with 1-3 substituents of F, oxo or OH, in conjunction with any of the above or below embodiments.

In another embodiment, the invention includes compounds wherein each R$^9$, independently, is H, F, CF$_3$, CN, CH$_3$, —OCH$_3$, —SCH$_3$, —NHCH$_3$, oxetanyl or C$_{2-3}$alkynyl, in conjunction with any of the above or below embodiments.

In another embodiment, the invention includes compounds wherein each R$^9$, independently, is halo, haloalkyl, CN, OH, NO$_2$, NH$_2$, acetyl, —C(O)NHCH$_3$, oxo, C$_{1-6}$alkyl, C$_{2-6}$alkenyl, C$_{2-6}$alkynyl, C$_{3-6}$cycloalkyl, C$_{1-6}$alkylamino-, C$_{1-6}$alkoxyl, C$_{1-6}$thioalkoxyl, phenyl, pyridyl, pyrimidyl, pyrazinyl, pyridazinyl, pyrazolyl, isoxazolyl, thiazolyl, morpholinyl, pyrazolyl, isoxazolyl, dihydropyranyl, pyrrolyl, pyrrolidinyl, tetrahydropyrrolyl, piperazinyl, oxetanyl or dioxolyl, wherein each of the C$_{1-6}$alkyl, C$_{2-6}$alkenyl, C$_{2-6}$alkynyl, C$_{3-6}$cycloalkyl, C$_{1-6}$alkylamino-, C$_{1-6}$dialkylamino-, C$_{1-6}$alkoxyl, C$_{1-6}$thioalkoxyl, phenyl, pyridyl, pyrimidyl, pyrazinyl, pyridazinyl, pyrazolyl, isoxazolyl, thiazolyl, morpholinyl, pyrazolyl, isoxazolyl, dihydropyranyl, pyrrolidinyl, oxetanyl or dioxolyl, is optionally substituted independently with 1-5 substituents of F, Cl, CN, NO$_2$, NH$_2$, OH, oxo, methyl, methoxyl, ethyl, ethoxyl, propyl, propoxyl, isopropyl, isopropoxyl, cyclopropyl, cyclopropylmethoxyl, butyl, butoxyl, isobutoxyl, tert-butoxyl, isobutyl, sec-butyl, tert-butyl, C$_{1-3}$alkylamino-, C$_{1-3}$dialkylamino, C$_{1-3}$thioalkoxyl, or oxetanyl, in conjunction with any of the above or below embodiments.

In another embodiment, the invention includes compounds wherein each R$^{10}$, independently, is H, F, Cl, Br, CF$_3$, OCF$_3$, C$_{1-6}$-alkyl, CN, OH, —OC$_{1-6}$-alkyl, —S(O)$_o$C$_{1-6}$-alkyl, —NHC$_{1-6}$-alkyl or —C(O)C$_{1-6}$-alkyl, wherein the C$_{1-6}$-alkyl and C$_{1-6}$-alkyl portion of —OC$_{1-6}$-alkyl, —S(O)$_o$C$_{1-6}$-alkyl, —NHC$_{1-6}$-alkyl and —C(O)C$_{1-6}$-alkyl are optionally substituted with 1-3 substituents of F, oxo or OH, in conjunction with any of the above or below embodiments.

In another embodiment, the invention includes compounds wherein each R$^{10}$, independently, is H, F, Cl, Br, CF$_3$, OCF$_3$, C$_{1-6}$-alkyl, CN, OH, —OC$_{1-3}$-alkyl, —S(O)$_o$C$_{1-3}$-alkyl, or —NHC$_{1-3}$-alkyl, in conjunction with any of the above or below embodiments.

In another embodiment, the invention includes compounds wherein each R$^{10}$, independently, is H, F, Cl, CF$_3$, OCF$_3$, methyl, ethyl, CN, OH, OCH$_3$, SCH$_3$, NHCH$_3$ or C(O)CH$_3$, in conjunction with any of the above or below embodiments.

In another embodiment, the invention includes compounds wherein each R$^{10}$, independently, is H, F, CF$_3$, OCF$_3$, methyl, CN, OCH$_3$, SCH$_3$ or NHCH$_3$, in conjunction with any of the above or below embodiments.

In another embodiment the invention includes compounds wherein —X—Y—Z— taken together is —CR$^{10}$R$^{10}$—CR$^{10}$R$^{10}$—CR$^{10}$R$^{10}$, in conjunction with any of the above or below embodiments.

In another embodiment, the invention includes compounds wherein —X—Y—Z— taken together is —CH$_2$—CR$^{10}$R$^{10}$—CH$_2$ wherein each R$^{10}$ is, independently, H, F, C$_{1-4}$alkyl, OCH$_3$, OH, CN or CF$_3$, in conjunction with any of the above or below embodiments.

In another embodiment, the invention includes compounds wherein —X—Y—Z— taken together is —CH$_2$—CF$_2$—CH$_2$, in conjunction with any of the above or below embodiments.

In another embodiment, the invention includes compounds wherein Z— is absent and —X—Y— taken together is —CR$^{10}$R$^{10}$—CR$^{10}$R$^{10}$, —CR$^{10}$=CR$^{10}$—, —NR$^{11}$—CHR$^{10}$— or —CHR$^{10}$—NR$^{11}$—, wherein each R$^{10}$, independently, is H, F, Cl, Br, CF$_3$, OCF$_3$, C$_{1-6}$-alkyl, CN, OH, —OC$_{1-6}$-alkyl, —S(O)$_o$C$_{1-6}$-alkyl, —NHC$_{1-6}$-alkyl or —C(O)C$_{1-6}$-alkyl, wherein the C$_{1-6}$-alkyl and C$_{1-6}$-alkyl portion of —OC$_{1-6}$-alkyl, —S(O)$_o$C$_{1-6}$-alkyl, —NHC$_{1-6}$-alkyl and —C(O)C$_{1-6}$-alkyl are optionally substituted with 1-3 substituents of F, oxo or OH; and each R$^{11}$, independently, is H, C$_{1-6}$-alkyl or CN, in conjunction with any of the above or below embodiments.

In another embodiment, the invention includes compounds wherein Z— is absent and —X—Y— taken together is —CR$^{10}$R$^{10}$—CR$^{10}$R$^{10}$ or —CR$^{10}$=R$^{10}$—, wherein each R$^{10}$, independently, is H, F, Cl, Br, CF$_3$, OCF$_3$, C$_{1-6}$-alkyl, CN, OH, —OC$_{1-6}$-alkyl, —S(O)$_o$C$_{1-6}$-alkyl, —NHC$_{1-6}$-alkyl or —C(O)C$_{1-6}$-alkyl, wherein the C$_{1-6}$-alkyl and C$_{1-6}$-alkyl portion of —OC$_{1-6}$-alkyl, —S(O)$_o$C$_{1-6}$-alkyl, —NHC$_{1-6}$-alkyl and —C(O)C$_{1-6}$-alkyl are optionally substituted with 1-3 substituents of F, oxo or OH, in conjunction with any of the above or below embodiments.

In another embodiment, the invention includes compounds wherein each R$^{10}$, independently, is H, F, CF$_3$, OCF$_3$, methyl, CN, OCH$_3$, SCH$_3$ or NHCH$_3$, in conjunction with any of the above or below embodiments.

In another embodiment, the invention includes compounds wherein each R$^{10}$, independently, is H, F, CF$_3$, OCF$_3$, methyl, CN, OCH$_3$, SCH$_3$ or NHCH$_3$, in conjunction with any of the above or below embodiments.

In another embodiment of the present invention, the compounds, and solvates, hydrates, tautomers, stereoisomers and pharmaceutically acceptable salts thereof, are defined by Formula I, wherein each of $R^1$, $R^4$, $R^5$ and $R^8$, independently, is H, F, Cl, $CF_3$, $OCF_3$, methyl, ethyl, CN, OH, $OCH_3$, $SCH_3$, $NHCH_3$ or $C(O)CH_3$;

one of $R^2$ and $R^7$, independently, is phenyl, pyridyl, pyrimidyl, pyrazinyl, pyridazinyl, pyrazolyl, isoxazolyl, thiazolyl, pyranyl, dihydropyranyl, tetrahydropyranyl, furanyl, dihydrofuranyl, tetrahydrofuranyl, pyrrolyl, pyrrolidinyl, tetrahydropyrrolyl, piperidinyl, piperazinyl, morpholinyl, azetidinyl, 8-oxo-3-aza-bicyclo[3.2.1]oct-3-yl, aza-bicyclo[2.2.1]hept-5-yl, 2-oxo-7-aza-[3,5]-spironon-7-yl, cyclopentyl, cyclohexyl or $-Si(CH_3)_3$, wherein the phenyl, pyridyl, pyrimidyl, pyrazinyl, pyridazinyl, pyrazolyl, isoxazolyl, thiazolyl, pyranyl, dihydropyranyl, tetrahydropyranyl, furanyl, dihydrofuranyl, tetrahydrofuranyl, pyrrolidinyl, piperidinyl, piperazinyl, morpholinyl, azetidinyl, 8-oxo-3-aza-bicyclo[3.2.1]oct-3-yl, aza-bicyclo[2.2.1]hept-5-yl, 2-oxo-7-aza-[3,5]-spironon-7-yl, cyclopentyl and cyclohexyl are optionally substituted, independently, with 1-3 substituents of $R^9$;

the other of $R^2$ and $R^7$, independently, is $C_{1-6}$-alkyl, $C_{2-4}$alkenyl, $C_{2-4}$alkynyl, CN, $-OC_{1-6}$alkyl, $-SC_{1-6}$alkyl, $-NHC_{1-6}$alkyl, $-N(C_{1-3}$alkyl$)_2$, $-NHC(=O)R^9$, $-C(=O)NHR^9$, $-NHS(O)_2R^9$, $-S(O)_2NHR^9$, $-NH$-phenyl or $-NH$-benzyl, wherein the $C_{1-6}$-alkyl, $C_{2-4}$alkenyl, $C_{2-4}$alkynyl, CN, $-OC_{1-6}$alkyl, $-SC_{1-6}$alkyl, $-NHC_{1-6}$alkyl, $-N(C_{1-3}$alkyl$)_2$, $-NHC(=O)R^9$, $-C(=O)NHR^9$, $-NHS(O)_2R^9$, $-S(O)_2NHR^9$, $-NH$-phenyl and $-NH$-benzyl are optionally substituted, independently, with 1-3 substituents of $R^9$;

each of $R^3$ and $R^6$, independently, is H, halo, haloalkyl, haloalkoxyl, $C_{1-6}$-alkyl, CN, OH, $OC_{1-6}$-alkyl, $SC_{1-6}$-alkyl, $NHC_{1-6}$-alkyl or $C(O)C_{1-6}$-alkyl; and $-X-Y-Z-$ taken together is $-CR^{10}R^{10}-CR^{10}R^{10}-CR^{10}R^{10}-$; or $-Z-$ is absent and $-X-Y-$ taken together is $-CR^{10}R^{10}-CR^{10}R^{10}$, $-CR^{10}=CR^{10}-$, $-NR^{11}-CHR^{10}-$ or $-CHR^{10}-NR^{11}-$, wherein each $R^{10}$, independently, is H, F, Cl, Br, $CF_3$, $OCF_3$, $C_{1-6}$-alkyl, CN, OH, $-OC_{1-6}$-alkyl, $-S(O)_oC_{1-6}$-alkyl, $-NHC_{1-6}$-alkyl or $-C(O)C_{1-6}$-alkyl, wherein the $C_{1-6}$-alkyl and $C_{1-6}$-alkyl portion of $-OC_{1-6}$-alkyl, $-S(O)_oC_{1-6}$-alkyl, $-NHC_{1-6}$-alkyl and $-C(O)C_{1-6}$-alkyl are optionally substituted with 1-3 substituents of F, oxo or OH; and each $R^{11}$, independently, is H, $C_{1-6}$-alkyl or CN, in conjunction with any of the above or below embodiments.

In another embodiment of the present invention, the compounds, and solvates, hydrates, tautomers, stereoisomers and pharmaceutically acceptable salts thereof, are defined by Formula I, wherein $R^2$ is halo, haloalkyl, haloalkoxyl, $C_{1-6}$-alkyl, $C_{2-4}$alkenyl, $C_{2-4}$alkynyl, or a ring selected from phenyl, pyridyl, pyrimidyl, pyrazinyl, pyrazolyl, isoxazolyl, thiazolyl, pyranyl, dihydropyranyl, tetrahydropyranyl, furanyl, dihydrofuranyl, tetrahydrofuranyl, pyrrolyl, pyrrolidinyl, tetrahydropyrrolyl, piperidinyl, piperazinyl, morpholinyl, azetidinyl, 8-oxo-3-aza-bicyclo[3.2.1]oct-3-yl, aza-bicyclo[2.2.1]hept-5-yl, 2-oxo-7-aza-[3,5]-spironon-7-yl, cyclobutyl, cyclopentyl or cyclohexyl, wherein the $C_{1-6}$-alkyl, $C_{2-4}$alkenyl, $C_{2-4}$alkynyl and ring are optionally substituted, independently, with 1-3 substituents of $R^9$;

each of $R^1$, $R^4$, $R^5$ and $R^8$, independently, is H, F, methyl, CN or OH;

each of $R^3$ and $R^6$, independently, is H, F, Cl, $CF_3$, methyl, CN, OH, $OCH_3$, $SCH_3$ or $NHCH_3$;

$R^7$ is a ring selected from phenyl, pyridyl, pyrimidyl, pyridazinyl, pyrazinyl, triazinyl or thiophenyl, said ring optionally substituted, independently, with 1-3 substituents of $R^9$, in conjunction with any of the above or below embodiments.

In another embodiment of the present invention, the compounds, and solvates, hydrates, tautomers, stereoisomers and pharmaceutically acceptable salts thereof, are defined by Formula II, wherein $R^1$ is H or F;
$A^3$ is CH, CF or N;
$A^4$ is CH, CF or N;
$R^5$ is H or F;
$A^6$ is CH, CF or N;
$R^8$ is H or F; and
$-X-Y-$ taken together is $-CR^{10}=CR^{10}-$, wherein each $R^{10}$, independently, is H, F, Cl, Br, $CF_3$, $OCF_3$, $C_{1-6}$-alkyl, CN, OH, $-OC_{1-3}$-alkyl, $-S(O)_oC_{1-3}$-alkyl, or $-NHC_{1-3}$-alkyl, in conjunction with any of the above or below embodiments.

In another embodiment of the present invention, the compounds, and solvates, hydrates, tautomers, stereoisomers and pharmaceutically acceptable salts thereof, are defined by Formula II, wherein each of $R^1$, $R^4$, $R^5$ and $R^8$, independently, is H, F, Cl, $CF_3$, $OCF_3$, methyl, ethyl, CN, OH, $OCH_3$, $SCH_3$, $NHCH_3$ or $C(O)CH_3$;

one of $R^2$ and $R^7$, independently, is phenyl, pyridyl, pyrimidyl, pyrazinyl, pyridazinyl, pyrazolyl, isoxazolyl, thiazolyl, pyranyl, dihydropyranyl, tetrahydropyranyl, furanyl, dihydrofuranyl, tetrahydrofuranyl, pyrrolyl, pyrrolidinyl, tetrahydropyrrolyl, piperidinyl, piperazinyl, morpholinyl, azetidinyl, 8-oxo-3-aza-bicyclo[3.2.1]oct-3-yl, aza-bicyclo[2.2.1]hept-5-yl, 2-oxo-7-aza-[3,5]-spironon-7-yl, cyclopentyl, cyclohexyl or $-Si(CH_3)_3$, wherein the phenyl, pyridyl, pyrimidyl, pyrazinyl, pyridazinyl, pyrazolyl, isoxazolyl, thiazolyl, pyranyl, dihydropyranyl, tetrahydropyranyl, furanyl, dihydrofuranyl, tetrahydrofuranyl, pyrrolidinyl, piperidinyl, piperazinyl, morpholinyl, azetidinyl, 8-oxo-3-aza-bicyclo[3.2.1]oct-3-yl, aza-bicyclo[2.2.1]hept-5-yl, 2-oxo-7-aza-[3,5]-spironon-7-yl, cyclopentyl and cyclohexyl are optionally substituted, independently, with 1-3 substituents of $R^9$;

the other of $R^2$ and $R^7$, independently, is $C_{1-6}$-alkyl, $C_{2-4}$alkenyl, $C_{2-4}$alkynyl, CN, $-OC_{1-6}$alkyl, $-SC_{1-6}$alkyl, $-NHC_{1-6}$alkyl, $-N(C_{1-3}$alkyl$)_2$, $-NHC(=O)R^9$, $-C(=O)NHR^9$, $-NHS(O)_2R^9$, $-S(O)_2NHR^9$, $-NH$-phenyl or $-NH$-benzyl, wherein the $C_{1-6}$-alkyl, $C_{2-4}$alkenyl, $C_{2-4}$alkynyl, CN, $-OC_{1-6}$alkyl, $-SC_{1-6}$ alkyl, $-NHC_{1-6}$alkyl, $-N(C_{1-3}$alkyl$)_2$, $-NHC(=O)R^9$, $-C(=O)NHR^9$, $-NHS(O)_2R^9$, $-S(O)_2NHR^9$, $-NH$-phenyl and $-NH$-benzyl are optionally substituted, independently, with 1-3 substituents of $R^9$;

each of $R^3$ and $R^6$, independently, is H, halo, haloalkyl, haloalkoxyl, $C_{1-6}$-alkyl, CN, OH, $OC_{1-6}$-alkyl, $SC_{1-6}$-alkyl, $NHC_{1-6}$-alkyl or $C(O)C_{1-6}$-alkyl; and each $R^{10}$, independently, is H, F, Cl, $CF_3$, $OCF_3$, methyl, ethyl, CN, OH, $OCH_3$, $SCH_3$, $NHCH_3$ or $C(O)CH_3$, in conjunction with any of the above or below embodiments.

In another embodiment of the present invention, the compounds, and solvates, hydrates, tautomers, stereoisomers and pharmaceutically acceptable salts thereof, are defined by Formula II, wherein $R^2$ is halo, haloalkyl, haloalkoxyl, $C_{1-6}$-alkyl, $C_{2-4}$alkenyl, $C_{2-4}$alkynyl, or a ring selected from phenyl, pyridyl, pyrimidyl, pyrazinyl, pyridazinyl, pyrazolyl, isoxazolyl, thiazolyl, pyranyl, dihydropyranyl, tetrahydropyranyl, furanyl, dihydrofuranyl, tetrahydrofuranyl, pyrrolyl, pyrrolidinyl, tetrahydropyrrolyl, piperidinyl, piperazinyl, morpholinyl, azetidinyl, 8-oxo-3-aza-bicyclo[3.2.1]oct-3-yl, aza-bicyclo[2.2.1]hept-5-yl, 2-oxo-7-aza-[3,5]-spironon-7-yl, cyclobutyl, cyclopentyl or cyclohexyl, wherein the $C_{1-6}$-alkyl, $C_{2-4}$alkenyl, $C_{2-4}$alkynyl and ring are optionally substituted, independently, with 1-3 substituents of $R^9$;

each of $R^1$, $R^4$, $R^5$ and $R^8$, independently, is H, F, methyl, CN or OH;

each of $R^3$ and $R^6$, independently, is H, F, Cl, $CF_3$, methyl, CN, OH, $OCH_3$, $SCH_3$ or $NHCH_3$;

$R^7$ is a ring selected from phenyl, pyridyl, pyrimidyl, pyridazinyl, pyrazinyl, triazinyl or thiophenyl, said ring optionally substituted, independently, with 1-3 substituents of $R^9$; and —X—Y— taken together is —$CHR^{10}$—$CHR^{10}$—, —$CR^{10}$=$CR^{10}$—, —$NR^{11}$—$CHR^{10}$— or —$CHR^{10}$—$NR^{11}$—, wherein each $R^{10}$, independently, is H, F, Cl, Br, $CF_3$, $OCF_3$, $C_{1-6}$-alkyl, CN, OH, —$OC_{1-6}$-alkyl, —$S(O)_o$ $C_{1-6}$-alkyl, —$NHC_{1-6}$-alkyl or —$C(O)C_{1-6}$-alkyl, wherein the $C_{1-6}$-alkyl and $C_{1-6}$-alkyl portion of —$OC_{1-6}$-alkyl, —$S(O)_oC_{1-6}$alkyl, —$NHC_{1-6}$-alkyl and —$C(O)C_{1-6}$-alkyl are optionally substituted with 1-3 substituents of F, oxo or OH; and each $R^{11}$, independently, is H, $C_{1-6}$-alkyl or CN, in conjunction with any of the above or below embodiments.

In another embodiment of the present invention, the compounds, and solvates, hydrates, tautomers, stereoisomers and pharmaceutically acceptable salts thereof, are defined by Formula II, wherein $A^3$ is $CR^3$ or N;

$A^4$ is $CR^4$;

$R^2$ is halo, haloalkyl, haloalkoxyl, $C_{1-6}$-alkyl, $C_{2-4}$alkenyl, $C_{2-4}$alkynyl, or a ring selected from phenyl, pyridyl, pyrimidyl, pyrazinyl, pyridazinyl, pyrazolyl, isoxazolyl, thiazolyl, pyranyl, dihydropyranyl, tetrahydropyranyl, furanyl, dihydropyranyl, tetrahydrofuranyl, pyrrolyl, pyrrolidinyl, tetrahydropyrrolyl, piperidinyl, piperazinyl, morpholinyl, azetidinyl, 8-oxo-3-aza-bicyclo[3.2.1]oct-3-yl, aza-bicyclo[2.2.1]hept-5-yl, 2-oxo-7-m-[3,5]-spironon-7-yl, cyclobutyl, cyclopentyl or cyclohexyl, wherein the $C_{1-6}$-alkyl, $C_{2-4}$alkenyl, $C_{2-4}$alkynyl and ring are optionally substituted, independently, with 1-3 substituents of $R^9$;

each of $R^1$, $R^4$, $R^3$ and $R^8$, independently, is H, F, methyl, CN or OH;

each of $R^3$ and $R^6$, independently, is H, F, Cl, $CF_3$, methyl, CN, OH, $OCH_3$, $SCH_3$ or $NHCH_3$;

$R^7$ is a ring selected from phenyl, pyridyl, pyrimidyl, pyridazinyl, pyrazinyl, triazinyl or thiophenyl, said ring optionally substituted, independently, with 1-3 substituents of $R^9$; and each $R^{10}$, independently, is H, F, Cl, $CF_3$, $OCF_3$, methyl, ethyl, CN, OH, $OCH_3$, $SCH_3$, $NHCH_3$ or $C(O)CH_3$, and each $R^{11}$ is H or $CH_3$, in conjunction with any of the above or below embodiments.

In another embodiment of the present invention, the compounds, and solvates, hydrates, tautomers, stereoisomers and pharmaceutically acceptable salts thereof, are defined by Formula III, wherein $A^3$ is $CR^3$;

$A^4$ is $CR^4$ or N;

$R^2$ is halo, haloalkyl, haloalkoxyl, $C_{1-6}$-alkyl, $C_{2-4}$alkenyl, $C_{2-4}$alkynyl, or a ring selected from phenyl, pyridyl, pyrimidyl, pyrazinyl, pyridazinyl, pyrazolyl, isoxazolyl, thiazolyl, pyranyl, dihydropyranyl, tetrahydropyranyl, furanyl, dihydropyranyl, tetrahydrofuranyl, pyrrolyl, pyrrolidinyl, tetrahydropyrrolyl, piperidinyl, piperazinyl, morpholinyl, azetidinyl, 8-oxo-3-aza-bicyclo[3.2.1]oct-3-yl, aza-bicyclo[2.2.1]hept-5-yl, 2-oxo-7-aza-[3,5]-spironon-7-yl, cyclobutyl, cyclopentyl or cyclohexyl, wherein the $C_{1-6}$-alkyl, $C_{2-4}$alkenyl, $C_{2-4}$alkynyl and ring are optionally substituted, independently, with 1-3 substituents of $R^9$;

each of $R^1$, $R^4$, $R^5$ and $R^8$, independently; is H, F, methyl, CN or OH;

each of $R^3$ and $R^6$, independently, is H, F, Cl, $CF_3$, methyl, CN, OH, $OCH_3$, $SCH_3$ or $NHCH_3$;

$R^7$ is a ring selected from phenyl, pyridyl, pyrimidyl, pyridazinyl, pyrazinyl, triazinyl or thiophenyl, said ring optionally substituted, independently, with 1-3 substituents of $R^9$; and each $R^{10}$, independently, is H, F, Cl, $CF_3$, $OCF_3$, methyl, ethyl, CN, OH, $OCH_3$, $SCH_3$, $NHCH_3$ or $C(O)CH_3$, and each $R^{11}$ is H or $CH_3$, in conjunction with any of the above or below embodiments.

In another embodiment, the invention provides one or more of the compounds, or a pharmaceutically acceptable salt thereof, of Formulas I, II and III, as taught and described herein.

In another embodiment, the invention provides the compound of Formula I, II, II-A, II-B or III, or a stereoisomer or pharmaceutically acceptable salt thereof, selected from 4'-fluoro-7'-(2-fluoro-3-pyridinyl)-2'-methoxyspiro[imidazo[1,5-a]imidazole-7,9'-xanthen]-5-amine;

(7S)-4'-fluoro-7'-(2-fluoro-3-pyridinyl)-2'-(2-fluoro-4-pyridinyl)spiro[imidazo[1,5-a]imidazole-7,9'-xanthen]-5-amine;

(7R)-4'-fluoro-7'-(2-fluoro-3-pyridinyl)-2'-(2-fluoro-4-pyridinyl)spiro[imidazo[1,5-a]imidazole-7,9'-xanthen]-5-amine;

(7R)-2'-(5,6-dihydro-2H-pyran-3-yl)-4'-fluoro-7'-(2-fluoro-3-pyridinyl)spiro[imidazo[1,5-a]imidazole-7,9'-xanthen]-5-amine;

(7S)-2'-(5,6-dihydro-2H-pyran-3-yl)-4'-fluoro-7'-(2-fluoro-3-pyridinyl)spiro[imidazo[1,5-a]imidazole-7,9'-xanthen]-5-amine;

(7R)-4'-fluoro-7'-(2-fluoro-3-pyridinyl)-2'-(4-methylphenyl)spiro[imidazo[1,5-a]imidazole-7,9'-xanthen]-5-amine;

(7S)-4'-fluoro-7'-(2-fluoro-3-pyridinyl)-2'-(4-methylphenyl)spiro[imidazo[1,5-a]imidazole-7,9'-xanthen]-5-amine;

(7R)-4'-fluoro-7'-(2-fluoro-3-pyridinyl)-2'-(4-morpholinyl)spiro[imidazo[1,5-a]imidazole-7,9'-xanthen]-5-amine;

(7S)-4'-fluoro-7'-(2-fluoro-3-pyridinyl)-2'-(4-morpholinyl)spiro[imidazo[1,5-a]imidazole-7,9'-xanthen]-5-amine;

(7R)-2'-(3,6-dihydro-2H-pyran-4-yl)-4'-fluoro-7'-(2-fluoro-3-pyridinyl)spiro[imidazo[1,5-a]imidazole-7,9'-xanthen]-5-amine;

(7S)-2'-(3,6-dihydro-2H-pyran-4-yl)-4'-fluoro-7'-(2-fluoro-3-pyridinyl)spiro[imidazo[1,5-a]imidazole-7,9'-xanthen]-5-amine;

(7R)-2'-(4,4-difluoro-1-piperidinyl)-4'-fluoro-7'-(2-fluoro-3-pyridinyl)spiro[imidazo[1,5-a]imidazole-7,9'-xanthen]-5-amine;

(7S)-2'-(4,4-difluoro-1-piperidinyl)-4'-fluoro-7'-(2-fluoro-3-pyridinyl)spiro[imidazo[1,5-a]imidazole-7,9'-xanthen]-5-amine;

(7S)-4'-fluoro-7'-(2-fluoropyridin-3-yl)-2'-methoxy-3,4-dihydro-2H-spiro[imidazo[1,5-a]pyrimidine-8,9'-xanthen]-6-amine; and (7R)-4'-fluoro-7'-(2-fluoropyridin-3-yl)-2'-methoxy-3,4-dihydro-2H-spiro[ imidazo[1,5-a]pyrimidine-8,9'-xanthen]-6-amine.

All of the possible embodiments described herein for various of the R, X, Y and Z groups of the compounds of Formula I may be applied, as appropriate, to compounds of Formulas II and III, and any sub-formulas thereof.

In another embodiment, the invention provides each of the Examplary compounds, and stereoisomers, tautomers, solvates, pharmaceutically acceptable salts, derivatives or prodrugs thereof, and related intermediates, described herein.

In another embodiment, the invention provides the exemplified compounds described herein, and pharmaceutically acceptable salt forms of each thereof.

DEFINITIONS

The following definitions should assist in understanding the invention.

The term "comprising" is meant to be open ended, i.e., all encompassing and non-limiting. It may be used herein synonymously with "having." Comprising is intended to include each and every indicated or recited component or element(s) while not excluding any other components or elements.

The term "$C_{\alpha-\beta}$alkyl", when used either alone or within other terms such as "haloalkyl" and "alkylamino", embraces linear or branched radicals having $\alpha$ to $\beta$ number of carbon atoms (such as $C_1$-$C_{10}$; $C_1$-$C_6$; or $C_1$-$C_4$). Unless otherwise specified, one or more carbon atoms of the "alkyl" radical may be substituted, such as with a cycloalkyl moiety. Examples of "alkyl" radicals include methyl, cyclopropylmethyl, cyclobutylmethyl, cyclopentylmethyl, ethyl, cyclopropylethyl, cyclobutylethyl, cyclopentylethyl, n-propyl, isopropyl, n-butyl, cyclopropylbutyl, isobutyl, sec-butyl, tert-butyl, pentyl, isoamyl, hexyl and the like.

The term "$C_{\alpha-\beta}$alkenyl", when used alone or in combination, embraces linear or branched radicals having at least one carbon-carbon double bond in a moiety having a number of carbon atoms in the range from $\alpha$ and $\beta$. Included within alkenyl radicals are "lower alkenyl" radicals having two to about six carbon atoms and, for example, those radicals having two to about four carbon atoms. Examples of alkenyl radicals include, without limitation, ethenyl, propenyl, allyl; propenyl, butenyl and 4-methylbutenyl. The terms "alkenyl" and "lower alkenyl", embrace radicals having "cis" and "trans" orientations, or alternatively, "E" and "Z" orientations, as appreciated by those of ordinary skill in the art.

The term "$C_{\alpha-\beta}$alkynyl", when used alone or in combination, denotes linear or branched radicals having at least one carbon-carbon triple bond in a moiety having a number of carbon atoms in the range from $\alpha$ and $\beta$. Examples of alkynyl radicals include "lower alkynyl" radicals having two to about six carbon atoms and, for example, lower alkynyl radicals having two to about four carbon atoms. Examples of such radicals include, without limitation, ethynyl, propynyl (propargyl), butynyl, and the like.

The term "$C_{\alpha-\beta}$alkyl", "$C_{\alpha-\beta}$-alkenyl" and "$C_{\alpha-\beta}$-alkynyl", when used with other terms such as "wherein 1, 2 or 3 carbon atoms of said $C_{\alpha-\beta}$-alkyl, $C_{\alpha-\beta}$-alkenyl or $C_{2\alpha-\beta}$-alkynyl is optionally replaced with a heteroatom selected from O, S, S(O), S(O)$_2$ and N" embraces linear or branched radicals wherein one or more of the carbon atoms may be replaced with a heteroatom. Examples of such "alkyl" radicals include —O-methyl, —O-ethyl, —CH$_2$—O—CH$_3$, —CH$_2$CH$_2$—O—CH$_3$, —NH—CH$_2$, —CH$_2$CH$_2$—N(CH$_3$)—CH$_3$, —S—(CH$_2$)$_3$CH$_2$, —CH$_2$CH$_2$—S—CH$_3$ and the like. Accordingly, such radicals also include radicals encompassed by —OR$^7$ where R$^7$ may be defined as a $C_{\alpha-\beta}$-alkyl. Examples of such "alkenyl" radicals include —NH—CH$_2$CH=CH$_2$, —S—CH$_2$CH$_2$CH=CHCH$_3$ and the like. Similar examples exist for such "alkynyl" radicals, as appreciated by those skilled in the art.

The term "$C_{\alpha-\beta}$alkoxyl" or "—OC$_{\alpha-\beta}$alkyl" when used alone or in combination, embraces linear or branched oxygen-containing alkyl radicals each having $\alpha$ to $\beta$ number of carbon atoms (such as $C_1$-$C_{10}$). The terms "alkoxy" and "alkoxyl", when used alone or in combination, embraces linear or branched oxygen-containing radicals each having alkyl and substituted alkyl portions of one or more carbon atoms. Examples of such radicals include methoxy, ethoxy, propoxy, butoxy, tert-butoxy and neopentoxy. Alkoxy radicals may be further substituted with one or more halo atoms, such as fluoro, chloro or bromo, to provide "haloalkoxy" radicals or with other substitution. Examples of such radicals include fluoromethoxy, chloromethoxy, trifluoromethoxy, trifluoroethoxy, fluoroethoxy and fluoropropoxy.

The term "aryl", when used alone or in combination, means a carbocyclic aromatic moiety containing one, two or even three rings wherein such rings may be attached together in a fused manner. Every ring of an "aryl" multi-ring system need not be aromatic, and the ring(s) fused to the aromatic ring may be partially or fully unsaturated and include one or more heteroatoms selected from nitrogen, oxygen and sulfur. Thus, the term "aryl" embraces aromatic radicals such as phenyl, naphthyl, indenyl, tetrahydronaphthyl, dihydrobenzafuranyl, anthracenyl, indanyl, benzodioxazinyl, and the like. The "aryl" group may be substituted, such as with 1 to 5 substituents including lower alkyl, hydroxyl, halo, haloalkyl, nitro, cyano, alkoxy and lower alkylamino, and the like. Phenyl substituted with —O—CH$_2$—O— or —O—CH$_2$—CH$_2$—O— forms an aryl benzodioxolyl substituent.

The term "$C_{\alpha-\beta}$-cycloalkyl", also referred to herein as "carbocyclic", when used alone or in combination, denotes a partially or fully saturated ring radical having a number of carbon atoms in the range from $\alpha$ and $\beta$. The "cycloalkyl" may contain one ("monocyclic"), two ("bicyclic") or even three ("tricyclic") rings wherein such rings may be attached together in a fused manner and each formed from carbon atoms. Examples of saturated carbocyclic radicals include saturated 3 to 6-membered monocyclic groups such as cyclopropane, cyclobutane, cyclopentane and cyclohexane. Cycloalkyls may be substituted as described herein.

The terms "ring" and "ring system" refer to a ring comprising the delineated number of atoms, the atoms being carbon or, where indicated, a heteroatom such as nitrogen, oxygen or sulfur. Where the number of atoms is not delineated, such as a "monocyclic ring system" or a "bicyclic ring system", the numbers of atoms are 3-8 for a monocyclic and 6-12 for a bicyclic ring. The ring itself, as well as any substitutents thereon, may be attached at any atom that allows a stable compound to be formed. The term "nonaromatic" ring or ring system refers to the fact that at least one, but not necessarily all, rings in a bicyclic or tricyclic ring system is nonaromatic.

The terms "partially or fully saturated or unsaturated" and "saturated or partially or fully unsaturated" with respect to each individual ring, refer to the ring either as fully aromatic (fully unsaturated), partially aromatic (or partially saturated) or fully saturated (containing no double or triple bonds therein). If not specified as such, then it is contemplated that each ring (monocyclic) in a ring system (if bicyclic or tricyclic) may either be fully aromatic, partially aromatic or fully saturated, and optionally substituted with up to 5 substituents. This includes carbocyclics, heterocyclics, aryl and heteroaryl rings.

The term "halo", when used alone or in combination, means halogens such as fluorine, chlorine, bromine or iodine atoms.

The term "haloalkyl", when used alone or in combination, embraces radicals wherein any one or more of the alkyl carbon atoms is substituted with halo as defined above. For example, this term includes monohaloalkyl, dihaloalkyl and polyhaloalkyl radicals such as a perhaloalkyl. A monohaloalkyl radical, for example, may have either an iodo, bromo, chloro or fluoro atom within the radical. Dihalo and polyhaloalkyl radicals may have two or more of the same halo atoms or a combination of different halo radicals. Examples of haloalkyl radicals include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. "Perfluoroalkyl", as used herein, refers to alkyl radicals having all hydrogen atoms replaced with fluoro atoms. Examples include trifluoromethyl and pentafluoroethyl.

The term "heteroaryl", as used herein, either alone or in combination, means a fully unsaturated (aromatic) ring moiety formed from carbon atoms and having one or more heteroatoms selected from nitrogen, oxygen and sulfur. The ring moiety or ring system may contain one ("monocyclic"), two ("bicyclic") or even three ("tricyclic") rings wherein such rings are attached together in a fused manner. Every ring of a "heteroaryl" ring system need not be aromatic, and the ring(s) fused thereto (to the heteroaromatic ring) may be partially or fully saturated and optionally include one or more heteroatoms selected from nitrogen, oxygen and sulfur. The term "heteroaryl" does not include rings having ring members of —O—O—, —O—S— or —S—S—.

Examples of unsaturated heteroaryl radicals, include unsaturated 5- to 6-membered heteromonocyclyl groups containing 1 to 4 nitrogen atoms, including for example, pyrrolyl, imidazolyl, pyrazolyl, 2-pyridyl, 3-pyridyl, 4-pyridyl, pyrimidyl, pyrazinyl, pyridazinyl, triazolyl [e.g., 4H-1,2,4-triazolyl, 1H-1,2,3-triazolyl, 2H-1,2,3-triazolyl] and tetrazole; unsaturated 7- to 10-membered heterobicyclyl groups containing 1 to 4 nitrogen atoms, including for example, quinolinyl, isoquinolinyl, quinazolinyl, isoquinazolinyl, azaquinazolinyl, and the like; unsaturated 5- to 6-membered heteromonocyclic group containing an oxygen atom, for example, pyranyl, 2-furyl, 3-furyl, benzofuryl, etc.; unsaturated 5 to 6-membered heteromonocyclic group containing a sulfur atom, for example, 2-thienyl, 3-thienyl, benzothienyl, etc.; unsaturated 5- to 6-membered heteromonocyclic group containing 1 to 2 oxygen atoms and 1 to 3 nitrogen atoms, for example, oxazolyl, isoxazolyl, oxadiazolyl [e.g., 1,2,4-oxadiazolyl, 1,3,4-oxadiazolyl, 1,2,5-oxadiazolyl]; unsaturated 5 to 6-membered heteromonocyclic group containing 1 to 2 sulfur atoms and 1 to 3 nitrogen atoms, for example, thiazolyl, isothiazolyl, thiadiazolyl [e.g., 1,2,4-thiadiazolyl, 1,3,4-thiadiazolyl, 1,2,5-thiadiazolyl].

The terms "heterocycle" or "heterocyclic", when used alone or in combination, means a partially or fully saturated ring moiety containing one, two or even three rings wherein such rings may be attached together in a fused manner, formed from carbon atoms and including one or more heteroatoms selected from N, O or S. Examples of saturated heterocyclic radicals include saturated 3 to 6-membered heteromonocyclic groups containing 1 to 4 nitrogen atoms [e.g. pyrrolidinyl, imidazolidinyl, piperidinyl, pyrrolinyl, piperazinyl]; saturated 3 to 6-membered heteromonocyclic group containing 1 to 2 oxygen atoms and 1 to 3 nitrogen atoms [e.g. morpholinyl]; saturated 3 to 6-membered heteromonocyclic group containing 1 to 2 sulfur atoms and 1 to 3 nitrogen atoms [e.g., thiazolidinyl]. Examples of partially saturated heterocyclyl radicals include dihydrothienyl, dihydropyranyl, dihydrofuryl and dihydrothiazolyl.

The term "heterocycle" also embraces radicals where heterocyclic radicals are fused/condensed with aryl radicals: unsaturated condensed heterocyclic group containing 1 to 5 nitrogen atoms, for example, indolyl, isoindolyl, indolizinyl, benzimidazolyl, quinolyl, isoquinolyl, indazolyl, benzotriazolyl, tetrazolopyridazinyl [e.g., tetrazolo[1,5-b]pyridazinyl]; unsaturated condensed heterocyclic group containing 1 to 2 oxygen atoms and 1 to 3 nitrogen atoms [e.g. benzoxazolyl, benzoxadiazolyl]; unsaturated condensed heterocyclic group containing 1 to 2 sulfur atoms and 1 to 3 nitrogen atoms [e.g., benzothiazolyl, benzothiadiazolyl]; and saturated, partially unsaturated and unsaturated condensed heterocyclic group containing 1 to 2 oxygen or sulfur atoms [e.g. benzofuryl, benzothienyl, 2,3-dihydro-benzo[1,4]dioxinyl and dihydrobenzofuryl]. Examples of heterocyclic radicals include five to ten membered fused or unfused radicals.

Examples of partially saturated and fully saturated heterocyclyls include, without limitation, pyrrolidinyl, imidazolidinyl, piperidinyl, pyrrolinyl, pyrazolidinyl, piperazinyl, morpholinyl, tetrahydropyranyl, thiazolidinyl, dihydrothienyl, 2,3-dihydro-benzo[1,4]dioxanyl, indolinyl, isoindolinyl, dihydrobenzothienyl, dihydrobenzofuryl, isochromanyl, chromanyl, 1,2-dihydroquinolyl, 1,2,3,4-tetrahydro-isoquinolyl, 1,2,3,4-tetrahydro-quinolyl, 2,3,4,4a,9,9a-hexahydro-1H-3-aza-fluorenyl, 5,6,7-trihydro-1,2,4-triazolo[3,4-a]isoquinolyl, 3,4-dihydro-2H-benzo[1,4]oxazinyl, benzo[1,4]dioxanyl, 2,3-dihydro-1H-1$\lambda'$-benzo[d]isothiazol-6-yl, dihydropyranyl, dihydrofuryl and dihydrothiazolyl, and the like.

The term "a 3-8 membered monocyclic or 6-12 membered bicyclic ring system, said ring system formed of carbon atoms optionally including 1-3 heteroatoms if monocyclic or 1-6 heteroatoms if bicyclic, said heteroatoms selected from O, N, or S, wherein said ring system is optionally substituted" refers to a single ring of 3-, 4-, 5-, 6-, 7- or 8-atom membered or a 6-, 7-, 8-, 9-, 10-, 11 or 12-atom membered bicyclic ring system comprising the delineated number of atoms, the atoms being carbon or, where indicated, a heteroatom such as nitrogen (N), oxygen (O) or sulfur (S). Where the number of atoms is not delineated, such as a "monocyclic ring system" or a "bicyclic ring system", the numbers of atoms are 3-8 for a monocyclic and 6-12 for a bicyclic ring. The ring or ring system may contain substitutents thereon, attached at any atom that allows a stable compound to be formed. A bicyclic ring is intended to include fused ring systems as well as spiro-fused rings. This phrase encompasses carbocyclics, heterocyclics, aryl and heteroaryl rings.

The term "alkylamino" includes "N-alkylamino" where amino radicals are independently substituted with one alkyl radical. Preferred alkylamino radicals are "lower alkylamino" radicals having one to six carbon atoms. Even more preferred are lower alkylamino radicals having one to three carbon atoms. Examples of such lower alkylamino radicals include N-methylamino, and N-ethylamino, N-propylamino, N-isopropylamino and the like.

The term "dialkylamino" includes "N, N-dialkylamino" where amino radicals are independently substituted with two alkyl radicals. Preferred alkylamino radicals are "lower alkylamino" radicals having one to six carbon atoms. Even more preferred are lower alkylamino radicals having one to three carbon atoms. Examples of such lower alkylamino radicals include N,N-dimethylamino, N,N-diethylamino, and the like.

The term "carbonyl", whether used alone or with other terms, such as "aminocarbonyl", denotes —(C=O)—. "Carbonyl" is also used herein synonymously with the term "oxo".

The term "alkylthio" or "thioalkoxy" embraces radicals containing a linear or branched alkyl radical, of one to ten carbon atoms, attached to a divalent sulfur atom. An example of "alkylthio" or "thioalkoxy" is methylthio, ($CH_3S$—).

The term "Formula I" includes any sub formulas, such as Formulas II and III. Similar with Formulas II and III, in that they include sub-formulas where described.

The term "pharmaceutically-acceptable" when used with reference to a compound of Formulas I-III is intended to refer to a form of the compound that is safe for administration. For example, a salt form, a solvate, a hydrate, a prodrug or derivative form of a compound of Formulas I-III, which has been approved for mammalian use, via oral ingestion or other routes of administration, by a governing body or regulatory agency, such as the Food and Drug Administration (FDA) of the United States, is pharmaceutically acceptable.

Included in the compounds of Formulas I-III are the pharmaceutically acceptable salt forms of the free-base compounds. The term "pharmaceutically-acceptable salts" embraces salts commonly used to form alkali metal salts and to form addition salts of free acids or free bases. As appreciated by those of ordinary skill in the art, salts may be formed from ionic associations, charge-charge interactions, covalent bonding, complexation, coordination, etc. The nature of the salt is not critical, provided that it is pharmaceutically acceptable.

Suitable pharmaceutically acceptable acid addition salts of compounds of Formulas I-III may be prepared from an inorganic acid or from an organic acid. Examples of such inorganic acids are hydrochloric, hydrobromic, hydroiodic, hydrofluoric, nitric, carbonic, sulfuric and phosphoric acid. Appropriate organic acids may be selected from aliphatic, cycloaliphatic, aromatic, arylaliphatic, heterocyclic, carboxylic and sulfonic classes of organic acids, examples of which include, without limitation, formic, acetic, adipic, butyric, propionic, succinic, glycolic, gluconic, lactic, malic, tartaric, citric, ascorbic, glucuronic, maleic, fumaric, pyruvic, aspartic, glutamic, benzoic, anthranilic, mesylic, 4-hydroxybenzoic, phenylacetic, mandelic, embonic (pamoic), methanesulfonic, ethanesulfonic, ethanedisulfonic, benzenesulfonic, pantothenic, 2-hydroxyethanesulfonic, toluenesulfonic, sulfanilic, cyclohexylaminosulfonic, camphoric, camphorsulfonic, digluconic, cyclopentanepropionic, dodecylsulfonic, glucoheptanoic, glycerophosphonic, heptanoic, hexanoic, 2-hydroxy-ethanesulfonic, nicotinic, 2-naphthalenesulfonic, oxalic, palmoic, pectinic, persulfuric, 2-phenylpropionic, picric, pivalic propionic, succinic, thiocyanic, undecanoic, stearic, algenic, β-hydroxybutyric, salicylic, galactaric and galacturonic acid. Suitable pharmaceutically-acceptable base addition salts of compounds of Formulas I-III include metallic salts, such as salts made from aluminum, calcium, lithium, magnesium, potassium, sodium and zinc, or salts made from organic bases including, without limitation, primary, secondary and tertiary amines, substituted amines including cyclic amines, such as caffeine, arginine, diethylamine, N-ethyl piperidine, histidine, glucamine, isopropylamine, lysine, morpholine, N-ethyl morpholine, piperazine, piperidine, triethylamine, disopropylethylamine and trimethylamine. All of these salts may be prepared by conventional means from the corresponding compound of the invention by reacting, for example, the appropriate acid or base with the compound of Formulas I-III.

Also, the basic nitrogen-containing groups can be quaternized with such agents as lower alkyl halides, such as methyl, ethyl, propyl, and butyl chloride, bromides and iodides; dialkyl sulfates like dimethyl, diethyl, dibutyl, and diamyl sulfates, long chain halides such as decyl, lauryl, myristyl and stearyl chlorides, bromides and iodides, aralkyl halides like benzyl and phenethyl bromides, and others. Water or oil-soluble or dispersible products are thereby obtained.

Additional examples of such salts can be found in Berge et al., J. Pharm. Sci., 66:1 (1977). Conventional methods may be used to form the salts. For example, a phosphate salt of a compound of the invention may be made by combining the desired compound free base in a desired solvent, or combination of solvents, with phosphoric acid in a desired stoichiometric amount, at a desired temperature, typically under heat (depending upon the boiling point of the solvent). The salt can be precipitated upon cooling (slow or fast) and may crystallize (i.e., if crystalline in nature), as appreciated by those of ordinary skill in the art. Further, hemi-, mono-, di, tri- and poly-salt forms of the compounds of the present invention are also contemplated herein. Similarly, hemi-, mono-, di, tri- and poly-hydrated forms of the compounds, salts and derivatives thereof, are also contemplated herein.

The term "pharmaceutically-acceptable derivative" as used herein, denotes a derivative which is pharmaceutically acceptable.

The compound(s) of Formulas I-III may be used to treat a subject by administering the compound(s) as a pharmaceutical composition. To this end, the compound(s) can be combined with one or more excipients, including without limitation, carriers, diluents or adjuvants to form a suitable composition, which is described in more detail herein.

The term "excipient", as used herein, denotes any pharmaceutically acceptable additive, carrier, adjuvant, or other suitable ingredient, other than the active pharmaceutical ingredient (API), which is typically included for formulation and/or administration purposes. "Diluent" and "adjuvant" are defined hereinafter.

The terms "treat", "treating," "treatment," and "therapy" as used herein refer to therapy, including without limitation, curative therapy, prophylactic therapy, and preventative therapy. Prophylactic treatment generally constitutes either preventing the onset of disorders altogether or delaying the onset of a pre-clinically evident stage of disorders in individuals.

The phrase "effective dosage amount" is intended to quantify the amount of each agent, which will achieve the goal of improvement in disorder severity and the frequency of incidence over treatment of each agent by itself, while avoiding adverse side effects typically associated with alternative therapies. Accordingly, this term is not limited to a single dose, but may comprise multiple dosages required to bring about a therapeutic or prophylactic response in the subject. For example, "effective dosage amount" is not limited to a single capsule or tablet, but may include more than one capsule or tablet, which is the dose prescribed by a qualified physician or medical care giver to the subject.

The term "leaving group" (also denoted as "LG") generally refers to groups that are displaceable by a nucleophile. Such leaving groups are known in the art. Examples of leaving groups include, but are not limited to, halides (e.g., I, Br, F, Cl), sulfonates (e.g., mesylate, tosylate), sulfides (e.g., $SCH_3$), N-hydroxsuccinimide, N-hydroxybenzotriazole, and the like. Nucleophiles are species that are capable of attacking a molecule at the point of attachment of the leaving group causing displacement of the leaving group. Nucleophiles are known in the art. Examples of nucleophilic groups include, but are not limited to, amines, thiols, alcohols, Grignard reagents, anionic species (e.g., alkoxides, amides, carbanions) and the like.

General Synthetic Procedures

The present invention further comprises procedures for the preparation of compounds of Formulas I-III. The compounds of Formulas I-III can be synthesized according to the procedures described in the following Schemes 1, 2, 3a, 3b, 4 and 5, wherein the substituents are as defined for Formulas I-III above, except where further noted. The synthetic methods described below are merely exemplary, and the compounds of the invention may also be synthesized by alternate routes utilizing alternative synthetic strategies, as appreciated by persons of ordinary skill in the art.

The following list of abbreviations used throughout the specification represent the following and should assist in understanding the invention:
ACN, MeCN—acetonitrile
Aq., aq.—aqueous
Ar—argon (gas)
BOP—benzotriazol-1-yl-oxy Hexafluorophosphate
BuLi—Butyllithium
$Cs_2CO_3$—cesium carbonate
$CHCl_3$—chloroform
$CH_2Cl_2$, DCM—dichloromethane, methylene chloride
Cu(1)I—copper(1) iodide
DCC—dicyclohexylcarbodiimide
DEA—diethylamine
DIC—1,3-diisopropylcarbodiimide
DIEA, DIPEA—diisopropylethylamine
DME—dimethoxyethane
DMF—dimethylformamide
DMAP—4-dimethylaminopyridine
DMSO—dimethylsulfoxide
EDC, EDCl—(3-dimethylaminopropyl)-3-ethylcarbodiimide
$Et_2O$—diethyl ether
EtOAc—ethyl acetate
G, gm—gram
h, hr—hour
$H_2$—hydrogen (gas)
$H_2O$—water
HATU—O-(7-azabenzotriazol-1-yl)-N,N,N',N'-tetramethyluroniumhexafluorophosphate
HBr—hydrobromic acid
HCl—hydrochloric acid
HOBt—1-hydroxybenzotriazole hydrate
HOAc—acetic acid
HPLC—high pressure liquid chromatography
IPA, IpOH—isopropyl alcohol
$K_2CO_3$—potassium carbonate
KI—potassium iodide
LG—leaving group
LDA—Lithium diisopropylamide
LiOH—lithium hydroxide
$MgSO_4$—magnesium sulfate
MS—mass spectrum
MeOH—methanol
$N_2$—nitrogen (gas)
$NaCNBH_3$—sodium cyanoborohydride
$Na_2CO_3$—sodium carbonate
$NaHCO_3$—sodium bicarbonate
NaH—sodium hydride
NaI—sodium iodide
$NaBH_4$—sodium borohydride
NaOH—sodium hydroxide
$Na_2SO_4$—sodium sulfate
$NH_4Cl$—ammonium chloride
$NH_4OH$—ammonium hydroxide
$P(t-bu)_3$—tri(tert-butyl)phosphine
Pd/C—palladium on carbon
$Pd(PPh_3)_4$—palladium(0)triphenylphosphine tetrakis
$Pd(dppf)Cl_2$—palladium(1,1-bisdiphenylphosphinoferrocene) II chloride
$Pd(PhCN)_2Cl_2$—palladium di-cyanophenyl dichloride
$Pd(OAc)_2$—palladium acetate
$Pd_2(dba)_3$—tris(dibenzylideneacetone) dipalladium
PyBop—benzotriazol-1-yl-oxy-tripyrrolidino-phosphonium hexafluorophosphate
RT, rt—room temperature
RBF, rbf—round bottom flask
TLC, tlc—thin layer chromatography
TBAF—Tetrabutylammonium flouride
TBTU—O-benzotriazol-1-yl-N,N,N,N'-tetramethyluronium tetrafluoroborate
TEA, $Et_3N$—triethylamine
TFA—trifluoroacetic acid
THF—tetrahydrofuran
UV—ultraviolet light

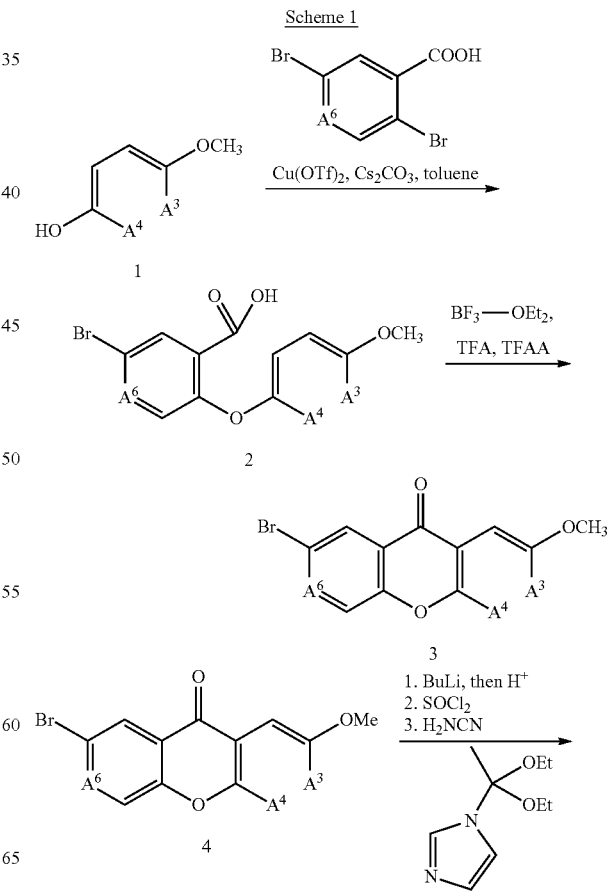

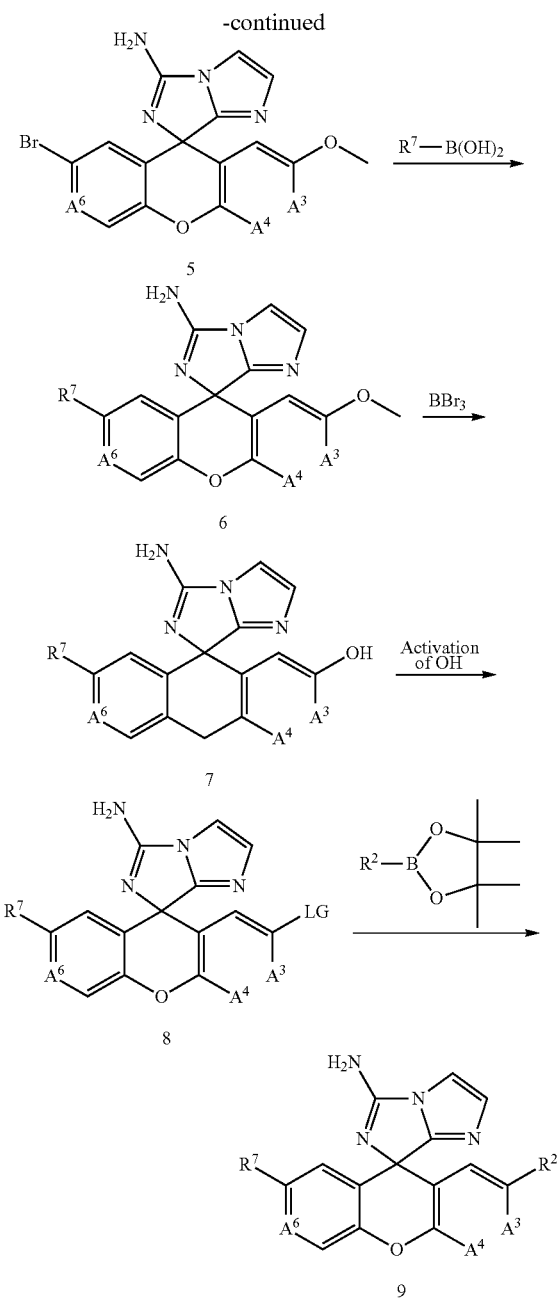

Scheme 1 describes an exemplary method for preparing racemic compounds 8 of Formulas I, II and III, wherein each of $A^1$, $A^5$ and $A^8$ are CH, respectively, and —X—Y— taken together is —CH=CH—. One can start by reacting methoxy-hydroxy-pyridine (wherein either $A^3$ or $A^4$=N) or 4-methoxy-phenol with 2,5-dibromobenzoic acid (wherein $A^6$=CH; or 2,5-dibromopicolinic acid) in the presence of a suitable base, such as cesium carbonate as shown above, to afford the ether linked adduct 2. The carboxylic acid of 2 may then be closed to the corresponding ketone 3 under suitable conditions, such as those described herein in scheme 1, as well as in the Examples herein.

Ketone intermediate 3, and similar intermediates, may also be prepared in accordance to that described in PCT published patent application WO2010030954, pages 53, Scheme 2, compounds 9-13; Scheme 3b on pg 55, compound 32; Example 1 on pg 59, lines 17-pg 60, line 10; Example 3 on pg 62; and Example 5-7 beginning on pg 65 of WO2010030954, each disclosure of which is expressly incorporated herein by reference.

Ketone 3 may be converted to the corresponding amino-imidazo-imidazole adduct 5 using the conditions described herein, as shown in scheme 1. The bromide of intermediate 5 can be displaced with a desired aromatic $R^7$ moiety, via a Suzuki or Suzuki-like aromatic-halogen exchange reactions, which reactions generally employ a boronic acid moiety, a palladium catalyst reagent and a base. Other aryl/heteroaryl coupling methods, including Stille and the like under appropriate conditions, may also be employed to provide compounds 6. One of ordinary skill in the art may convert the methoxy group of intermediate 6 to the corresponding hydroxyl group of intermediate 7 via conventional O-demethylations techniques, such as use of $BBr_3$, as described herein, under suitable conditions, to afford compound 7. The hydroxyl group of compound 7 can be activated into a suitable leaving group ("LG" in scheme 1), such as a triflate, as described in the examples herein, or other suitable O-linked leaving group. The leaving group of intermediate 8 can then be reacted with a desired aromatic boronic acid to install the desired $R^2$ group, as shown in scheme 1, to afford the desired compounds 9 of Formula I, II and III.

The boronic ester intermediates utilized in steps 4 and/or 7 may be prepared by methods described in the following references: (1) PCT Int. Patent Appl. No. WO 2005073189, titled "Preparation of fused heteroaryl derivatives as p38 kinase inhibitors" or (2) PCT Int. Patent Appl. No. WO 2006094187, titled "Preparation of phthalazine, aza- and diaza-phthalazine compounds as protein kinase, especially p38 kinase, inhibitors for treating inflammation and related conditions". Also, desired boronic acids may be purchased commercially from vendor catalogs, or specially made by the vendor or by persons of ordinary skill in the art.

The Suzuki method is a reaction using a borane reagent, such as a boronic acid or ester such as a dioxaborolane (see Examples herein), and a suitable leaving group containing reagent, such as the xanthene 8 or bromo-xanthene 6 (halogens, including bromides and chlorides are suitable halogen leaving groups "LG"). As appreciated to one of ordinary skill in the art, Suzuki reactions also utilize a palladium catalyst. Suitable palladium catalysts include, without limitation, $Pd(PPh_3)_4$, $Pd(OAc)_2$ or $Pd(dppf)Cl_2$. Where LG is a halide, the halide may be an iodide, a bromide or chloride. Chloropyridyl rings (where $A^1$=N) undergo Suzuki reactions in the presence of Pd catalysts. Other LGs are also suitable. For example, Suzuki couplings are known to occur with a sulfonate, such as trifluoromethanesulfonate, as the leaving group.

The Suzuki reaction conditions may vary. For example, Suzuki reactions are generally run in the presence of a suitable base such as a carbonate base, bicarbonate or an acetate base, in a suitable solvent such as toluene, acetonitrile, DMF or an aqueous-organic solvent combination or a biphasic system of solvents. Further, the reaction may require heat depending upon the particular bromide 5 and/or boronic acid or ester, as appreciated by those skilled in the art. In addition, where the bromide is an aromatic moiety, such as phenyl, the reaction may be complete in a short period of time with heat.

Other coupling methods are known. For example metal catalized coupling chemistry, such Stille, Kumada, Negishi coupling methods, and the like, may be employed to the xanthene cores 5 and/or 8 to prepare desired cyclic products 9. In addition, compounds may possess groups which may need to be protected (and later deprotected), such as a free amino group, to carry out effective coupling reactions to install either $R^2$ or $R^7$ groups to afford the final desired compounds 9, as appreciated by persons of ordinary skill in the art.

Alternatively, the hydroxyl group of intermediate 7 may be functionalized with the desired O-linked $R^2$ group via a base assisted coupling reaction, as discussed herein, to provide the corresponding bromo-xanthene-$R^2$ intermediate (not shown), as described in scheme 2 below.

Alternatively, ketone 3 may be converted to the corresponding imine, then to the free amine, followed by conversion to the thiocyanide and subsequent ring formation as shown in scheme 2 of *J. Med. Chem.*, 2009, vol. 52, No. 20, 6314-6323. In that reference, the spiro-amino head piece is similar to that of the present invention, although connected to a structurally distinct base portion.

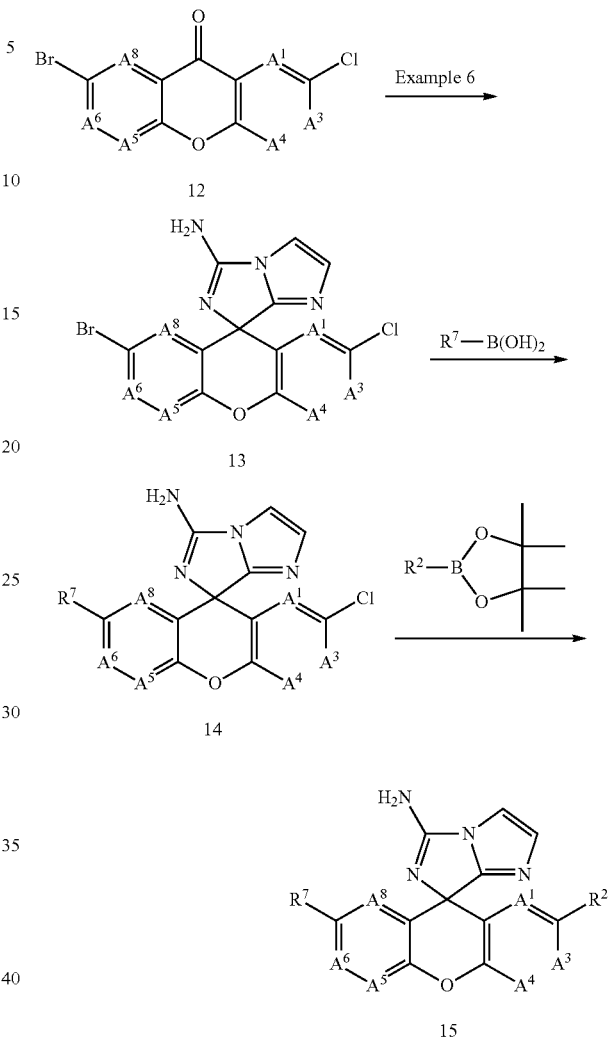

Desired compounds 11 of Formulas I, II and III, and sub-formulas thereof, wherein the $R^2$ group is —$OR^9$ may be made as generally described in Scheme 2. As shown, $R^7$-hydroxy intermediate 7 can be functionalized as desired, such as by alkylation as shown, by reaction with an alkyl halide 10 in the presence of a suitable base, such as cesium carbonate, in suitable solvents to afford the finally desired product(s) 11.

"LG" in this instance is a "leaving group" which may be a halide such as an iodide, bromide, chloride or fluoride. LG may also be a non-halide moiety such as an alkylsulfonate or other known groups which generally form an electrophilic species ($E^+$). Coupling reactions generally occur more readily in one or a combination of solvents and a base. Suitable solvents include, without limitation, generally non-nucleophilic, anhydrous solvents such as toluene, $CH_2Cl_2$, THF, DMF, N,N-dimethylacetamide and the like. The solvent may range in polarity, as appreciated by those skilled in the art. Suitable bases include, for example, tertiary amine bases such as DIEA, TEA, carbonate bases such as $Na_2CO_3$, $K_2CO_3$, $Cs_2CO_3$, hydrides such as NaH, KH and the like, alkoxides such as $NaOCH_3$, and the like. The base itself may also serve as a solvent. These coupling reactions are generally fast and conversion occurs typically in ambient conditions. However, depending upon the particular substrate, such reactions may require heat, as appreciated by those skilled in the art.

Desired compounds 15 of Formulas I, II and III, and sub-Formulas thereof, may be prepared in a manner similar to that described in the Examples hereunder as shown in Scheme 3. Beginning with ketone 12, one of ordinary skill in the art may convert the ketone group to the corresponding spiro-imidazo-imidazole 13 via the techniques described in Example 6.

Intermediate 13 may successively be taken through Suzuki coupling reactions, or Suzuki-like aromatic-halogen exchange reactions including Stille and the like, under appropriate conditions, to provide final compounds 15.

-continued

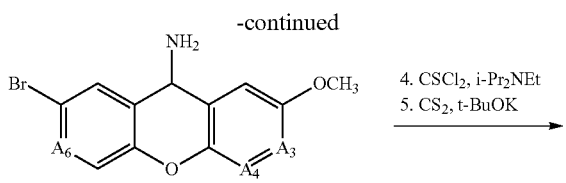
16

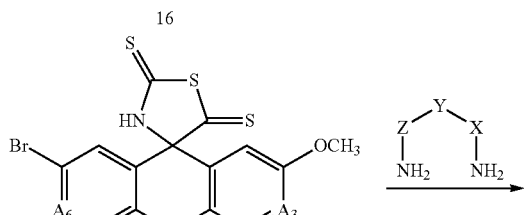
17

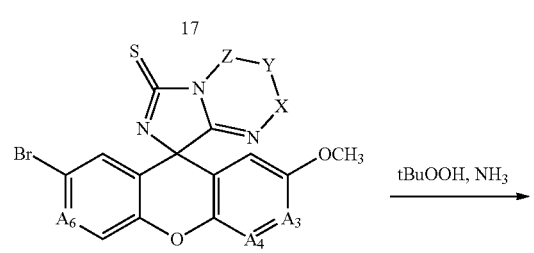
18

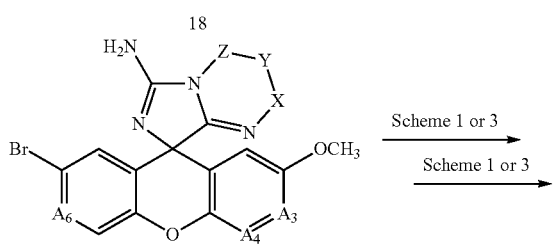
19

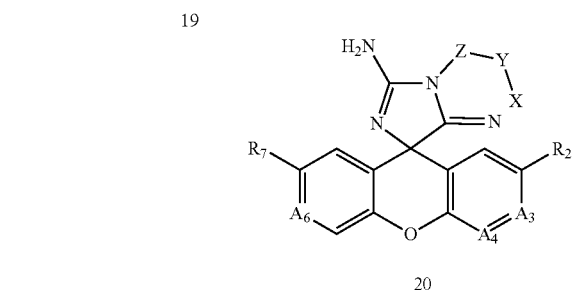
20

Scheme 4 describes an exemplary method for preparing racemic compounds 20 of Formulas I; II and III, wherein each of $A^1$, $A^5$ and $A^8$ are CH, respectively, and —X—Y—Z— taken together may be —CH$_2$—CH$_2$—CH$_2$— or —CH$_2$—CF$_2$—CH$_2$— or any other defined —X—Y—Z— as provided herein in the invention. Beginning with intermediate 3 (from scheme 1 above), the ketone may be reduced using a hydride agent or borohydride as shown, to afford the corresponding alcohol (not shown). The alcohol can be converted to the corresponding chloride using conventional methods, such as thionyl chloride (also not shown). The chloride intermediate can be converted to the corresponding primary amine 16 using an ammonium source, such as ammonium hydroxide or other source. The amine can be treated with thiophosgene under suitable conditions, such as shown above, to afford the corresponding intermediate 17. Compounds 17 can be reacted with a desired diamino compound, such as 1,3-diamino propane (where —X—Y—Z— is —CH$_2$—CH$_2$—CH$_2$—), to afford the ring closed intermediate 18. The thione of 18 can be converted to the corresponding amine 19 under suitable conditions, such as those shown above and in Example 10 herein. Referring to the methods described in schemes 1 and 3 herein, as well as in the Examples, intermediate 19 may be converted to final compounds 20 as desired.

Scheme 5

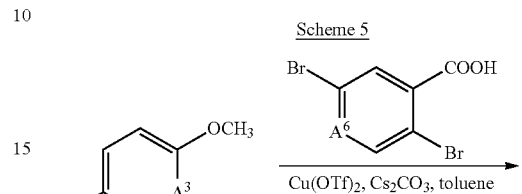
1

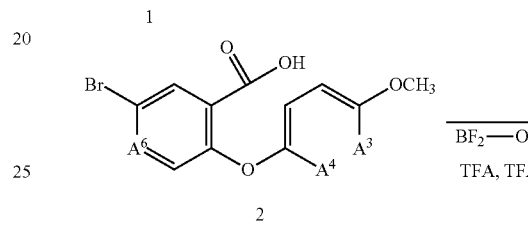
2

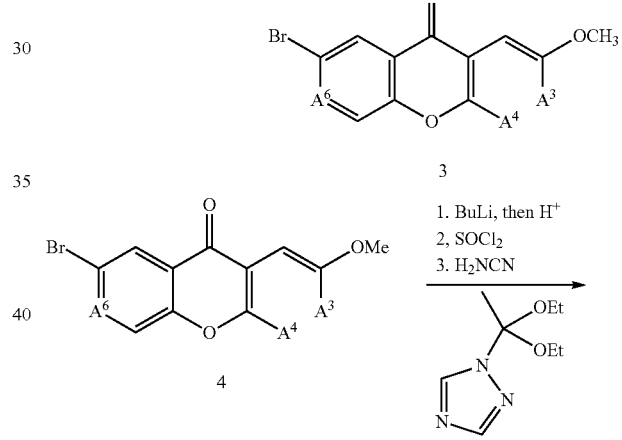
3

4

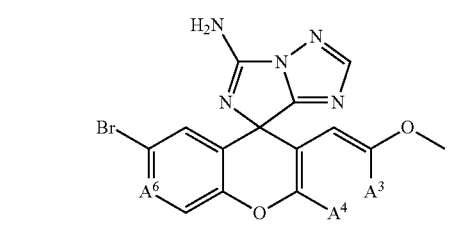
21A

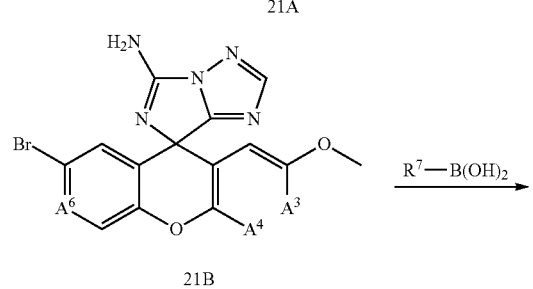
21B

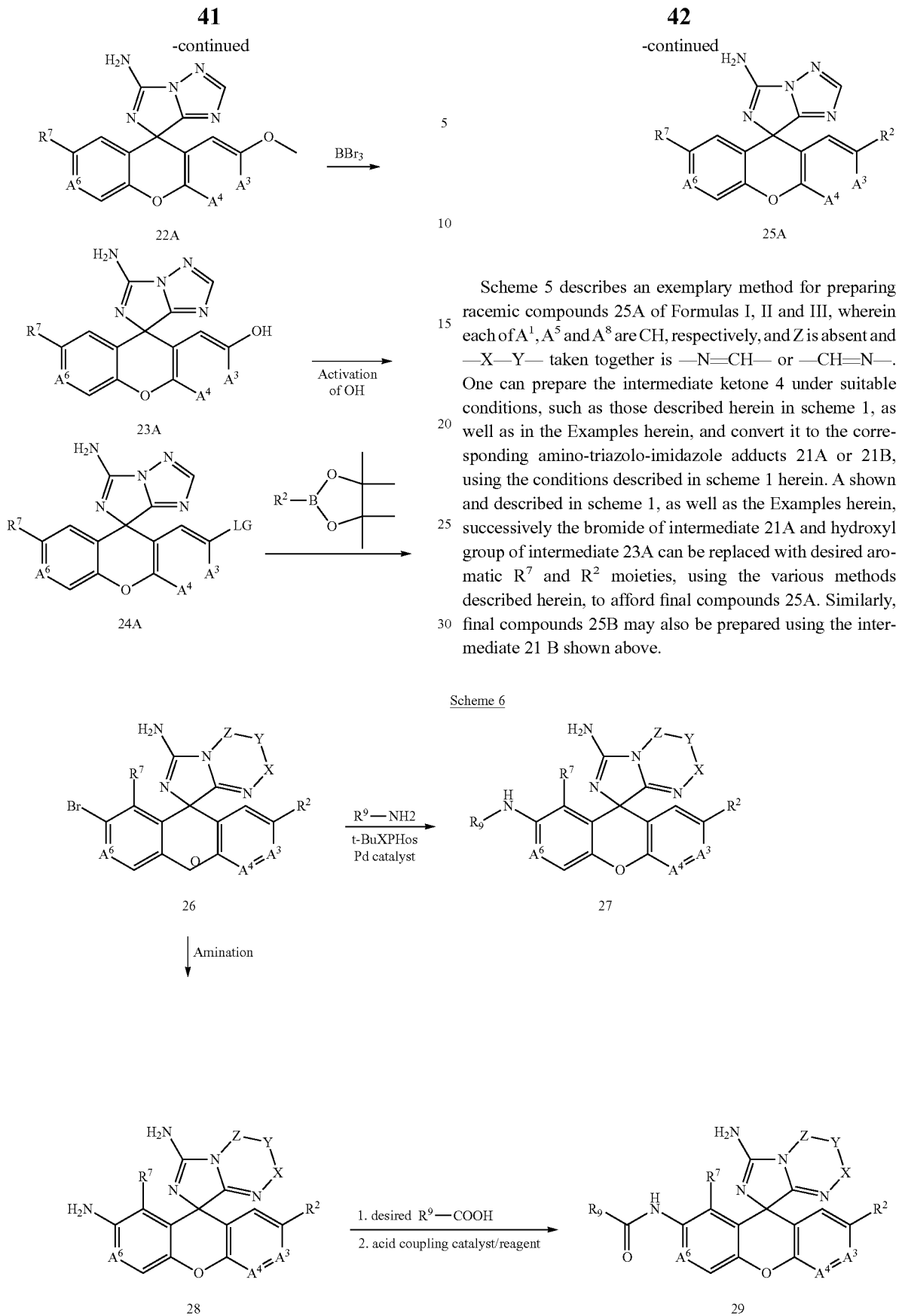

Scheme 5 describes an exemplary method for preparing racemic compounds 25A of Formulas I, II and III, wherein each of $A^1$, $A^5$ and $A^8$ are CH, respectively, and Z is absent and —X—Y— taken together is —N=CH— or —CH=N—. One can prepare the intermediate ketone 4 under suitable conditions, such as those described herein in scheme 1, as well as in the Examples herein, and convert it to the corresponding amino-triazolo-imidazole adducts 21A or 21B, using the conditions described in scheme 1 herein. A shown and described in scheme 1, as well as the Examples herein, successively the bromide of intermediate 21A and hydroxyl group of intermediate 23A can be replaced with desired aromatic $R^7$ and $R^2$ moieties, using the various methods described herein, to afford final compounds 25A. Similarly, final compounds 25B may also be prepared using the intermediate 21 B shown above.

Desired compounds 29 of Formulas I-II, and sub-formulas thereof wherein R⁷ is an amide or sulfonamide linker to desired R⁹ groups may be made as generally described in Scheme 6. As shown, desired R⁹ amines may be coupled directed to the bromide intermediate 26 using XPhos in the presence of a suitable palladium catalyst under suitable conditions to afford desired products 27.

Similarly, compound 30 can be transformed into the corresponding amine 28 using conditions like those described in scheme 1 hereinabove. Compound 28 may then be reacted with a desired acid in the presence of conventional amide coupling conditions to afford desired compound 29. Alternatively the R⁹-acid may be converted to the corresponding acid-halide, such as a reactive acid-chloride using oxalyl chloride under suitable conditions, and reacted with the amine 28 in the presence of a suitable base and solvent to afford product 29.

EXAMPLES

The Examples, described herein below, represent various exemplary starting materials, intermediates and compounds of Formulas which should assist in a better understanding and appreciation of the scope of the present invention and of the various methods which may be used to synthesize compounds of Formulas I-III. Starting materials and intermediates used in the Examples herein may also be prepared using the procedures described in co-pending U.S. patent application Ser. No. 12/558,426, filed Sep. 11, 2009, which specification and disclosure is hereby incorporated herein by reference in its entirety. It should be appreciated that the general methods above and specific examples below are illustrative only, for the purpose of assistance and of understanding the present invention, and should not be construed as limiting the scope of the present invention in any manner.

Chromatography:

Unless otherwise indicated, crude product-containing residues were purified by passing the crude material or concentrate through either a Biotage or Isco brand silica gel column (pre-packed or individually packed with SiO₂) and eluting the product off the column with a solvent gradient as indicated. For example a description of (330 g SiO₂, 0-40% EtOAc/Hexane) means the product was obtained by elution from the column packed with 330 gms of silica, with a solvent gradient of 0% to 40% EtOAc in Hexanes.

Preparative HPLC Method:

Unless otherwise indicated, the compounds described herein were purified via reverse phase HPLC using one of the following instruments: Shimadzu, Varian, Gilson; utilizing one of the following two HPLC columns: (a) a Phenomenex Luna or (b) a Gemini column (5 micron or 10 micron, C18, 150×50 mm)

A typical run through the instrument included: eluting at 45 ml/min with a linear gradient of 10% (v/v) to 100% MeCN (0.1% v/v TFA) in water (0.1% TFA) over 10 minutes; conditions can be varied to achieve optimal separations.

Proton NMR Spectra:

Unless otherwise indicated, all ¹H NMR spectra were run on a Bruker series 300 MHz instrument or a Bruker series 400 MHz instrument. Where so characterized, all observed protons are reported as parts-per-million (ppm) downfield from tetramethylsilane (TMS) or other internal reference in the appropriate solvent indicated.

Mass Spectra (MS)

Unless otherwise indicated, all mass spectral data for starting materials, intermediates and/or exemplary compounds are reported as mass/charge (m/z), having an (M+H⁺) molecular ion. The molecular ion reported was obtained by electrospray detection method (commonly referred to as an ESI MS) utilizing a PE SCIEX API 150EX MS instrument instrument or an Agilent 1100 series LC/MSD system. Compounds having an isotopic atom, such as bromine and the like, are generally reported according to the detected isotopic pattern; as appreciated by those skilled in the art.

The compounds disclosed and described herein have been named using either (1) the naming convention provided with Chem-Draw Ultra 11.0 software, available in Chem Office, or (2) by the ISIS database software (Advanced Chemistry Design Labs or ACD software).

Example 1-A

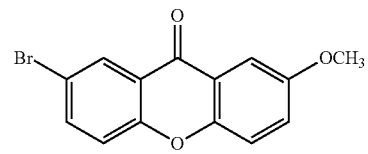 [SMILES: COc1ccc2oc3ccc(Br)cc3c(=O)c2c1]

Synthesis of 2-Bromo-7-methoxy-9H-xanthen-9-one

Step 1: 2-(4-Bromophenoxy)-5-methoxybenzoic acid

4-Bromophenol (8.7 g, 50 mmol), Cs₂CO₃ (16 g, 50 mmol), CuOTf toluene complex (2:1) (0.625 mmol, 5 mol % Cu, 150 mg), ethyl acetate (0.25 ml, 2.5 mmol) were added to a solution of 2-bromo-5-methoxybenzoic acid (11.6 g, 50 mmol) in toluene (40 mL) in a sealed tube. The reaction mixture was purged with N₂, and was heated to 110° C. until the aryl halide was consumed as determined by LC-MS (48 h). After cooling to RT, the mixture was filtered through a Celite plug. The Celite plug was washed with EtOAc. The mixture was acidified by 1N HCl, and extracted w/EtOAc. The combined organic phases were washed with brine, dried over anhydrous sodium sulfate, filtered, and concentrated. This residue was purified via column chromatography on silica gel (gradient elution with 0-10% MeOH/DCM) to afford 2-(4-bromophenoxy)-5-methoxybenzoic acid. MS m/z=324.9 [M+H]₊. Calc'd for C₁₄H₁₁BrO₄: 323.1.

Step 2: 2-Bromo-7-methoxy-9H-xanthen-9-one

Sulfuric acid (41 ml, 765 mmol) was added to 2-(4-bromophenoxy)-5-methoxybenzoic acid (3750 mg, 12 mmol) at RT. The reaction mixture was stirred at 60° C. for 60 min. LCMS showed complete reaction. The reaction mixture was cooled to RT and poured slowly over stirred mixture of ice and water (100 ml). The tan precipitate was filtered and washed with water (3×30 ml), twice with 30 ml of 0.5N NaOH, and with water again. The residue was recrystallized from 40 ml THF to give the title compound. MS m/z=307.2 [M+H]⁺. Calc'd for C₁₄H₉BrO₃: 305.1.

Example 1-B

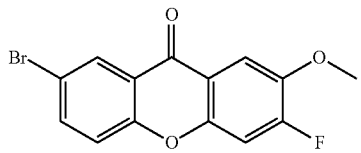 [SMILES: COc1cc2c(=O)c3cc(Br)ccc3oc2cc1F]

Synthesis of 7-Bromo-3-fluoro-2-methoxy-9H-xanthen-9-one

The titled compound was prepared using 2-bromo-4-fluoro-5-methoxybenzoic acid as the starting material, which starting material was prepared as follows:

Step 1: 4-Bromo-2-fluoro-5-methylphenol 2-fluoro-5-methylphenol (23.8 g, 0.19 mol) and bromine (9.7 ml, 0.19 mol) are combined in 50 ml of glacial acetic acid and stirred at RT for one hour. Acetic acid was removed under vacuum. The liquid was diluted with ethyl acetate and washed with water. The organic layer was washed with brine, dried over anhydrous sodium sulfate, filtered and concentrated to afford 4-bromo-2-fluoro-5-methylphenol (38 g, 98% yield) as a colorless liquid. No [M+H] peak by LCMS. 1H NMR (400 MHz, CHLOROFORM-d) δ ppm 1.98 (s, 1H) 2.22 (s, 3H) 6.81 (dd, J=9.15, 0.54 Hz, 1H) 7.17 (d, J=9.88 Hz, 1H)

Step 2: 1-Bromo-5-fluoro-4-methoxy-2-methylbenzene

4-Bromo-2-fluoro-5-methylphenol (40 g, 0.19 mol), cesium carbonate (75 g, 0.23 mol), and iodomethane (15 ml, 0.23 mol) were combined in 100 ml of DMF and stirred at RT for one hour (exothermic). The solution was diluted with ethyl acetate and filtered. The solution was washed with water twice, dried with anhydrous sodium sulfate, filtered, and concentrated. The product was purified via silica gel column chromatography (RediSep 330 g column) using 0-50% ethyl acetate in hexane to afford 1-bromo-5-fluoro-4-methoxy-2-methylbenzene (38 g, 89% yield) as a colorless liquid. No [M+H] peak by LCMS. 1H NMR (400 MHz, CHLOROFORM-d) δ ppm 2.24 (s, 3H) 3.76 (s, 3H) 6.73 (d, J=8.80 Hz, 1H) 7.13 (d, J=10.56 Hz, 1H)

Step 3: 2-Bromo-4-fluoro-5-methoxybenzoic acid

Potassium permanganate (53 g, 3.4 mol) was added to a solution of 1-bromo-5-fluoro-4-methoxy-2-methylbenzene (37 g, 1.7 mol) in 75 ml of pyridine and 150 ml of water at 60° C. The solution was stirred at 60° C. degrees for 24 hours. The solution was filtered and the solids were washed with a solution of water/methanol (50:50). The filtrate was concentrated to approximately 100 ml, then acidified (pH 1) with concentrated HCl. The solid was collected by filtration and dried under vacuum to afford 2-bromo-4-fluoro-5-methoxybenzoic acid as an off white solid. MS m/z=248.9 [M+H].

Step 4: 7-Bromo-2-fluoro-3-methoxy-9H-xanthen-9-one

Sulfuric acid (41 ml, 765 mmol) was added to 2-bromo-4-fluoro-5-methoxybenzoic acid (3.75 g, 12 mmol) at RT. The reaction mixture was stirred at 60° C. for 60 min. LCMS showed complete reaction. The reaction mixture was cooled to RT and poured slowly over stirred mixture of ice and water (100 ml). The tan precipitate was filtered and washed with water (3×30 ml), twice with 30 ml of 0.5N NaOH, and with water again. The residue was recrystallized from 40 ml THF to give the title compound. MS m/z=326.2 [M+H]$^+$. Calc'd for $C_{14}H_9FBrO_3$: 325.1.

Example 2

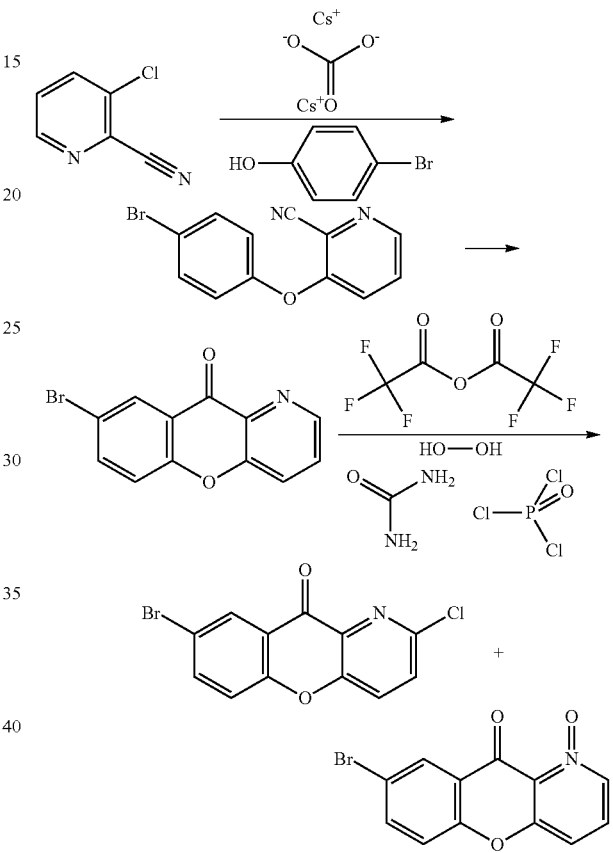

Synthesis of 8-Bromo-2-chloro-10H-chromeno[3,2-b]pyridin-10-one

Step 1: A RBF was charged with 3-chloro-2-cyanopyridine (40 g, 289 mmol), 4-bromophenol (49.9 g, 289 mmol) and cesium carbonate (113 g, 346 mmol). The reactants were suspended in 50 mL of DMSO and allowed to stir at 85° C. overnight. The reaction was cooled to RT and 600 mL of water was added to it. The reaction was filtered and the solid washed with water, then air dried to provide 3-(4-bromophenoxy)-picolinonitrile as a tan solid.

Step 2: A mixture of 3-(4-bromophenoxy)-picolinonitrile (57 g, 207 mmol) and 300 g of PPA was stirred at 190° C. for 2 h, followed by 180° C. overnight. After cooling to RT, the reaction mixture was poured into 500 g of ice water. After the PH was adjusted to 7 with KOH, the suspension was filtered. The solid was washed with large excess of water, followed by washing with methanol and acetone. The resulting solid was air dried to give 8-bromo-10H-chromeno[3,2-b]pyridin-10-one as a tan solid with >90% purity. The material was carried on to the next step.

Step 3: To a solution of 8-bromo-10H-chromeno[3,2-b]pyridin-10-one (60 g, 217 mmol) and urea peroxide (42.9 g, 456 mmol) in 120 mL of DCM at 0° C. was added dropwise trifluoroacetic anhydride (63.9 mL, 456 mmol). The resulting reaction was stirred for 2 h. The reaction was quenched with 10% $Na_2S_2O_3$, extracted with DCM, dried over $Na_2SO_4$ and evaporated to dryness to give crude 8-bromo-10-oxo-10H-chromeno[3,2-b]pyridine 1-oxide as a pale yellow solid.

Step 4: To a suspension of 8-bromo-10-oxo-10H-chromeno[3,2-b]pyridine 1-oxide in 100 mL of toluene at 0° C. was added dropwise phosphorus oxychloride (35.8 mL, 391 mmol) followed by 2 mL of DMF and the mixture was stirred at RT overnight. The solvent was evaporated under vacuum and the residue which crashed out of water, was filtered and washed with water, methanol and acetone in sequence. The solid was air dried to give 8-bromo-2-chloro-10H-chromeno[3,2-b]pyridin-10-one as a tan solid.

Example 3

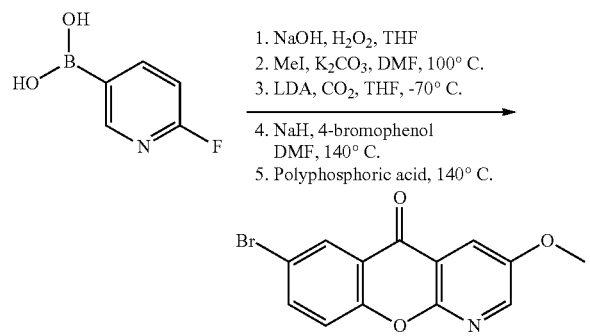

Synthesis of 7-Bromo-3-methoxy-5H-chromeno[2,3-b]pyridin-5-one

Step 1: A three neck 3-L RBF equipped with an overhead stirred was charged with 6-fluoropyridin-3-ylboronic acid (105 g, 745 mmol) and 1 L of THF. The mixture was cooled to 0° C. and NaOH 6N (373 mL, 2235 mmol) was added. To the resulting mixture was added hydrogen peroxide 30% (126 mL, 4098 mmol), dropwise via an addition funnel over the course of 30 minutes. After stirring at 0° C. for 2 hours the mixture was removed from the ice bath and maintained at RT for 30 minutes. The reaction was acidified to pH 7 with 6 N HCl (ca. 300 mL) and diluted with 500 mL of ether. The aqueous layer was extracted with ether (2×1 L) and the combined organic layers were washed with water (1.5 L) then brine before being dried over sodium sulfate. Filtration and concentration provided a white solid that was dried on high vac overnight to provide 6-fluoropyridin-3-ol.

Step 2: To a solution of 6-fluoropyridin-3-ol (75 g, 663 mmol) in DMF (265 mL, 663 mmol) were added potassium carbonate (59.7 g, 995 mmol) and iodomethane (108 g, 763 mmol). The resulting slurry was heated at 100° C. for 3 hours. The reaction was diluted with water (1000 mL) and poured into a separatory funnel containing diethyl ether (1000 mL). The layers were separated and the aqueous layer was extracted with diethyl ether (4×500 mL). The combined organic layers were washed with water and then brine, dried over sodium sulfate, filtered and concentrated in vacuo to provide a yellow oil. This oil was diluted with 500 mL of DCM and concentrated to provide a yellow oil with a large amount of an off white precipitate. The mixture was filtered and the derived solid was washed well with DCM. The filtrate was concentrate to provide a mixture consisting of a yellow oil and an off white solid. The solid was filtered, washing with DCM. Repeat this procedure again and then concentrated the filtrate to provide a yellow oil. The oil was taken up in 100 mL of ether and flashed through a plug of silica gel with 10:1 hexanes:ether to provide 2-fluoro-5-mahoxypyridine as a yellow oil.

Step 3: To a solution of DIPA (54.0 mL, 385 mmol) in THF (1101 mL, 385 mmol) at −60° C. was added BuLi, 2.5 M in hexanes (154 mL, 385 mmol) over 5 minutes such that the internal temperature was maintained below −60° C. After stirring for 45 minutes at −65. ° C. a solution of 2-fluoro-5-methoxypyridine (49 g, 385 mmol) in 200 mL of THF was added over the course of 2 minutes maintaining an internal temperature <−65° C. The reaction was stirred at −70° C. for 1.5 hours then reaction was poured into a 3 L flask containing 1200 g of crushed dry ice. The reaction was allowed to warm to 0° C. and then poured into 1000 mL of water. The organics were removed under reduced pressure and the aqueous layer was acidified with 1100 mL of 2 N HCl. The resulting thick white slurry was stirred for 1 hour then filtered to provide 2-fluoro-5-methoxynicotinic acid as a white solid.

Step 4: To a slurry of NaH (60% dispersion) (21.74 g, 543 mmol) in DMF (351 mL, 175 mmol) at 0° C. was added 4-bromophenol (60.7 g, 351 mmol) over the course of 5 minutes. Stirred at 0° C. for two minutes then removed from the ice bath and stirred for an additional 5 minutes at RT. Added 2-fluoro-5-methoxynicotinic acid (30 g, 175 mmol) portionwise over 10 minutes and heated the resulting slurry at 140° C. After cooling to RT the mixture was then poured onto 1 kg of ice and was quenched with acetic acid (50.2 mL, 877 mmol) and then 75 mL of 6 N HCl. Stirred vigorously for 1 hr; leading to the formation of a red slurry containing a very fine white precipitate. The slurry was filtered to provide 2-(4-bromophenoxy)-5-methoxynicotinic acid.

Step 5: A 2 L RBF charged with polyphosphoric acid (115% $H_3PO_4$) (300 g, 89 mmol) was heated to 140° C. at which point 2-(4-bromophenoxy)-5-methoxynicotinic acid (29 g, 89 mmol) was introduced. The thick viscous mixture is slowly stirred while heating at 140° C. After heating for 2.5 hours the solution was cooled to 100° C. and then poured onto 1 kg of ice, leading to the formation of a yellow taffy mixture. The slurry was vigorously stirred for 1 hour leading to the formation of a fine white precipitate. Filtration of this mixture proceeded slowly to provide an off white solid. This solid was washed well with DCM. The filtrate, which contained the desired product, was washed with brine and concentrated to provide 7-bromo-3-methoxy-5H-chromeno[2,3-b]pyridin-5-one as an off-white solid.

Example 4

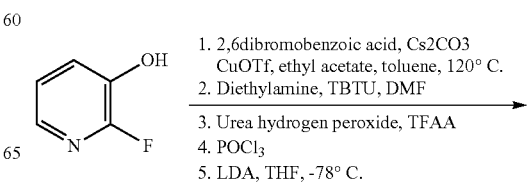

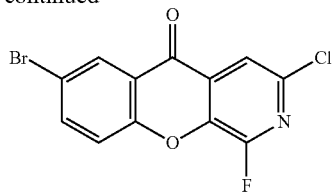

Synthesis of 7-Bromo-3-chloro-1-fluoro-5H-chromeno[2,3-c]pyridin-5-one

Step 1: A 500 mL RBF was charged with 2-fluoro-3-hydroxypyridine (3487 mg, 30.8 mmol), 2,5-dibromobenzoic acid (8630 mg, 30.8 mmol), copper (I) trifluoromethanesulfonate toluene complex (2:1) (399 mg, 0.771 mmol) and cesium carbonate (2.01E+04 mg, 61.7 mmol). To this was added 100 mL of toluene and the mixture was azeotroped to remove about 20 mL of toluene under reduced pressure. Reaction mixture was then flushed with $N_2$ and was heated to 120° C. for 2 hours. LC-MS analysis showed formation of the desired product along with significant impurities. The reaction mixture was cooled to RT and concentrated to give a gummy residue. The residue was taken up in ethyl acetate (100 mL) and water (75 mL). The aqueous layer was neutralized with 1N HCl to pH~2.0-3.0. The aqueous layer was extracted with EtOAc (2×150 mL), separated, dried over anhydrous sodium sulfate, and concentrated to yield the crude product as a brown solid which was used directly in the next step.

Step 2: A mixture of crude 5-bromo-2-(2-fluoropyridin-3-yloxy)benzoic acid (8.00 g, 25.6 mmol), diethylamine (6.63 mL, 64.1 mmol) and TBTU (8.23 g, 25.6 mmol) in 8 mL of DMF was stirred overnight. The reaction was quenched with sat. $NaHCO_3$, extracted with EA/H=2:1, washed with brine, dried over $Na_2SO_4$, filtered and evaporated to dryness. CC (DCM to DCM/EA 100:5 to 100:10 to 100:20 to 3:1) gave 5-bromo-N,N-diethyl-2-(2-fluoropyridin-3-yloxy)benzamide as a yellow solid.

Step 3: To a solution of 5-bromo-N,N-diethyl-2-(2-fluoropyridin-3-yloxy)benzamide (1.4 g, 3.81 mmol) and urea peroxide (1.076 g, 11.44 mmol) in 10 mL of DCM at 0 C was added dropwise trifluoroacetic anhydride (1.601 mL, 11.44 mmol) and the resulting reaction was stirred overnight. LCMS showed only less than 50% of desired conversion. The mixture was evaporated to dryness, quenched with Sat. $NaHCO_3$, extracted with EA, dried over $Na_2SO_4$, filtered and evaporated to dryness. The crude product was purified using column chromatography (DCM to DCM/EA=3:1 to DCM/MeOH=100:2 to 100:5 to 100:10) to provide 3-(4-bromo-2-(diethylcarbamoyl)phenoxy)-2-fluoropyridine 1-oxide as an offwhite solid.

Step 4: To a solution of 3-(4-bromo-2-(diethylcarbamoyl)phenoxy)-2-fluoropyridine 1-oxide (420 mg, 1.096 mmol) in 15 mL of DCM was added dropwise phosphorus oxychloride (301 μl, 3.29 mmol) followed by 2 drops of DMF. After stirring at rt for 1 h, the reaction was quenched with sat. $NaHCO_3$, extracted into EtOAc, dried over $Na_2SO_4$, filtered and concentrated under reduced pressure. The crude was purified by column chromatography (DCM to DCM/EtOAc gradient beginning from 10:1 to 5:1 to 3:1) gave 5-bromo-2-(6-chloro-2-fluoropyridin-3-yloxy)-N,N-diethylbenzamide as a colorless gum.

Step 5: To a solution of 5-bromo-2-(6-chloro-2-fluoropyridin-3-yloxy)-N,N-diethylbenzamide (120 mg, 0.299 mmol) in 5 mL of dry THF at −78° C. was added dropwise lithium diisopropylamide, 2.0M heptane/THF/ethylbenzene (158 μL, 1.195 mmol) (0.6 mL of 2M solution) and the reaction was stirred at −78° C. for 3 h. The reaction was quenched at −78° C. with sat. $NH_4Cl$ and was allowed to warm up to RT. The reaction was extracted with ETOAc, dried over $Na_2SO_4$, filtered and evaporated to dryness. The crude was purified by column chromatography (1:1 hexane/DCM to 100% DCM) to give the titled compound, 7-bromo-3-chloro-1-fluoro-5H-chromeno[2,3-c]pyridin-5-one, as an offwhite solid. MS (M+1): 328.

Example 5

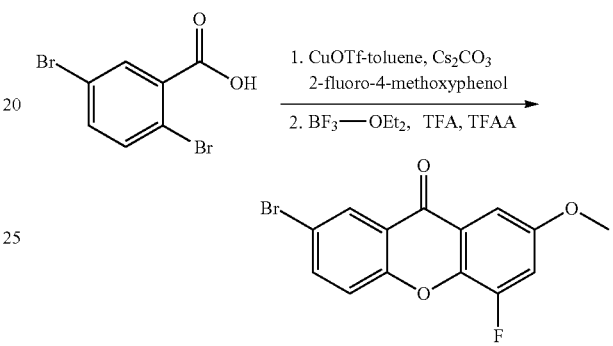

Synthesis of 7-bromo-4-fluoro-2-methoxy-9H-xanthen-9-one

Step 1: A dry 100 L glass jacketed reactor equipped with an addition funnel, reflux condenser, solids addition system and temperature probe was charged with 2,5-dibromobenzoic acid (2685 g, 9.6 mol) and copper (I) triflate toluene complex (2:1, 50.0 g, 0.2 mol). Toluene (30 L) and EtOAc (20 mL) were then added to the reactor, followed by 2-methoxy-4-fluorophenol (1500 g, 10.6 mol). With vigorous stirring cesium carbonate (6258 g, 19.2 mol) was added to the mixture in portions. The mixture was heated to 90° C. for 4 hours. The mixture was cooled to 35° C. and water (15 L) was added. After 15 minutes of stirring the phases were sping and the aqueous phase was washed with toluene (7.5 L). With stirring, EtOAc (15.0 L) was added to the mixture, followed by 6 M HCl (5.6 L) keeping the internal temperature below 30° C. The layers were separated and the organics were dried over $MgSO_4$. Filtration through a pad of celite and concentration provided a solid that was reslurried in 915 mL of EtOAc and 9.2 L of heptanes. Stirring was continued for 1 hour before the solids were filtered and washed with heptanes. The solids were dried to provide 2560 g of 5-bromo-2-(2-fluoro-4-methoxyphenoxy)benzoic acid as a cream colored solid.

Step 2: A dry 100 L glass jacketed reactor equipped with an addition funnel, reflux condenser and temperature probe was charged with 5-bromo-2-(2-fluoro-4-methoxyphenoxy)benzoic acid (2340 g, 6.9 mol). TFA (11.7 L) was carefully added to the mixture followed by TFAA (1144 mL). Boron trifluoride diethyl etherate (85 mL, 0.68 mol) was then carefully added, and the mixture was stirred for 4 hours at which point the reaction was transferred to another 100 L glass reactor containing 35.1 L of water cooled at 0° C. The resulting slurry was allowed to warm to RT and stirred for 1 hour. The solids were filtered and washed with water (4.7 L) and 3 N NaOH (2×3.5 L) and water (7 L). The solids were transferred into a 22 L reactor and acetone (4.7 L) was added. The solids were slurried for 1.5 hour and the filtered, washing well with acetone (4.7 L). An additional slurry with acetone (6.4 L @ 45° C.) provided 1310 g of 7-bromo-4-fluoro-2-methoxy-9H-xanthen-9-one as an off white solid.

Example 6

Method A1

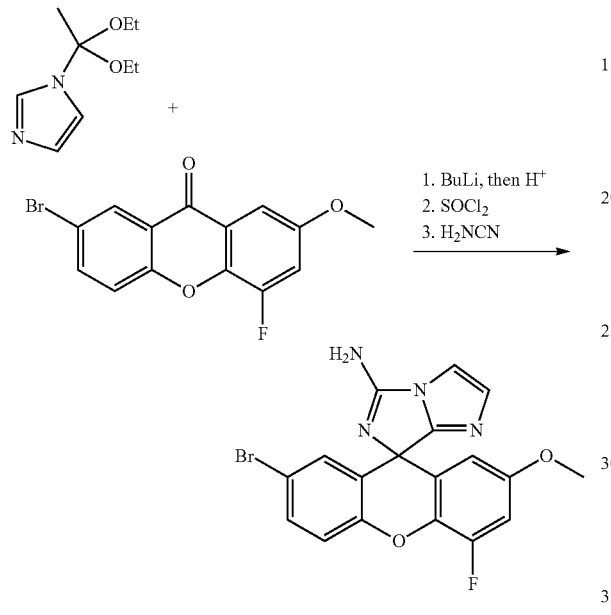

Synthesis of r-bromo-4'-fluoro-2'-methoxyspiro[imidazo[1,5-a]imidazole-7,9'-xanthen]-5-amine Step 1: 1-(1,1-Diethoxyethyl)-1H-imidazole (7 g, 38.0 mmol) was dissolved in diethyl ether (100 ml) and cooled to −40° C. and n-BuLi (1.6M in hexane) (23.75 ml, 38.0 mmol) was added. The solution was stirred for 10 minutes and 7-bromo-4-fluoro-2-methoxy-9H-xanthen-9-one (Example 5, 6.14 g, 19.00 mmol) was added in one portion. The solution was stirred one hour at −40° C., then allowed to warm to RT for 15 minutes. The solution was quenched with 2 N HCl until at pH 1, stirred for 15 minutes, then made basic with concentrated sodium carbonate and stirred for 15 minutes. The product was collected by filtration. The filtrate was also extracted with EtOAc, the extracts were concentrated and combined with the material collected by filtration. The product was loaded onto silica and purified via silica gel column chromatography (RediSep 80 g column) using 10-50% 90/10/1 (DCM/MeOH/ammonia) in DCM to afford 7-bromo-4-fluoro-9-(1H-imidazol-2-yl)-2-methoxy-9H-xanthen-9-ol (3.4 g, 8.69 mmol) as an off white solid.

Step 2: 7-Bromo-4-fluoro-9-(1H-imidazol-2-yl)-2-methoxy-9H-xanthen-9-ol (10 g, 25.6 mmol) was dissolved in 100 ml of benzene and thionyl chloride (18.66 ml, 256 mmol) was added. The solution was refluxed for 4 hours. The reaction was then concentrated to afford 2-(7-bromo-9-chloro-4-fluoro-2-methoxy-9H-xanthen-9-yl)-1H-imidazole (10 g, 24.41 mmol).

Step 3: To 2-(7-bromo-9-chloro-4-fluoro-2-methoxy-9H-xanthen-9-yl)-1H-imidazole (10 g, 24.41 mmol) was added a solution of cyanamide (1.539 g, 36.6 mmol) in dioxane (244 mL). The solution was stirred at RT for 30 minutes. The solution was then heated at reflux for 6 hrs until only a product peak was seen by LCMS. The solution was concentrated under vacuum. The solution was quenched with 500 ml of saturated sodium bicarbonate and 500 ml of water, and sonicated for 30 minutes. The product was then collected by filtration. The solid was then triturated with DCM and dried under vacuum to afford 7'-bromo-4'-fluoro-2'-methoxyspiro[imidazo[1,5-a]imidazole-7,9'-xanthen]-5-amine (10 g, 24.4 mmol) as a light brown solid.

Example 7

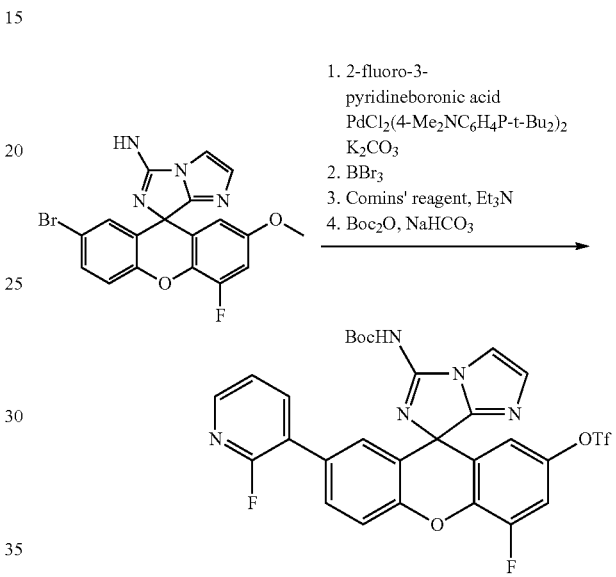

Synthesis of 5-(tert-butoxycarbonylamino)-5'-fluoro-2'-(2-fluoropyridin-3-yl) spiro[imidazo[1,5-a]imidazole-7,9'-xanthene]-7'-yl trifluoromethanesulfonate Step 1: A pressure vessel was charged with potassium carbonate (1M solution) (49 mL, 49 mmol), bis(di-tert-butyl (4-dimethylaminophenyl)phospine)dichloropalladium(II) (1.739 g, 2.457 mmol), 2-fluoropyridin-3-ylboronic acid (3.46 g, 24.57 mmol), and 7'-bromo-4'-fluoro-2'-methoxyspiro[imidazo[1,5-a]imidazole-7,9'-xanthen]-5-amine (5.1 g, 12.28 mmol). Dioxane (150 mL) was added and the mixture was capped under argon, sonicated for 1 min and heated at 100° C. for 4 hours. The solution was concentrated. Material was purified via silica gel column chromatography using 50-100% ethyl acetate in hexane to afford 4'-fluoro-7'-(2-fluoropyridin-3-yl)-2'-methoxyspiro[imidazo[1,5-a]imidazole-7,9'-xanthen]-5-amine (3 g, 6.95 mmol) as a white solid.

Step 2: 4'-Fuoro-7'-(2-fluoropyridin-3-yl)-2'-methoxyspiro[imidazo[1,5-a]imidazole-7,9'-xanthen]-5-amine (3 g, 6.95 mmol) was dissolved in 200 ml of DCM and BBr$_3$ (3.29 ml, 34.8 mmol) was added. The solution was stirred at RT for 3 hours. The solution was quenched with 250 ml of saturated sodium bicarbonate followed by 25 ml of MeOH. The solution was stirred for 30 minutes. 100 ml of DCM was then added and the water layer was extracted with DCM and EtOAc. The combined organic extracts were concentrated to afford 5-amino-4'-fluoro-7'-(2-fluoropyridin-3-yl)spiro[imidazo[1,5-a]imidazole-7,9'-xanthen]-2'-ol which was used in the next step without purification Step 3: To a suspension of 5-amino-4'-fluoro-7'-(2-fluoropyridin-3-yl)spiro[imidazo[1,5-a]imidazole-7,9'-xanthen]-2'-ol (1.8 g, 4.31 mmol) and triethylamine (1.262 ml, 9.06 mmol) in DCM (50 mL) was added N-(5-chloropyridin-2-yl)-1,1,1-trifluoro-N-(trifluoromethylsulfonyl)methanesulfonamide (1.863 g, 4.74 mmol) and the mixture was sonicated for one hour at RT. The mixture was diluted with DCM (50 mL), washed with 1N NaOH solution twice and concentrated. The product was purified via silica gel column chromatography eluting with a gradient of 0-80% of solvent 90/10/1 (DCM/MeOH/ammonia) in DCM to afford 5-amino-5'-fluoro-2'-(2-fluoropyridin-3-yl)spiro[imidazo[1,5-a]imidazole-7,9'-xanthene]-7'-yl trifluoromethanesulfonate (2 g, 3.64 mmol) as a yellow foam.

Step 4: Boc-anhydride (4.23 mL, 18.20 mmol) and 5-amino-5'-fluoro-2'-(2-fluoropyridin-3-yl)spiro[imidazo[1,5-a]imidazole-7,9'-xanthene]-7'-yl trifluoromethanesulfonate (2 g, 3.64 mmol) were combined in saturated sodium bicarbonate (18 mL) and Dioxane (18 mL) and stirred vigorously at RT overnight. The solution was diluted with water. The aqueous layer was extracted with EtOAc and the combined organic layers were washed with brine and dried over anhydrous sodium sulfate, filtered and concentrated. The product was purified via silica gel column chromatography using 0-100% 90/10/1(DCM/MeOH/ammonia) in DCM to afford 5-(tert-butoxycarbonylamino)-5'-fluoro-2'-(2-fluoropyridin-3-yl)spiro[imidazo[1,5-a]imidazole-7,9'-xanthene]-7'-yl trifluoromethanesulfonate (1.9 g, 2.93 mmol).

Examples 8A & 8B

Method A3

Synthesis of (S)-4'-fluoro-7'-(2-fluoropyridin-3-yl)-2'-(2-fluoropyridin-4-yl)spiro[imidazo[1,5-a]imidazole-7,9'-xanthen]-5-amine, and (R)-4'-fluoro-7'-(2-fluoropyridin-3-yl)-2'-(2-fluoropyridin-4-yl)spiro[imidazo[1,5-a]imidazole-7,9'-xanthen]-5-amine PdCl$_2$dppf (25.1 mg, 0.031 mmol), potassium carbonate (1232 µL, 1.232 mmol), 2-fluoropyridin-4-ylboronic acid (87 mg, 0.616 mmol), and 5-(tert-butoxycarbonylamino)-5'-fluoro-2'-(2-fluoropyridin-3-yl)spiro[imidazo[1,5-a]imidazole-7,9'-xanthene]-7'-yl trifluoromethanesulfonate (200 mg, 0.308 mmol) were combined in dioxane/water 4:1 (3079 µL) and heated at 100° C. for 2 hours. The solution was concentrated. The product was purified via silica gel column chromatography using 0-60% EtOAc in hexane to afford tert-butyl 4'-fluoro-7'-(2-fluoropyridin-3-yl)-2'-(2-fluoropyridin-4-yl)spiro[imidazo[1,5-a]imidazole-7,9'-xanthene]-5-ylcarbamate (100 mg, 0.168 mmol, 54.4% yield). This material was treated with TFA (0.323 ml, 4.19 mmol) in DCM (2 ml) and stirred at RT for 1 hr. The solution was concentrated, and the racemic residue was separated by SFC using an IC (10×0.46 cm) column, eluting with 20% IPA (DEA)/CO$_2$, 100 bar, 4 mL/min, 220 nm to afford (S)-4'-fluoro-7'-(2-fluoropyridin-3-yl)-2'-(2-fluoropyridin-4-yl)spiro[imidazo[1,5-a]imidazole-7,9'-xanthen]-5-amine (Example 8A) and (R)-4'-fluoro-7'-(2-fluoropyridin-3-yl)-2'-(2-fluoropyridin-4-yl)spiro[imidazo[1,5-a]imidazole-7,9'-xanthen]-5-amine (Example 8B). Mass Spec is in Table 1.

Examples 9A & 9B

Method A4

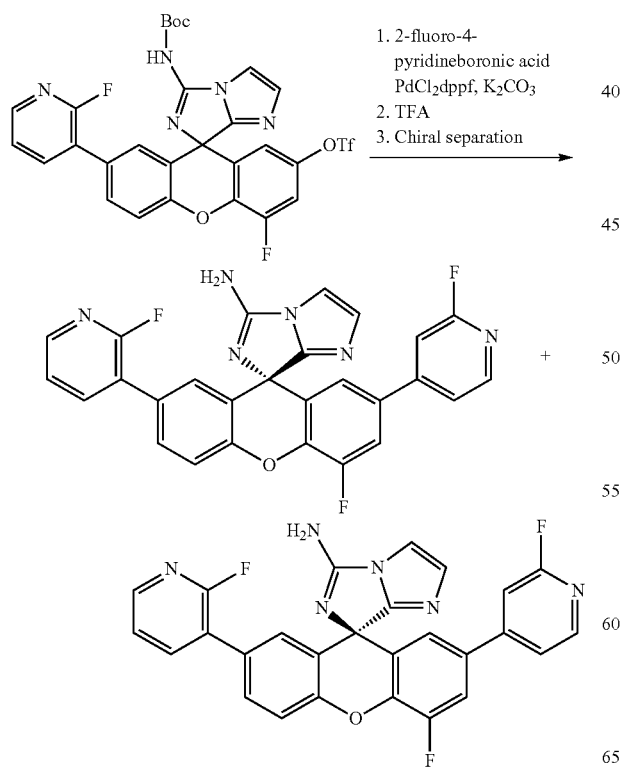

1. 2-fluoro-4-pyridineboronic acid PdCl$_2$dppf, K$_2$CO$_3$
2. TFA
3. Chiral separation

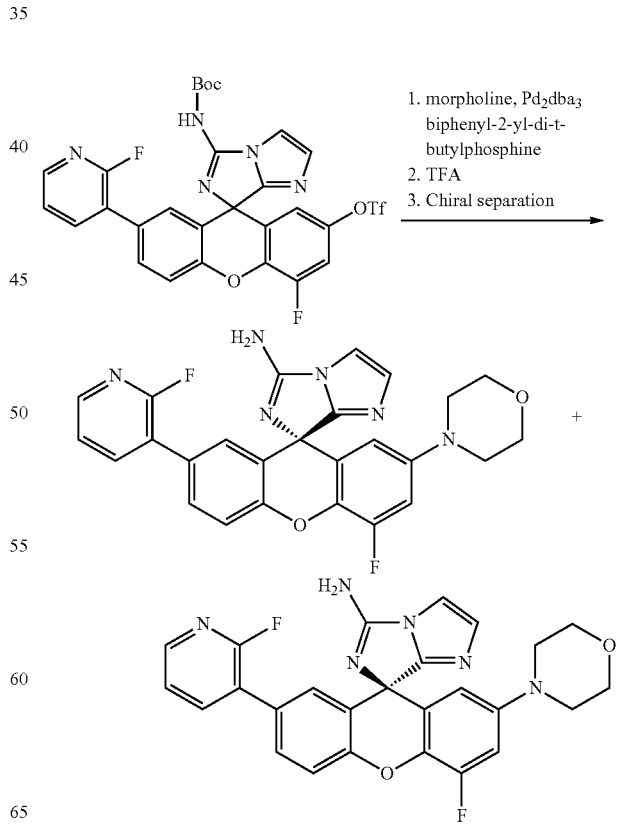

1. morpholine, Pd$_2$dba$_3$ biphenyl-2-yl-di-t-butylphosphine
2. TFA
3. Chiral separation Synthesis of (S)-4'-fluoro-7'-(2-fluoropyridin-3-yl)-2'-morpholinospiro[imidazo[1,5-a]imidazole-7,9'-xanthen]-S-amine; and (R)-4'-fluoro-7'-(2-fluoropyridin-3-yl)-2'-morpholinospiro[imidazo[1,5-a]imidazole-7,9'-xanthen]-5-amine A microwave vial was charged with 5-(tert-butoxycarbonylamino)-5'-fluoro-2'-(2-fluoropyridin-3-yl)spiro[imidazo[1,5-a]imidazole-7,9'-xanthene]-7'-yl trifluoromethanesulfonate (300 mg, 0.462 mmol), Pd$_2$dba$_3$ (21.15 mg, 0.023 mmol), biphenyl-2-yldi-tert-butylphosphine (16.54 mg, 0.055 mmol) and morpholine (141 mg, 1.617 mmol) and capped under argon gas. LiHMDS (1 M in THF) (1.155 mL, 1.155 mmol) was added and the mixture was microwaved at 90° C. for 10 min. Twenty five ml of water was added, and the aqueous layer was extracted with EtOAc and the combined organic layers were dried, filtered and concentrated. The crude material (product) was purified via silica gel column chromatography (RediSep 40 g column) using 0-100% 90/10/1 (DCM/MeOH/ammonia) in DCM to afford tert-butyl 4'-fluoro-7'-(2-fluoropyridin-3-yl)-2'-morpholinospiro[imidazo[1,5-a]imidazole-7,9'-xanthene]-5-ylcarbamate (110 mg, 0.188 mmol, 40.6% yield) as an off white solid. This material was treated with TFA (0.323 ml, 4.19 mmol) in DCM (2 ml) and stirred at RT for one hour. The solution was concentrated, neutralized with sodium barcabonate solution and extracted with DCM. The organic extracts were combined, dried, filtered and concentrated. The crude product (racemic concentrate) was purified via silica gel column chromatography using 0-100% 90/10/1 (DCM/MeOH/ammonia) in DCM, then the racemates were separated using chiral SFC to afford (S)-4'-fluoro-7'-(2-fluoropyridin-3-yl)-2'-morpholinospiro[imidazo[1,5-a]imidazole-7,9'-xanthen]-5-amine (Example no. 9A) and (R)-4'-fluoro-7'-(2-fluoropyridin-3-yl)-2'-morpholinospiro[imidazo[1,5-a]imidazole-7,9'-xanthen]-5-amine (Example no. 9B).

Example 10

Method A5

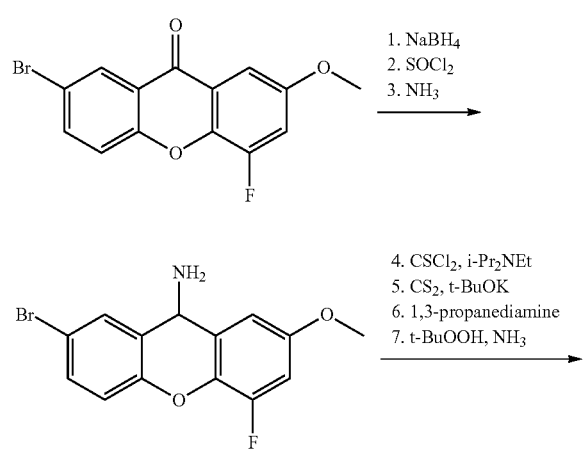

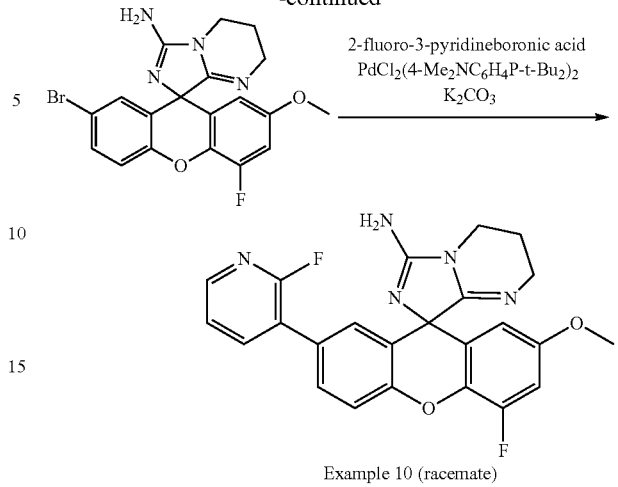

Example 10 (racemate)

Synthesis of 4'-fluoro-7'-(2-fluoropyridin-3-yl)-V-methoxy-3,4-dihydro-2H-spiro[imidazo[1,5-a]pyrimidine-8,9'-xanthen]-6-amine Step 1: To a mixture of 7-bromo-4-fluoro-2-methoxy-9H-xanthen-9-one (45 g, 139 mmol) in THF (400 ml) and MeOH (400 ml) at RT was added NaBH$_4$ (10.54 g, 279 mmol) slowly over the course of one hour. The solution was stirred vigorously for 30 additional minutes, then quenched slowly with a saturated ammonium chloride solution (200 ml). Additional water was added and the mixture was filtered, then washed with water and dried under vacuum to afford 7-bromo-4-fluoro-2-methoxy-9H-xanthen-9-ol (40 g, 123 mmol) as a light yellow solid that was advanced without further purification.

Step 2: 7-Bromo-4-fluoro-2-methoxy-9H-xanthen-9-ol (40 g, 123 mmol) and dioxane (400 ml) were combined in 1 L RBF and thionyl chloride (26.9 ml, 369 mmol) was slowly added. The solution was stirred at RT for 30 minutes, then heated to 75° C. for one hour. The solution was concentrated and used in the next step without further purification.

Step 3: 7-Bromo-9-chloro-4-fluoro-2-methoxy-9H-xanthene (45 g, 131 mmol) was dissolved in saturated solution ammonia in dioxane (1310 mL, 655 mmol) and stirred for 60 hrs at RT. The solution was concentrated in vacuo. The material was treated with saturated aqueous sodium carbonate and extracted into EtOAc. The organic extracts were concentrated. The product was purified from the concentrate via silica gel column chromatography (RediSep 330 g column) using 10-100% EtOAc in hexane to afford 7-bromo-4-fluoro-2-methoxy-9H-xanthen-9-amine (10 g, 30:9 mmol).

Step 4: 7-Bromo-4-fluoro-2-methoxy-9H-xanthen-9-amine (3.5 g, 10.80 mmol) and Hünig's base (3.77 ml, 21.60 mmol) were dissolved in toluene (75 ml). The solution was cooled to 0° C. and thiophosgene (0.828 ml, 10.80 mmol) was added in one portion. The solution was stirred for 15 minutes and allowed to warm to RT. The solution was then filtered under inert atmosphere, and the solids were washed with 25 mL of toluene.

Step 5: The toluene solution from Step 4 was cooled to −78° C. and carbon disulfide (1.440 ml, 23.89 mmol) was added. This solution was then added at −78° C. using a canula to a solution of potassium tert-butoxide in THF (1M) (11.95 ml, 11.95 mmol) and THF 50 mL at −78° C. The mixture was stirred for 15 minutes and then allowed to warm to RT and stirred for 1 hour. The solution was then quenched with water and extracted into EtOAc. The extracts were combined, dried, filtered and concentrated to afford 7'-bromo-4'-fluoro-2'-methoxyspiro[thiazolidine-4,9'-xanthene]-2,5-dithione (4.23 g, 9.56 mmol), which crude product was used as is.

Step 6: Propane-1,3-diamine (4.12 mL, 47.8 mmol) and 7'-bromo-4'-fluoro-2'-methoxyspiro[thiazolidine-4,9'-xanthene]-2,5-dithione (4.23 g, 9.56 mmol) were combined in 50 ml of EtOH and heated to 65° C. for 30 minutes. The solution was then concentrated. The product was purified via silica gel column chromatography (RediSep 330 g column) using 0-50% EtOAc in hexane to afford 7'-bromo-4'-fluoro-2'-methoxy-3,4-dihydro-2H-spiro[imidazo[1,5-a]pyrimidine-8,9'-xanthene]-6(7H)-thione (1.0 g, 2.231 mmol) as an off white solid. MS m/z=448.0 [M+H].

Step 7: Tert-butyl hydroperoxide (70% in water) (1.945 mL, 20.08 mmol), ammonium hydroxide (13.03 mL, 335 mmol), and 7'-bromo-4'-fluoro-2'-methoxy-3,4-dihydro-2H-spiro[imidazo[1,5-a]pyrimidine-8,9'-xanthene]-6(7H)-thione (300 mg, 0.669 mmol) were combined in MeOH (50 mL) and stirred at RT overnight. The solution was concentrated. The product was purified from the crude concentrate via silica gel column chromatography (RediSep 40 g column) using 0-100% 90/10/1 (DCM/MeOH/ammonia) in DCM to afford 7'-bromo-4'-fluoro-2'-methoxy-3,4-dihydro-2H-spiro[imidazo[1,5-a]pyrimidine-8,9'-xanthen]-6-amine (150 mg, 0.348 mmol). MS m/z=431.0 [M+H].

Step 9: Potassium carbonate (1M aq. Solution) (1.391 mL, 1.391 mmol), 2-fluoropyridin-3-ylboronic acid (98 mg, 0.696 mmol), bis(di-tert-butyl(4-dimethylaminophenyl)phosine) dichloropalladium(II) (0.34 mmol) and 7'-bromo-4'-fluoro-2'-methoxy-3,4-dihydro-2H-spiro[imidazo[1,5-a]pyrimidine-8,9'-xanthen]-6-amine (150 mg, 0.348 mmol) were combined in dioxane (3 mL), capped under argon, and heated at 100° C. for 2 hours. The solution was concentrated, and the product was purified from the crude concentrate via silica gel column chromatography (RediSep 12 g column) using 0-100% 90/10/1 (DCM/MeOH/ammonia) in DCM to afford 4'-fluoro-7'-(2-fluoropyridin-3-yl)-2'-methoxy-3,4-dihydro-2H-spiro[imidazo[1,5-a]pyrimidine-8,9'-xanthen]-6-amine (30 nig, 0.067 mmol). MS m/z=449.2 [M+H].

The following compounds in Table I are additional representative examples of compounds of Formulas I, II and III, and sub-formulas thereof, provided by the present invention. The methods used to prepare exemplary compounds 8A, 8B, 9A and 9B as well as 10-17 are included in Table 1, and correspond to those described in the Examples 5-9 herein above. Table I further provides the mass and biological data (average nM $IC_{50}$'s for the enzyme and cell assays, provided in a range) for each compound, where available.

TABLE 1

| Example No | Compound Structure | Compound Name | Observed MW | Method | BACE 1 FRET assay (uM) | HEK cell assay (uM) |
|---|---|---|---|---|---|---|
| 11 | 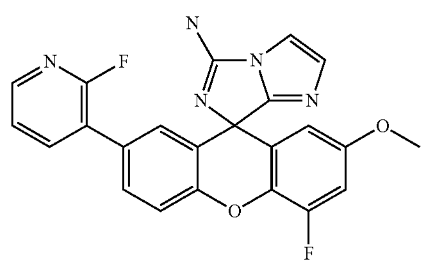 [SMILES: COc1cc(F)c2c(c1)C1(N=C(N)n3ccnc31)c1cc(-c3cccnc3F)ccc1O2] | 4'-fluoro-7'-(2-fluoro-3-pyridinyl)-2'-methoxyspiro[imidazo[1,5-a]imidazole-7,9'-xanthen]-5-amine | 432 | A1 | 0.009 | 0.058 |
| 8A | 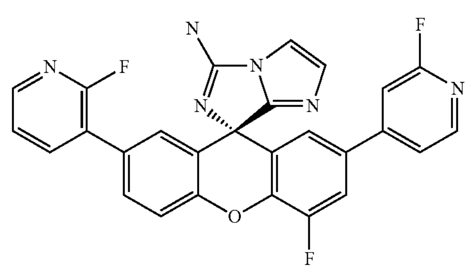 [SMILES: NC1=N[C@]2(c3cc(-c4cccnc4F)ccc3Oc3c(F)cc(-c4ccnc(F)c4)cc32)c2nccn21] | (7S)-4'-fluoro-7'-(2-fluoro-3-pyridinyl)-2'-(2-fluoro-4-pyridinyl)spiro[imidazo[1,5-a]imidazole-7,9'-xanthen]-5-amine | 497 | A3 | 0.010 | 0.138 |
| 8B | 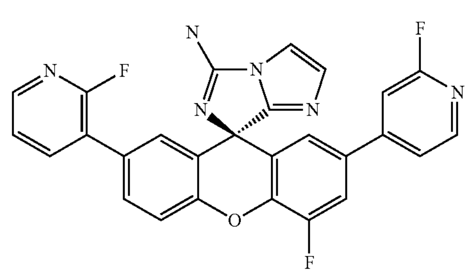 [SMILES: NC1=N[C@@]2(c3cc(-c4cccnc4F)ccc3Oc3c(F)cc(-c4ccnc(F)c4)cc32)c2nccn21] | (7R)-4'-fluoro-7'-(2-fluoro-3-pyridinyl)-2'-(2-fluoro-4-pyridinyl)spiro[imidazo[1,5-a]imidazole-7,9'-xanthen]-5-amine | 497 | A3 | 0.0003 | 0.086 |

TABLE 1-continued

| Example No | Compound Structure | Compound Name | Observed MW | Method | BACE 1 FRET assay (uM) | HEK cell assay (uM) |
|---|---|---|---|---|---|---|
| 12 | 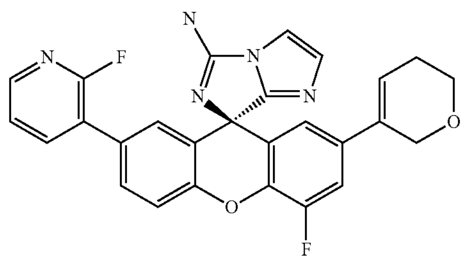 | (7R)-2'-(5,6-dihydro-2H-pyran-3-yl)-4'-fluoro-7'-(2-fluoro-3-pyridinyl)spiro[imidazo[1,5-a]imidazole-7,9'-xanthen]-5-amine | 484 | A3 | 0.023 | 0.173 |
| 13 | 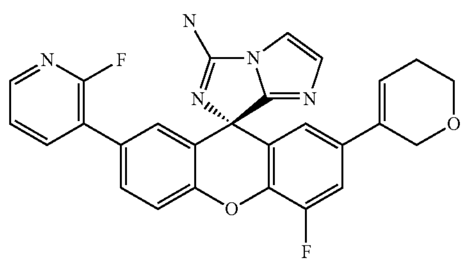 | (7S)-2'-(5,6-dihydro-2H-pyran-3-yl)-4'-fluoro-7'-(2-fluoro-3-pyridinyl)spiro[imidazo[1,5-a]imidazole-7,9'-xanthen]-5-amine | 484 | A3 | 0.0004 | 0.029 |
| 14 | 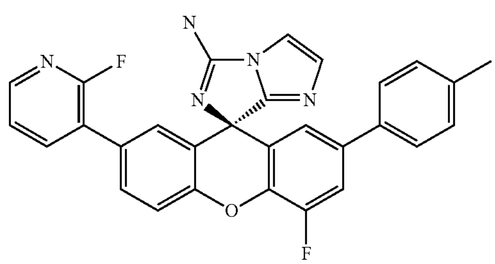 [SMILES: Cc1ccc(-c2cc(F)c3c(c2)[C@]2(N=C(N)n4ccnc42)c2cc(-c4cccnc4F)ccc2O3)cc1] | (7R)-4'-fluoro-7'-(2-fluoro-3-pyridinyl)-2'-(4-methylphenyl)spiro[imidazo[1,5-a]imidazole-7,9'-xanthen]-5-amine | 492 | A3 | 0.114 | 4.16 |
| 15 | 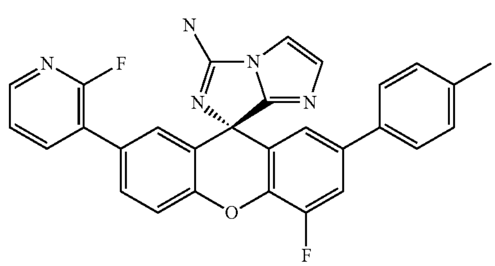 [SMILES: Cc1ccc(-c2cc(F)c3c(c2)[C@@]2(N=C(N)n4ccnc42)c2cc(-c4cccnc4F)ccc2O3)cc1] | (7S)-4'-fluoro-7'-(2-fluoro-3-pyridinyl)-2'-(4-methylphenyl)spiro[imidazo[1,5-a]imidazole-7,9'-xanthen]-5-amine | 492 | A3 | 0.0004 | 0.028 |
| 9B | 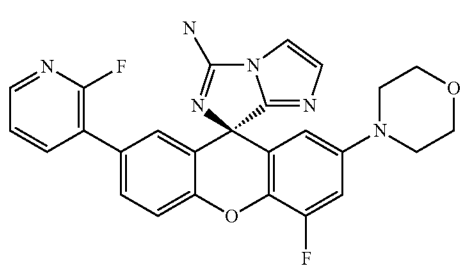 [SMILES: NC1=N[C@@]2(c3cc(-c4cccnc4F)ccc3Oc3c(F)cc(N4CCOCC4)cc32)c2nccn21] | (7R)-4'-fluoro-7'-(2-fluoro-3-pyridinyl)-2'-(4-morpholinyl)spiro[imidazo[1,5-a]imidazole-7,9'-xanthen]-5-amine | 487 | A4 | 0.0007 | 0.031 |

TABLE 1-continued

| Example No | Compound Structure | Compound Name | Observed MW | Method | BACE 1 FRET assay (uM) | HEK cell assay (uM) |
|---|---|---|---|---|---|---|
| 9A | 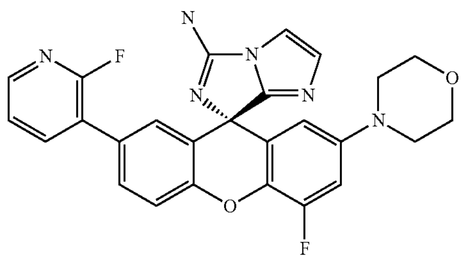 [SMILES: NC1=N[C@]2(c3cc(-c4cccnc4F)ccc3Oc3c(F)cc(N4CCOCC4)cc32)c2nccn21] | (7S)-4'-fluoro-7'-(2-fluoro-3-pyridinyl)-2'-(4-morpholinyl)spiro[imidazo[1,5-a]imidazole-7,9'-xanthen]-5-amine | 487 | A4 | 0.189 | 3.97 |
| 16 | 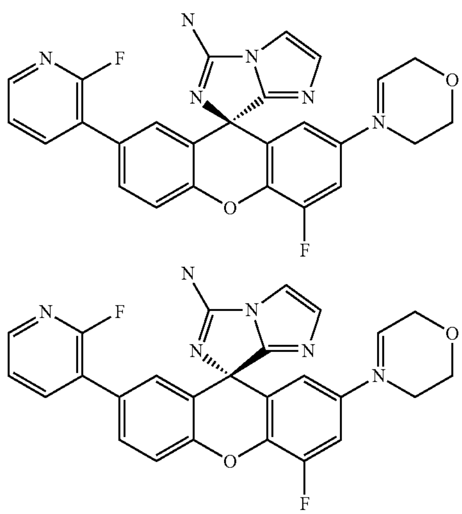 | (7R)-2'-(3,6-dihydro-2H-pyran-4-yl)-4'-fluoro-7'-(2-fluoro-3-pyridinyl)spiro[imidazo[1,5-a]imidazole-7,9'-xanthen]-5-amine, (7S)-2'-(3,6-dihydro-2H-pyran-4-yl)-4'-fluoro-7'-(2-fluoro-3-pyridinyl)spiro[imidazo[1,5-a]imidazole-7,9'-xanthen]-5-amine | 484 | A3 | 0.0006 | 0.039 |
| 17 | 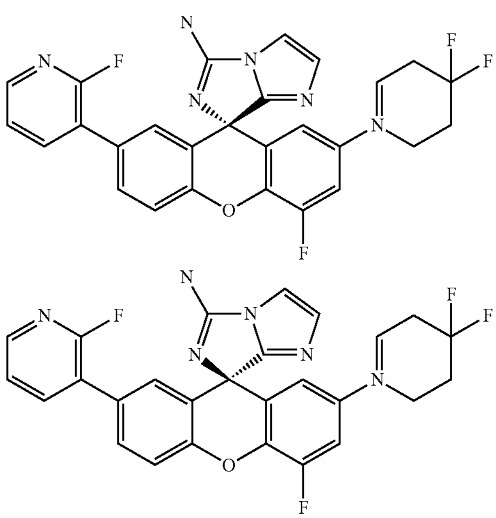 | (7R)-2'-(4,4-difluoro-1-piperidinyl)-4'-fluoro-7'-(2-fluoro-3-pyridinyl)spiro[imidazo[1,5-a]imidazole-7,9'-xanthen]-5-amine, (7S)-2'-(4,4-difluoro-1-piperidinyl)-4'-fluoro-7'-(2-fluoro-3-pyridinyl)spiro[imidazo[1,5-a]imidazole-7,9'-xanthen]-5-amine | 521 | A4 | 0.0007 | 0.051 |

TABLE 1-continued

| Example No | Compound Structure | Compound Name | Observed MW | Method | BACE 1 FRET assay (uM) | HEK cell assay (uM) |
|---|---|---|---|---|---|---|
| 10 | | (7S)-4'-fluoro-7'-(2-fluoropyridin-3-yl)-2'-methoxy-3,4-dihydro-2H-spiro[imidazo[1,5-a]pyrimidine-8,9'-xanthen]-6-amine (7R)-4'-fluoro-7'-(2-fluoropyridin-3-yl)-2'-methoxy-3,4-dihydro-2H-spiro[imidazo[1,5-a]pyrimidine-8,9'-xanthen]-6-amine | 448 | A5 | 0.022 | 0.078 |

The following compounds in Table 2 are additional representative examples of Formulas I-III provided by the present invention.

TABLE 2

| Ex. No. | $R^2$ | $A^3$ | $A^4$ | $R^7$ | —X—Y— |
|---|---|---|---|---|---|
| 18 | 3,6-dihydro-2H-pyran-3-yl | CH | N | 2-Fluoropyridin-3-yl | —CH=CH— |
| 19 | 2,2-dimethyl-propanenitrile-oxyl | CH | N | 2-Fluoropyridin-3-yl | —CH$_2$—CH$_2$— |
| 20 | 3-methyl-e-oxetane-methoxyl | CH | CH | 2-Fluoropyridin-3-yl | —CH=CH— |
| 21 | 2-methyl-1H-pyrazolyl- | CH | CH | 2-Fluoropyridin-3-yl | —CH$_2$—CH$_2$— |
| 22 | 3,6-dihydro-2H-pyran-4-yl | CH | N | 2-Fluoropyridin-3-yl | —CH=CH— |
| 23 | 2-F-pyrrolidin-1-yl | CH | N | 2-Fluoropyridin-3-yl | —CH=N— |
| 24 | 3,6-dihydro-2H-pyran-4-yl | CH | N | 2-Fluoropyridin-3-yl | —CH=CH— |
| 25 | 2,3-dimethyl-3,6-dihydro-2H-pyran-4-yl | CF | N | 2-Fluoropyridin-3-yl | —N=CH$_2$— |
| 26 | 3-methyl-3-oxetanyl-ethynyl | CF | N | 2-Fluoropyridin-3-yl | —CH=CH— |
| 27 | 3,6-dihydro-2H-pyran-3-yl | CF | N | 2-Fluoropyridin-3-yl | —CH=CH— |
| 28 | 2,2-dimethyl-propanenitrile-oxyl | CF | N | 2-Fluoropyridin-3-yl | —CH$_2$—CH$_2$— |
| 29 | 3-methyl-e-oxetane-methoxyl | CF | N | 2-Fluoropyridin-3-yl | —CH=CH— |
| 30 | 3-methyl-1H-pyrazolyl- | CF | N | 2-Fluoropyridin-3-yl | —CH$_2$—CH$_2$— |
| 31 | 3,6-dihydro-2H-pyran-4-yl | CF | N | 2-Fluoropyridin-3-yl | —CH=CH— |
| 32 | 2-F-pyrrolidin-1-yl | CF | N | 2-Fluoropyridin-3-yl | —N=CH$_2$— |
| 33 | 3,6-dihydro-2H-pyran-4-yl | CF | N | pyridin-3-yl | —CH=CH— |
| 34 | 2,3-dimethyl-3,6-dihydro-2H-pyran-4-yl | CF | N | 2-Fluoropyridin-3-yl | —CH$_2$—CH$_2$— |
| 35 | 3-methyl-3-oxetanyl-ethynyl | CF | N | 2-Fluoropyridin-3-yl | —CH=CH— |
| 36 | 3,6-dihydro-2H-pyran-3-yl | CF | N | 2-Fluoropyridin-3-yl | —CH$_2$—CH$_2$— |
| 37 | 2,2-dimethyl-propanenitrile-oxyl | CF | N | 2-Fluoropyridin-3-yl | —CH=CH— |

The present invention also provides methods for making compounds of Formulas I-III, and sub-formulas therein. For example, the compounds in Table 2 and additional examples may be made by the following methods, as similarly described in the literature references mentioned below.

In one embodiment of the invention, there is provided a method of making a compound of Formula I (defined herein), the method comprising the step of reacting a compound 20

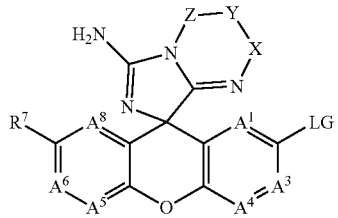

wherein $A^1$, $A^3$, $A^4$, $A^5$, $A^6$, $A^8$, $R^7$, X, Y and Z of Formula I are as defined herein and LG is a leaving group that is a halogen selected from a bromine (Br) or chlorine (Cl) or —O—S(=O)$_2$CF$_3$, with a compound having the structure

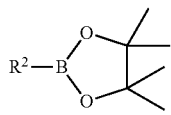

or $R^2$—B(OH)$_2$, wherein $R^2$ is as defined herein, to make a compound of Formula I.

In another embodiment of the invention, there is provided a method of making a compound of Formula II, the method comprising the step of reacting a compound 20

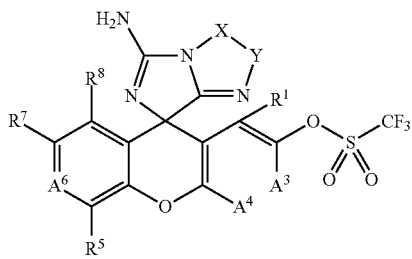

wherein $R^1$, $A^3$, $A^4$, $R^5$, $A^6$, $R^7$, $R^8$, X and Y of Formula II are as defined herein, with a compound having the structure

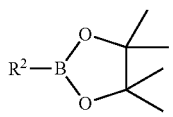

or $R^2$—B(OH)$_2$, wherein $R^2$ is as defined herein, to make a compound of Formula II.

In another embodiment of the invention, there is provided a method of making a compound of Formula II-B, the method comprising the step of reacting a compound 20

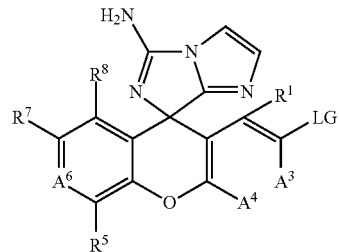

wherein $A^1$, $A^3$, $A^4$, $A^5$, $A^6$, $A^8$, $R^7$, $R^8$, X and Y of Formula II-B are as defined herein and LG is a leaving group that is a halogen selected from a bromine (Br) or chlorine (Cl) or —O—S(=O)$_2$CF$_3$, with a compound having the structure

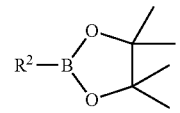

or $R^2$—B(OH)$_2$, wherein $R^2$ is as defined herein, to make a compound of Formula II-B.

In another embodiment of the invention, there is provided a method of making a compound of Formula III, the method comprising the step of reacting a compound 20

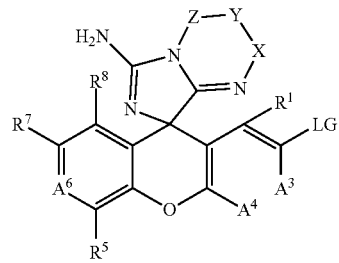

wherein $A^1$, $A^3$, $A^4$, $A^5$, $A^6$, $A^8$, $R^7$, $R^8$, X and Y of Formula III are as defined herein and LG is a leaving group that is a halogen selected from a bromine (Br) or chlorine (Cl) or —O—S(=O)$_2$CF$_3$, with a compound having the structure

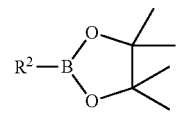

or $R^2$—B(OH)$_2$, wherein $R^2$ is as defined herein, to make a compound of Formula III.

As can be appreciated by the skilled artisan, the above synthetic schemes and representative examples are not intended to comprise a comprehensive list of all means by which the compounds described and claimed in this application may be synthesized. Further methods will be evident to those of ordinary skill in the art. Additionally, the various synthetic steps described above may be performed in an alternate sequence or order to give the desired compounds.

For example, in these procedures, the steps may be preceded, or followed, by additional protection/deprotection steps as necessary. Particularly, if one or more functional groups, for example carboxy, hydroxy, amino, or mercapto groups, are or need to be protected in preparing the compounds of the invention, because they are not intended to take part in a specific reaction or chemical transformation, various known conventional protecting groups may be used. For example, protecting groups typically utilized in the synthesis of natural and synthetic compounds, including peptides, nucleic acids, derivatives thereof and sugars, having multiple reactive centers, chiral centers and other sites potentially susceptible to the reaction reagents and/or conditions, may be used.

Synthetic chemistry transformations and protecting group methodologies (protection and deprotection) useful in synthesizing the inhibitor compounds described herein are known in the art and include, for example, those such as described in R. Larock, Comprehensive Organic Transformations, VCH Publishers (1989); T. W. Greene and P. G. M. Wuts, Protective Groups in Organic Synthesis, $3^{rd}$ edition, John Wiley and Sons (1999); L. Fieser and M. Fieser, Fieser and Fieser's Reagents for Organic Synthesis, John Wiley and Sons (1994); A. Katritzky and A. Pozharski, Handbook of Heterocyclic Chemistry, $2^{nd}$ edition (2001); M. Bodanszky, A. Bodanszky, The Practice of Peptide Synthesis, Springer-Verlag, Berlin Heidelberg (1984); J. Seyden-Penne, Reductions by the Alumino- and Borohydrides in Organic Synthesis, $2^{nd}$ edition, Wiley-VCH, (1997); and L. Paquette, editor, Encyclopedia of Reagents for Organic Synthesis, John Wiley and Sons (1995).

Salts, including pharmaceutically acceptable salts, of a compound of the invention having a salt-forming group may be prepared in a conventional manner or manner known to persons skilled in the art. For example, acid addition salts of compounds of the invention may be obtained by treatment with an acid or with a suitable anion exchange reagent. A salt with two acid molecules (for example a dihalogenide) may also be converted into a salt with one acid molecule per compound (for example a monohalogenide); this may be done by heating to a melt, or for example by heating as a solid under a high vacuum at elevated temperature, for example from 50° C. to 170° C., one molecule of the acid being expelled per molecule of the compound.

Acid salts can usually be converted to free-base compounds, e.g. by treating the salt with suitable basic agents, for example with alkali metal carbonates; alkali metal hydrogen carbonates, or alkali metal hydroxides, typically potassium carbonate or sodium hydroxide. Exemplary and suitable salts, and their preparation, are described herein in the Definition section of the application.

All synthetic procedures described herein can be carried out under known reaction conditions, advantageously under those described herein, either in the absence or in the presence (usually) of solvents or diluents. As appreciated by those of ordinary skill in the art, the solvents should be inert with respect to, and should be able to dissolve, the starting materials and other reagents used. Solvents should be able to partially or wholly solubilize the reactants in the absence or presence of catalysts, condensing agents or neutralizing agents, for example ion exchangers, typically cation exchangers for example in the $H^+$ form. The ability of the solvent to allow and/or influence the progress or rate of the reaction is generally dependant on the type and properties of the solvent(s), the reaction conditions including temperature, pressure, atmospheric conditions such as in an inert atmosphere under argon or nitrogen, and concentration, and of the reactants themselves.

Suitable solvents for conducting reactions to synthesize compounds of the invention include, without limitation, water; esters, including lower alkyl-lower alkanoates, e.g., EtOAc; ethers including aliphatic ethers, e.g., $Et_2O$ and ethylene glycol dimethylether or cyclic ethers, e.g., THF; liquid aromatic hydrocarbons, including benzene, toluene and xylene; alcohols, including MeOH, EtOH, 1-propanol, IPOH, n- and t-butanol; nitriles including $CH_3CN$; halogenated hydrocarbons, including $CH_2Cl_2$, $CHCl_3$ and $CCl_4$; acid amides including DMF; sulfoxides, including DMSO; bases, including heterocyclic nitrogen bases, e.g. pyridine; carboxylic acids, including lower alkanecarboxylic acids, e.g., AcOH; inorganic acids including HCl, HBr, HF, $H_2SO_4$ and the like; carboxylic acid anhydrides, including lower alkane acid anhydrides, e.g., acetic anhydride; cyclic, linear, or branched hydrocarbons, including cyclohexane, hexane, pentane, isopentane and the like, and mixtures of these solvents, such as purely organic solvent combinations, or water-containing solvent combinations e.g., aqueous solutions. These solvents and solvent mixtures may also be used in "working-up" the reaction as well as in processing the reaction and/or isolating the reaction product(s), such as in chromatography.

Purification methods are known in the art and include, for example, crystallization, chromatography (liquid and gas phase, and the like), extraction, distillation, trituration, reverse phase HPLC and the like. Reactions conditions such as temperature, duration, pressure, and atmosphere (inert gas, ambient) are known in the art and may be adjusted as appropriate for the reaction.

The invention further encompasses "intermediate" compounds, including structures produced from the synthetic procedures described, whether isolated or generated in-situ and not isolated, prior to obtaining the finally desired compound. Structures resulting from carrying out steps from a transient starting material, structures resulting from divergence from the described method(s) at any stage, and structures forming starting materials under the reaction conditions are all "intermediates" included in the invention. Further, structures produced by using starting materials in the form of a reactive derivative or salt, or produced by a compound obtainable by means of the process according to the invention and structures resulting from processing the compounds of the invention in situ are also within the scope of the invention.

The invention also provides new starting materials and/or intermediates, as well as processes for the preparation thereof. In select embodiments, such starting materials are used and reaction conditions so selected as to obtain the desired compound(s). Starting materials of the invention, are either known, commercially available, or can be synthesized in analogy to or according to methods that are known in the art. Many starting materials may be prepared according to known processes and, in particular, can be prepared using processes described in the examples. In synthesizing starting materials, functional groups may be protected with suitable protecting groups when necessary. Protecting groups, their introduction and removal are described above.

Compounds of the present invention can possess, in general, one or more asymmetric carbon atoms and are thus capable of existing in the form of optical isomers as well as in the form of racemic or non-racemic mixtures thereof. While shown without respect to stereochemistry in Formulas I-III, the present invention includes such optical isomers and diastereomers, as well as the racemic and resolved, enantiomerically pure R and S stereoisomers, as well as other mixtures of R and S stereoisomers and pharmaceutically acceptable salts thereof.

The optical isomers can be obtained by resolution of the racemic mixtures according to conventional processes, e.g., by formation of diastereoisomeric salts, by treatment with an optically active acid or base. Examples of appropriate acids are tartaric, diacetyltartaric, dibenzoyltartaric, ditoluoyltartaric, and camphorsulfonic acid and then separation of the mixture of diastereoisomers by crystallization followed by liberation of the optically active bases from these salts. A different process for separation of optical isomers involves the use of a chiral chromatography column optimally chosen to maximize the separation of the enantiomers. Still another available method involves synthesis of covalent diastereoisomeric molecules by reacting compounds of the invention with an optically pure acid in an activated form or an optically pure isocyanate. The synthesized diastereoisomers can be separated by conventional means such as chromatography, distillation, crystallization or sublimation, and then hydrolyzed to deliver the enantiomerically pure compound. The optically active compounds of the invention can likewise be obtained by using optically active starting materials. These isomers may be in the form of a free acid, a free base, an ester or a salt. All such isomeric forms of such compounds are expressly included in the present invention.

The compounds of the invention may also be represented in multiple tautomeric forms. Tautomers often exist in equilibrium with each other, and interconvert under environmental and physiological conditions. The compounds of the invention may also occur in cis- or trans- or E- or Z-double bond isomeric forms. The invention expressly includes all tautomeric forms of the compounds described herein.

All crystal forms of the compounds described herein are expressly included in the present invention.

The present invention also includes isotopically-labeled compounds, which are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, fluorine and chlorine, such as $^{2}H$ (deuterium), $^{3}H$ (tritium), $^{13}C$, $^{14}C$, $^{15}N$, $^{16}O$, $^{17}O$, $^{31}P$, $^{32}P$, $^{35}S$, $^{18}F$ and $^{36}Cl$.

Compounds of the present invention that contain the aforementioned isotopes and/or other isotopes of other atoms are within the scope of this invention. Certain isotopically-labeled compounds of the present invention, for example those into which radioactive isotopes such as $^{3}H$ and $^{14}C$ are incorporated, are useful in drug and/or substrate tissue distribution assays. Deuterated ($^{2}H$), Tritiated ($^{3}H$) and carbon-14, i.e., $^{14}C$, isotopes are particularly preferred for their ease of preparation and detection. Further, substitution with heavier isotopes such as deuterium, i.e., $^{2}H$, can afford certain therapeutic advantages resulting from greater metabolic stability, for example increased in vivo half-life or reduced dosage requirements and, hence, may be preferred in some circumstances. Isotopically labeled compounds of this invention can generally be prepared by substituting a readily available isotopically labeled reagent for a non-isotopically labeled reagent.

Biological Evaluation

The compounds of the invention may be modified by appending appropriate functionalities to enhance selective biological properties. The pharmacokinetic and pharmacodynamic properties of a compound relate, directly and indirectly, to the ability of the compound to be effective for its intended use.

Although the pharmacological properties of the compounds of the invention (Formulas I-III) vary with structural change, in general, activity possessed by compounds of Formulas I-III may be demonstrated both in vitro as well as in vivo. The following exemplified pharmacological assays have been carried out with the compounds according to the invention, to assess and characterize the compound's ability to modulate BACE activity and to regulate the cleavage of amyloid beta precursor protein, thereby reducing or inhibiting the production of amyloid beta.

In Vitro Enzymatic BACE FRET (Fluorescence Resonance Energy Transfer) Assay (Enzyme Assay Data in the Example Table I)

The assay buffer used in this screen is 0.05 M acetate, pH 4.2, 10% DMSO final, 100 uM genapol (which is a nonionic detergent, below its Critical Micelle Concentration). The Beta Secretase enzyme (0.2 nM) is pre-incubated for one hour with inhibitors, typically in about 1 uL of DMSO according to a serial dilution, are added thereto. This assay is effectively started by the addition of FRET substrate (50 nM) and the combination is incubated for one hour. The FRET assay is terminated with by addition of Tris buffer, which raises the pH to neutrality, and the fluorescence is determined. The FRET substrate is a peptide with commercially available fluorophore and quencher, on opposite sides of the BACE cleavage site. Proteolytic cleavage of the FRET substrate releases quenching of fluorescence (excitation 488 nm and emission 425 nm).

Where available, the in-vitro BACE FRET enzyme data for each of the Examples is provided in Table I.

In Vitro BACE Cell-Based Assay

The cell-based assay measures inhibition or reduction of Aβ40 in conditioned medium of test compound treated cells expressing amyloid precursor protein.

Cells stably expressing Amyloid Precursor Protein (APP) were plated at a density of 40K cells/well in 96 well plates (Costar). The cells were cultivated for 24 hours at 37° C. and 5% $CO_2$ in DMEM supplemented with 10% FBS. The test compounds were then added to cells in 10-point dose response concentrations with the starting concentration being either 100 μM or 10 μM. The compounds were diluted from stock solutions in DMSO and the final DMSO concentration of the test compounds on cells was 0.1%. After 24 h of incubation with the test compounds the supernatant conditioned media was collected and the Aβ 40 levels were determined using a sandwich ELISA. The $IC_{50}$ of the compound was calculated from the percent of control or percent inhibition of Aβ 40 as a function of the concentration of the test compound.

The sandwich ELISA to detect Aβ 40 was performed in 96 well microtiter plates, which were pre-treated with goat anti-rabbit IgG (Pierce). The capture and detecting antibody pair that were used to detect Aβ 40 from cell supernatants were affinity purified pAb40 (Biosource) and biotinylated 6E10 (Signet Labs Inc.), respectively. The optimal Concentration for the pAb40 antibody was 3 μg/m in Superblock/dTBS (Pierce) that was supplemented with 0.05% Tween 20 (Sigma). Optimal concentration for the detection antibody 6E10-biotinylated was 0.5 μg/ml in Superblock/TBS (Pierce) that had been supplemented with 2% normal goat serum and 2% normal mouse serum.

Cellular supernatants were incubated with the capture antibody for 3 h at 4° C., followed by 3 wash steps in TBS-tween (0.05%). The detecting antibody incubation was for 2 h at 4° C., again followed by the wash steps as described previously. The final readout of the ELISA is Time-Resolved Fluorescence (counts per minute) using Delfia reagents Streptavidin-Europium and Enhancement solutions (Perkin Elmer) and the Victor 2 multilabel counter (Perkin Elmer).

Where available, the in-vitro BACE cell based data for each of the Examples is provided in Table I.

In Vivo Inhibition of Beta-Secretase

Several animal models, including mouse, rat, dog, and monkey, may be used to screen for inhibition of beta-secretase activity in vivo following administration of a test compound sample. Animals used in this invention can be wild type, transgenic, or gene knockout animals. For example, the Tg2576 mouse model, prepared and conducted as described in Hsiao et al., 1996, Science 274, 99-102, and other non-transgenic or gene knockout animals are useful to analyze in vivo inhibition of Amyloid beta peptide (Abeta) production in the presence of inhibitory test compounds. Generally, 2 to 18 month old Tg2576 mice, gene knockout mice or non-transgenic animals are administered test compounds formulated in vehicles, such as cyclodextran, phosphate buffers, hydroxypropyl methylcellulose or other suitable vehicles. One to twenty-four hours following the administration of compound, animals are sacrificed, and brains as well as cerebrospinal fluid (CSF) and plasma are removed for analysis of A-beta levels and drug or test compound concentrations (Dovey et al., 2001, Journal of Neurochemistry, 76,173-181) Beginning at time 0, animals are administered by oral gavage, or other means of delivery such as intravenous injection, an inhibitory test compound of up to 100 mg/kg in a standard, conventional formulation, such as 2% hydroxypropyl methylcellulose, 1% Tween80. A separate group of animals receive 2% hydroxypropyl methylcellulose, 1% Tween80 alone, containing no test compound, and serve as a vehicle-control group. At the end of the test period, animals are sacrificed and brain tissues, plasma or cerebrospinal fluid are collected. Brains are either homogenized in 10 volumes (w/v) of 0.2% diethylamine (DEA) in 50 mM NaCl (Best et al., 2005, Journal of Pharmacology and Experimental Therapeutics, 313, 902-908), or in 10 volumes of 0.5% TritonX-100 in Tris-buffered saline (pH at about 7.6). Homogenates are centrifuged at 355,000 g, 4° C. for 30 minutes. CSF or brain supernatants are then analyzed for the presence of A-beta peptide by specific sandwich ELISA assays based on ECL (Electrochemiluminescence) technology. For example, rat Abeta40 is measured using biotinylated-4G8 (Signet) as a capture antibody and Fab40 (an in-house antibody specific to the C-terminal of Abeta40) as a detection antibody. For example, 4 hours after administration of 30 mg/kg oral dose of the test compound in 2% hydroxypropyl methylcellulose, 1% Tween80 (pH2.2) to 200 g male Sprague Dawley rats, amyloid beta peptide levels are measured for reduction by X % and Y % in cerebrospinal fluid and brain, respectively, when compared to the levels measured in the vehicle-treated or control mice.

Actual vehicles used: Oral: 2% HPMC, 1% Tween80, pH 2.2
IV: 5% EtOH, 45% Propylene glycol in 5% Dextrose The compounds of the invention may be shown to reduce the formation and/or deposition of amyloid beta peptide in the cerebrospinal fluid (CSF) as well as in the brain of a mouse or rat at both 10 mpk (mpk=mg compound per kg animal) and 30 mpk dosing concentrations after 4 hrs.

Indications

De Meyer et al re-affirm the believed role which the accumulation of beta-amyloid protein (A-beta) in cerebral spinal fluid (CSF) in a subject plays in the progression of symptoms, initially revealed as mild cognitive impairment, which ultimately leads to AD. Arch Neural. 67(8):949-956, 2010. Amyloid-b (Ab) peptides generated from amyloid precursor protein (APP) by proteolytic cleavage, such as by aspartyl protease enzymes including beta-secreatase (BACE) and gamma-secretase, likely play a causal role in AD pathogenesis (Tanzi and Bertram, Cell, (120): 545-555, 2005; Walsh and Selkoe, Neuron, (44): 181-193, 2004). Although the precise mechanisms of Ab toxicity are unclear, oligomeric forms of Ab may contribute to cognitive decline by altering synaptic structure and function (Palop and Mucke, Nat. Neuroscience, (13): 812-818, 2010; Selkoe, Behavioral Brain Res., (192): 106-113, 2008; Shankar et al., Nat. Medicine (14): 837-842, 2008). Transgenic mouse models that overexpress mutant APP and produce high levels of Ab show amyloid plaque deposition, synaptic deficits, learning and memory impairments, and other behavioral abnormalities (Games et al., Nature, (373): 523-527, 1995; Go⁻ tz et al., Molecular Psychiatry (9): 664-683, 2004; Hsia et al., Proc. Natl. Academy of Science USA (96): 3228-3233, 1999; Hsiao et al., Science (274): 99-102, 1996, citing Harris et al, Neuron (68): 428-441, 2010).

Molecules which target the activities of either beta secreatese and gamma secretase are undergoing human clinical trials/studies as potential treatments of Alzheimer's Disease (AD) and other cognitive impairments and cognitive deficits. Bapineuzamab, a monoclonal amino-terminus specific anti-amyloid antibody is presently in Phase III clinical trials for the treatment of AD. Alzheimer's Research & Therapy, 1:2, 2009. Each of the known genetic causes of AD is linked to A-beta. Dementia, Down's Syndrome to APP over-production, are all believed to be linked to the deposition of A-beta on the brain. With methods for identifying brain amyloid deposition, positron emission scanning (PET) and CSF measurements of Ab42, identification of AD suffering individuals needing treatment is becoming easier and more common. It is firmly believed that by reducing the formation of A-beta, one can begin to pre-treat AD. Vassar et al, Journal of Neuroscience, 29 (41):12787-12794, 2009. One published pathway for treatment of AD is inhibition of beta-secretase. Tirrell, Bloomberg News, The Boston Globe, Jan. 7, 2010.

The US biotech company CoMentis is developing an orally bioavailable small molecule CTS-21166, a highly potent, highly selective and efficacious brain-penetrating beta-secretase inhibitor. CoMentis successfully completed a Phase I study of CTS-21166 in healthy volunteers in 2008. Results indicated that CTS-21166 was safe, well-tolerated and pharmacodynamically active at all dose levels. All clinical subjects administered CTS-21166 showed area-under-curve (AUC) reduction in plasma A-Beta40 reductions ranging from 40-75%. Because of the urgent need for AD treatment, Phase II studies for CTS-2166 are planned, or ongoing, for AD patients. In preclinical studies, CTS-21166 exhibits excellent efficacy, selectivity, brain penetration and pharmacologic activity.

BMS-708163, a potent, selective, brain penetrating, orally bioavailable gamma-secretase inhibitor developed by Bristol-Meyers Squibb, is a carboxamise-substituted sulfonamide small molecule, which is also notch (193×), amyloid-beta precursor protein selective, currently being studied in Ph II clinical trials for the treatment of AD in prodromal patients, or patients with profiles indicative of developing AD symptoms and related conditions. Gillman et al, *Med Chem Let*, accepted Feb. 28, 2010. BMS-708163 is also undergoing 11 other human clinical trials for safety, and/or efficacy relating to treatment of AD and/or various cognitive conditions relating to AD.

Solanezumab, a monoclonal antibody (LY-2062430) is being administered IV in a Ph II human clinical trial in patients with AD. Solanezumab targets the N-terminal of beta amyloid protein, one of the factors involved in disease pathogenisis. AD theory suggests that amyloid beta clumps together and eventually kills brain cells. Solanezumab binds specifically to soluble amyloid beta and thereby may draw the peptide away from the brain through the blood. Two Ph III trials are under way as a treatment to delay the progression of mild to moderate AD. Similarly, Roche RG4712, is a monoclonal anti-body currently undergoing human clinical trials, that are directed to eliminating amyloid beta from the CNS of AD patients, thereby providing an effective treatment for AD. *Roche Annual Report* 2009.

The compounds of the invention have been shown to modulate, and specifically inhibit the activity of the beta-secretase enzyme, thereby reducing the A-beta peptide fragments believed to be responsible for Alzheimer's Disease (AD). Accordingly, compounds of the invention are useful for; but not limited to, the prevention or treatment of beta-secretase related diseases, including Alzheimer's disease. The compounds of the invention have the ability to modulate the activity of beta secretase enzyme, thereby regulating the production of amyloid beta (Abeta peptide) and reducing the formation and deposition of Abeta peptide in both the cerebral spinal fluid as well as in the brain, resulting in a decrease of amyloid plaque on the brain. In one embodiment of the invention, there is provided a method of treating a disorder related to a beta-secretase enzyme in a subject, the method comprising administering to the subject an effective dosage amount of a compound of Formulas I, II, III, and sub-formulae thereof. In another embodiment, there is provided a method of reducing production of amyloid beta, and of reducing plaque formation on the brain. In another embodiment, there is provided a method for the treatment, prevention or amelioration of a disease or disorder characterized by the elevated beta-amyloid deposits or beta-amyloid levels in a subject, the method comprising administering to the subject a therapeutically effective amount of a compound according to any of Formulas I-III. In yet another embodiment, the invention provides a method of treating Alzheimer's disease, cognitive impairment including mild, moderate and/or severe, Down's Syndrome, cognitive decline, senile dementia, cerebral amyloid angiopathy or a neurodegenerative disorder.

Accordingly, the compounds of the invention would be useful in therapy as CNS agents in treating neurological disorders and related conditions in subjects.

Besides being useful for human treatment, the compounds of the invention may be useful for veterinary treatment of companion animals, exotic animals and farm animals, including mammals, rodents, and the like. For example, animals including horses, dogs, and cats may be treated with compounds provided herein:

Formulations and Method of Use

Treatment of diseases and disorders herein is intended to also include therapeutic administration of a compound of the invention, or a pharmaceutical salt thereof, or a pharmaceutical composition of either to a subject (i.e., an animal, preferably a mammal, most preferably a human) which may be in need of preventative treatment, such as, for example, for pain, inflammation and the like. Treatment also encompasses prophylactic administration of a compound of the invention, or a pharmaceutical salt thereof, or a pharmaceutical composition of either to a subject (i.e., an animal, preferably a mammal, most preferably a human). Generally, the subject is initially diagnosed by a licensed physician and/or authorized medical practitioner, and a regimen for prophylactic and/or therapeutic treatment via administration of the compound(s) or compositions of the invention is suggested, recommended or prescribed.

The amount of compound(s) which is/are administered and the dosage regimen for treating neurological disorders and beta-secretase mediated diseases with the compounds and/or compositions of this invention depends on a variety of factors, including the age, weight, sex and medical condition of the subject, the type of disease, the severity of the disease, the route and frequency of administration, and the particular compound employed. Thus, the dosage regimen may vary widely, but can be determined routinely using standard methods. A daily dose of about 0.01 to 500 mg/kg, advantageously between about 0.01 and about 50 mg/kg, more advantageously about 0.01 and about 30 mg/kg, and even more advantageously between about 0.1 and about 10 mg/kg body weight may be appropriate, and should be useful for all methods of use disclosed herein. The daily dose can be administered in one to four doses per day.

While it may be possible to administer a compound of the invention alone, in the methods described, the compound administered normally will be present as an active ingredient in a pharmaceutical composition. Thus, in another embodiment of the invention, there is provided a pharmaceutical composition comprising a compound of this invention in combination with a pharmaceutically acceptable excipient, which includes diluents, carriers, adjuvants and the like (collectively referred to herein as "excipient" materials) as described herein, and, if desired, other active ingredients. A pharmaceutical composition of the invention may comprise an "effective amount" of a compound of the invention or an "effective dosage amount" of a compound of the invention. An "effective dosage amount" of a compound of the invention includes an amount less than, equal to or greater than an effective amount of the compound. For example, a pharmaceutical composition in which two or more unit dosages, such as in tablets, capsules and the like, are required to administer an effective amount of the compound, or alternatively, a multi-dose pharmaceutical composition, such as powders, liquids and the like, in which an effective amount of the compound is administered by administering a portion of the composition.

The compound(s) of the present invention may be administered by any suitable route, preferably in the form of a pharmaceutical composition adapted to such a route, and in a dose effective for the treatment intended. The compounds and compositions of the present invention may, for example, be administered orally, mucosally, topically, rectally, pulmonarily such as by inhalation spray, or parentally including intravascularly, intravenously, intraperitoneally, subcutaneously, intramuscularly intrasternally and infusion techniques, in dosage unit formulations containing conventional pharmaceutically acceptable carriers, adjuvants, and vehicles.

For oral administration, the pharmaceutical composition may be in the form of, for example, a tablet, capsule, suspension or liquid. The pharmaceutical composition is preferably made in the form of a dosage unit containing a particular amount of the active ingredient. Examples of such dosage units are tablets or capsules. For example, these may contain an amount of active ingredient from about 1 to 2000 mg, advantageously from about 1 to 500 mg, and typically from about 5 to 150 mg. A suitable daily dose for a human or other mammal may vary widely depending on the condition of the patient and other factors; but, once again, can be determined using routine methods and practices.

For therapeutic purposes, the active compounds of this invention are ordinarily combined with one or more adjuvants or other "excipients" appropriate to the indicated route of administration. If orally administered on a per dose basis, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, to form the final formulation. For example, the active compound(s) and excipient(s) may be tableted or encapsulated by known and accepted methods for convenient administration. Examples of suitable formulations include, without limitation, pills, tablets, soft and hard-shell gel capsules, troches, orally-dissolvable forms and delayed or controlled-release formulations thereof. Particularly, capsule or tablet formulations may contain one or more controlled-release agents, such as hydroxypropylmethyl cellulose, as a dispersion with the active compound(s).

Formulations for parenteral administration may be in the form of aqueous or non-aqueous isotonic sterile injection solutions or suspensions. These solutions and suspensions may be prepared from sterile powders or granules using one or more of the carriers or diluents mentioned for use in the formulations for oral administration or by using other suitable dispersing or wetting agents and suspending agents. The compounds may be dissolved in water, polyethylene glycol, propylene glycol, ethanol, corn oil, cottonseed oil, peanut oil, sesame oil, benzyl alcohol, sodium chloride, tragacanth gum, and/or various buffers. Other adjuvants and modes of administration are well and widely known in the pharmaceutical art. The active ingredient may also be administered by injection as a composition with suitable carriers including saline, dextrose, or water, or with cyclodextrin (ie. Captisol), cosolvent solubilization (ie. propylene glycol) or micellar solubilization (ie. Tween 80).

The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed, including synthetic mono- or diglycerides. In addition, fatty acids such as oleic acid find use in the preparation of injectables.

The active ingredient may also be administered by injection as a composition with suitable carriers including saline, dextrose, or water. The daily parenteral dosage regimen will be from about 0.1 to about 30 mg/kg of total body weight, and preferably from about 0.1 to about 10 mg/kg.

For pulmonary administration, the pharmaceutical composition may be administered in the form of an aerosol or with an inhaler including dry powder aerosol.

The pharmaceutical compositions may be subjected to conventional pharmaceutical operations such as sterilization and/or may contain conventional adjuvants, such as preservatives, stabilizers, wetting agents, emulsifiers, buffers etc. Tablets and pills can additionally be prepared with enteric coatings. Such compositions may also comprise adjuvants, such as wetting, sweetening, flavoring, and perfuming agents. Accordingly, in yet another embodiment of the present invention, there is provided a method of manufacturing a medicament, the method comprising combining an amount of a compound according to Formulas I-III with a pharmaceutically acceptable carrier to manufacture the medicament.

In yet another embodiment, the invention provides a method of manufacturing a medicament for the treatment of Alzheimer's disease, the method comprising combining an amount of a compound according to Formulas I-III with a pharmaceutically acceptable carrier to manufacture the medicament.

Combinations

While the compounds of the invention can be dosed or administered as the sole active pharmaceutical agent, they can also be used in combination with one or more compounds of the invention or in conjunction with other agents. When administered as a combination, the therapeutic agents can be formulated as separate compositions that are administered simultaneously or sequentially at different times, or the therapeutic agents can be given as a single composition.

The phrase "co-therapy" (or "combination-therapy"), in defining use of a compound of the present invention and another pharmaceutical agent, is intended to embrace administration of each agent in a sequential manner in a regimen that will provide beneficial effects of the drug combination, and is intended as well to embrace co-administration of these agents in a substantially simultaneous manner, such as in a single capsule having a fixed ratio of these active agents or in multiple, separate capsules for each agent.

Specifically, the administration of compounds of the present invention may be in conjunction with additional therapies known to those skilled in the art in the prevention or treatment of beta-secretase, gamma-secretase and/or other reagents known in influence the formation and/or deposition of amyloid beta, otherwise responsible for the formation of plaque on the brain.

If formulated as a fixed dose, such combination products employ the compounds of this invention within the accepted dosage ranges. Compounds of Formulas I, II and III may also be administered sequentially with other known medicinal agents. The invention is not limited in the sequence of administration; compounds of the invention may be administered either prior to, simultaneous with or after administration of the known anti-inflammatory agent.

The foregoing description is merely illustrative of the invention and is not intended to limit the invention to the disclosed compounds, compositions and methods variations and changes, which are obvious to one skilled in the art, are intended to be within the scope and nature of the invention, as defined in the appended claims. From the foregoing description, one skilled in the art can easily ascertain the essential characteristics of this invention, and without departing from the spirit and scope thereof, can make various changes and modifications of the invention to adapt it to various usages and conditions. All patents and other publications recited herein are hereby incorporated by reference in their entireties.

What is claimed is:
1. A compound of Formula I

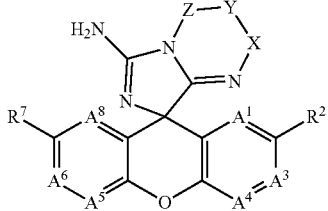

or a stereoisomer, tautomer, or pharmaceutically acceptable salt thereof, wherein $A^1$ is $CR^1$;
$A^3$ is $CR^3$;
$A^4$ is $CR^4$;
$A^5$ is $CR^5$;
$A^6$ is $CR^6$;
$A^8$ is $CR^8$;

each of $R^1$, $R^4$, $R^5$ and $R^8$, independently, is H, F, Cl, Br, $CF_3$, $OCF_3$, $C_{1-6}$-alkyl, CN, OH, —$OC_{1-6}$-alkyl, —$S(O)_oC_{1-6}$-alkyl, —$NHC_{1-6}$-alkyl or —$C(O)C_{1-6}$-alkyl, wherein the $C_{1-6}$-alkyl and $C_{1-6}$-alkyl portion of —$OC_{1-6}$-alkyl, —$S(O)_oC_{1-6}$-alkyl, —$NHC_{1-6}$-alkyl and —$C(O)C_{1-6}$-alkyl are optionally substituted with 1-3 substituents of F, oxo or OH;

$R^2$ is Cl, Br, $C_{1-6}$-alkyl, $C_{2-4}$alkenyl, $C_{2-4}$alkynyl, CN, —$OC_{1-6}$alkyl, —$SC_{1-6}$alkyl, —$NHC_{1-6}$alkyl, —$N(C_{1-3}$alkyl$)_2$, —NH-phenyl, —NH-benzyl, phenyl, pyridyl, pyrimidyl, pyrazinyl, pyridazinyl, pyrazolyl, isoxazolyl, thiazolyl, pyranyl, dihydropyranyl, tetrahydropyranyl, furanyl, dihydrofuranyl, tetrahydrofuranyl, pyrrolyl, pyrrolidinyl, tetrahydropyrrolyl, piperidinyl, piperazinyl, morpholinyl, azetidinyl, 8-oxo-3-aza-bicyclo[3.2.1]oct-3-yl, aza-bicyclo[2.2.1]hept-5-yl, 2-oxo-7-aza-[3,5]-spironon-7-yl, cyclopentyl, cyclohexyl or —$Si(CH_3)_3$, wherein the $C_{1-6}$-alkyl, $C_{2-4}$alkenyl, $C_{2-4}$alkynyl, —$OC_{1-6}$alkyl, —$SC_{1-6}$alkyl, —$NHC_{1-6}$alkyl, —$N(C_{1-3}$alkyl$)_2$, —NH-phenyl, —NH-benzyl, phenyl, pyridyl, pyrimidyl, pyrazinyl, pyridazinyl, pyrazolyl, isoxazolyl, thiazolyl, pyranyl, dihydropyranyl, tetrahydropyranyl, furanyl, dihydrofuranyl, tetrahydrofuranyl, pyrrolidinyl, piperidinyl, piperazinyl, morpholinyl, azetidinyl, 8-oxo-3-aza-bicyclo[3.2.1]oct-3-yl, aza-bicyclo[2.2.1]hept-5-yl, 2-oxo-7-aza-[3,5]-spironon-7-yl, cyclopentyl and cyclohexyl are optionally substituted, independently, with 1-5 substituents of $R^9$;

each of $R^3$ and $R^6$, independently, is H, halo, haloalkyl, haloalkoxyl, $C_{1-6}$-alkyl, CN, OH, $OC_{1-6}$-alkyl, $S(O)_o$ $C_{1-6}$-alkyl, $NHC_{1-6}$-alkyl or $C(O)C_{1-6}$-alkyl;

$R^7$ is $C_{1-6}$-alkyl, $C_{2-4}$alkenyl, $C_{2-4}$alkynyl, CN, —$OC_{1-6}$alkyl, —$SC_{1-6}$alkyl, —$NHC_{1-6}$alkyl, —$N(C_{1-3}$alkyl$)_2$, —$NHC(=O)R^9$, —$C(=O)NHR^9$, —$NHS(O)_2R^9$, —$S(O)_2NHR^9$, —NH-phenyl, —NH-benzyl, phenyl, pyridyl, pyrimidyl, pyrazinyl, pyridazinyl, pyrazolyl, isoxazolyl, thiazolyl, pyranyl, dihydropyranyl, tetrahydropyranyl, furanyl, dihydrofuranyl, tetrahydrofuranyl, pyrrolyl, pyrrolidinyl, tetrahydropyrrolyl, piperidinyl, piperazinyl, morpholinyl, azetidinyl, 8-oxo-3-aza-bicyclo[3.2.1]oct-3-yl, aza-bicyclo[2.2.1]hept-5-yl, 2-oxo-7-aza-[3,5]-spironon-7-yl, cyclopentyl or cyclohexyl, wherein the $C_{1-6}$-alkyl, $C_{2-4}$alkenyl, $C_{2-4}$alkynyl, —$OC_{1-6}$alkyl, —$SC_{1-6}$alkyl, —$NHC_{1-6}$alkyl, —$N(C_{1-3}$alkyl$)_2$, —$NHC(=O)R^9$, —$C(=O)NHR^9$, —$NHS(O)_2R^9$, —$S(O)_2NHR^9$, —NH-phenyl, —NH-benzyl, phenyl, pyridyl, pyrimidyl, pyrazinyl, pyridazinyl, pyrazolyl, isoxazolyl, thiazolyl, pyranyl, dihydropyranyl, tetrahydropyranyl, furanyl, dihydrofuranyl, tetrahydrofuranyl, pyrrolidinyl, piperidinyl, piperazinyl, morpholinyl, azetidinyl, 8-oxo-3-aza-bicyclo[3.2.1]oct-3-yl, aza-bicyclo[2.2.1]hept-5-yl, 2-oxo-7-aza-[3,5]-spironon-7-yl, cyclopentyl and cyclohexyl are optionally substituted, independently, with 1-5 substituents of $R^9$;

each $R^9$, independently, is halo, haloalkyl, CN, OH, $NO_2$, $NH_2$, acetyl, —$C(O)NHCH_3$, oxo, $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, phenyl, pyridyl, pyrimidyl, pyrazinyl, pyridazinyl, pyrazolyl, isoxazolyl, thiazolyl, morpholinyl, pyrazolyl, isoxazolyl, dihydropyranyl, pyrrolyl, pyrrolidinyl, tetrahydropyrrolyl, piperazinyl, oxetanyl or dioxolyl, wherein each of the $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, phenyl, pyridyl, pyrimidyl, pyrazinyl, pyridazinyl, pyrazolyl, isoxazolyl, thiazolyl, morpholinyl, pyrazolyl, isoxazolyl, dihydropyranyl, pyrrolidinyl, oxetanyl or dioxolyl, is optionally substituted independently with 1-5 substituents of F, Cl, CN, $NO_2$, $NH_2$, OH, oxo, methyl, methoxyl, ethyl, ethoxyl, propyl, propoxyl, isopropyl, isopropoxyl, cyclopropyl, cyclopropylmethoxyl, butyl, butoxyl, isobutoxyl, tert-butoxyl, isobutyl, sec-butyl, tert-butyl, $C_{1-3}$alkylamino-, $C_{1-3}$dialkylamino, $C_{1-3}$thioalkoxyl, or oxetanyl; and —X—Y—Z— taken together is —C $R^{10}R^{10}$—C $R^{10}R^{10}$—C $R^{10}R^{10}$; or —Z— is absent and —X—Y— taken together is —C $R^{10}R^{10}$—C $R^{10}R^{10}$, —$CR^{10}$=$CR^{10}$—, —$NR^{11}$—$CHR^{10}$- or —$CHR^{10}$—$NR^{11}$—, wherein each $R^{10}$, independently, is H, F, Cl, Br, $CF_3$, $OCF_3$, $C_{1-6}$-alkyl, CN, OH, —$OC_{1-6}$-alkyl, —$S(O)_oC_{1-6}$-alkyl, —$NHC_{1-6}$-alkyl or —$C(O)C_{1-6}$-alkyl, wherein the $C_{1-6}$-alkyl and $C_{1-6}$-alkyl portion of —$OC_{1-6}$-alkyl, —$S(O)_oC_{1-6}$-alkyl, —$NHC_{1-6}$-alkyl and —$C(O)C_{1-6}$-alkyl are optionally substituted with 1-3 substituents of F, oxo or OH; and each $R^{11}$, independently, is H, $C_{1-6}$-alkyl or CN.

2. The compound of claim 1, or a pharmaceutically acceptable salt thereof, wherein each of $R^1$, $R^4$, $R^5$ and $R^8$, independently, is H, F, Cl, $CF_3$, $OCF_3$, methyl, ethyl, CN, OH, $OCH_3$, $SCH_3$, $NHCH_3$ or $C(O)CH_3$;

one of $R^2$ and $R^7$, independently, is phenyl, pyridyl, pyrimidyl, pyrazinyl, pyridazinyl, pyrazolyl, isoxazolyl, thiazolyl, pyranyl, dihydropyranyl, tetrahydropyranyl, furanyl, dihydrofuranyl, tetrahydrofuranyl, pyrrolyl, pyrrolidinyl, tetrahydropyrrolyl, piperidinyl, piperazinyl, morpholinyl, azetidinyl, 8-oxo-3-aza-bicyclo[3.2.1]oct-3-yl, aza-bicyclo[2.2.1]hept-5-yl, 2-oxo-7-aza-[3,5]-spironon-7-yl, cyclopentyl, cyclohexyl or —$Si(CH_3)_3$, wherein the phenyl, pyridyl, pyrimidyl, pyrazinyl, pyridazinyl, pyrazolyl, isoxazolyl, thiazolyl, pyranyl, dihydropyranyl, tetrahydropyranyl, furanyl, dihydrofuranyl, tetrahydrofuranyl, pyrrolidinyl, piperidinyl, piperazinyl, morpholinyl, azetidinyl, 8-oxo-3-aza-bicyclo[3.2.1]oct-3-yl, aza-bicyclo[2.2.1]hept-5-yl, 2-oxo-7-aza-[3,5]-spironon-7-yl, cyclopentyl and cyclohexyl are optionally substituted, independently, with 1-3 substituents of $R^9$;

the other of $R^2$ and $R^7$, independently, is $C_{1-6}$-alkyl, $C_{2-4}$alkenyl, $C_{2-4}$alkynyl, CN, —$OC_{1-6}$alkyl, —$SC_{1-6}$alkyl, —$NHC_{1-6}$alkyl, —$N(C_{1-3}$alkyl$)_2$, —NHC(=O)$R^9$, —C(=O)NH$R^9$, —NHS(O)$_2R^9$, —S(O)$_2$NH$R^9$, —NH-phenyl or —NH-benzyl, wherein the $C_{1-6}$-alkyl, $C_{2-4}$alkenyl, $C_{2-4}$alkynyl, CN, —$OC_{1-6}$alkyl, —$SC_{1-6}$alkyl, —$NHC_{1-6}$alkyl, —$N(C_{1-3}$alkyl$)_2$, —NHC(=O)$R^9$, —C(=O)NH$R^9$, —NHS(O)$_2R^9$, —S(O)$_2$NH$R^9$, —NH-phenyl and —NH-benzyl are optionally substituted, independently, with 1-3 substituents of $R^9$;

each of $R^3$ and $R^6$, independently, is H, halo, haloalkyl, haloalkoxyl, $C_{1-6}$-alkyl, CN, OH, $OC_{1-6}$-alkyl, $SC_{1-6}$-alkyl, $NHC_{1-6}$-alkyl or $C(O)C_{1-6}$-alkyl; and —X—Y—Z— taken together is —C $R^{10}R^{10}$—C $R^{10}R^{10}$—C $R^{10}R^{10}$; or —Z— is absent and —X—Y— taken together is —C $R^{10}R^{10}$—C $R^{10}R^{10}$, —C$R^{10}$=C$R^{10}$, —N$R^{11}$—CH$R^{10}$- or —CH$R^{10}$—N$R^{11}$—, wherein each $R^{10}$, independently, is H, F, Cl, Br, CF$_3$, OCF$_3$, $C_{1-6}$-alkyl, CN, OH, —$OC_{1-6}$-alkyl, —S(O)$_oC_{1-6}$-alkyl, —$NHC_{1-6}$-alkyl or —C(O)$C_{1-6}$-alkyl, wherein the $C_{1-6}$-alkyl and $C_{1-6}$-alkyl portion of —$OC_{1-6}$-alkyl, —S(O)$_oC_{1-6}$-alkyl, —$NHC_{1-6}$-alkyl and —C(O)$C_{1-6}$-alkyl are optionally substituted with 1-3 substituents of F, oxo or OH; and each $R^{11}$, independently, is H, $C_{1-6}$-alkyl or CN.

3. The compound according to claim 1, or a pharmaceutically acceptable salt thereof, wherein $R^2$ is halo, haloalkyl, haloalkoxyl, $C_{1-6}$-alkyl, $C_{2-4}$alkenyl, $C_{2-4}$alkynyl, or a ring selected from phenyl, pyridyl, pyrimidyl, pyrazinyl, pyridazinyl, pyrazolyl, isoxazolyl, thiazolyl, pyranyl, dihydropyranyl, tetrahydropyranyl, furanyl, dihydrofuranyl, tetrahydrofuranyl, pyrrolyl, pyrrolidinyl, tetrahydropyrrolyl, piperidinyl, piperazinyl, morpholinyl, azetidinyl, 8-oxo-3-aza-bicyclo[3.2.1]oct-3-yl, aza-bicyclo[2.2.1]hept-5-yl, 2-oxo-7-aza-[3,5]-spironon-7-yl, cyclobutyl, cyclopentyl or cyclohexyl, wherein the $C_{1-6}$-alkyl, $C_{2-4}$alkenyl, $C_{2-4}$alkynyl and ring are optionally substituted, independently, with 1-3 substituents of $R^9$;

each of $R^1$, $R^4$, $R^5$ and $R^8$, independently, is H, F, methyl, CN or OH;

each of $R^3$ and $R^6$, independently, is H, F, Cl, CF$_3$, methyl, CN, OH, OCH$_3$, SCH$_3$ or NHCH$_3$; and $R^7$ is a ring selected from phenyl, pyridyl, pyrimidyl, pyridazinyl, pyrazinyl, triazinyl or thiophenyl, said ring optionally substituted, independently, with 1-3 substituents of $R^9$.

4. A compound of claim 1 having a Formula II:

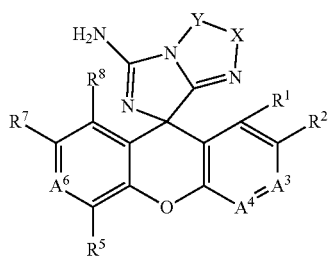

II or a stereoisomer, tautomer, or pharmaceutically acceptable salt thereof, wherein $A^3$ is $CR^3$;
$A^4$ is $CR^4$;
$A^6$ is $CR^6$;

each of $R^1$, $R^4$, $R^5$ and $R^8$, independently, is H, F, Cl, Br, CF$_3$, OCF$_3$, $C_{1-6}$-alkyl, CN, OH, —$OC_{1-6}$-alkyl, —S(O)$_oC_{1-6}$-alkyl, —$NHC_{1-6}$-alkyl or —C(O)$C_{1-6}$-alkyl, wherein the $C_{1-6}$-alkyl and $C_{1-6}$-alkyl portion of —$OC_{1-6}$-alkyl, —S(O)$_oC_{1-6}$-alkyl, —$NHC_{1-6}$-alkyl and —C(O)$C_{1-6}$-alkyl are optionally substituted with 1-3 substituents of F, oxo or OH;

$R^2$ is Cl, Br, $C_{1-6}$-alkyl, $C_{2-4}$alkenyl, $C_{2-4}$alkynyl, CN, —$OC_{1-6}$alkyl, —$SC_{1-6}$alkyl, —$NHC_{1-6}$alkyl, —$N(C_{1-3}$alkyl$)_2$, —NH-phenyl, —NH-benzyl, phenyl, pyridyl, pyrimidyl, pyrazinyl, pyridazinyl, pyrazolyl, isoxazolyl, thiazolyl, pyranyl, dihydropyranyl, tetrahydropyranyl, furanyl, dihydrofuranyl, tetrahydrofuranyl, pyrrolyl, pyrrolidinyl, tetrahydropyrrolyl, piperidinyl, piperazinyl, morpholinyl, azetidinyl, 8-oxo-3-aza-bicyclo[3.2.1]oct-3-yl, aza-bicyclo[2.2.1]hept-5-yl, 2-oxo-7-aza-[3,5]-spironon-7-yl, cyclopentyl, cyclohexyl or —Si(CH$_3$)$_3$, wherein the $C_{1-6}$-alkyl, $C_{2-4}$alkenyl, $C_{2-4}$alkynyl, —$OC_{1-6}$alkyl, —$SC_{1-6}$alkyl, —$NHC_{1-6}$alkyl, —$N(C_{1-3}$alkyl$)_2$, —NH-phenyl, —NH-benzyl, phenyl, pyridyl, pyrimidyl, pyrazinyl, pyridazinyl, pyrazolyl, isoxazolyl, thiazolyl, pyranyl, dihydropyranyl, tetrahydropyranyl, furanyl, dihydrofuranyl, tetrahydrofuranyl, pyrrolidinyl, piperidinyl, piperazinyl, morpholinyl, azetidinyl, 8-oxo-3-aza-bicyclo[3.2.1]oct-3-yl, aza-bicyclo[2.2.1]hept-5-yl, 2-oxo-7-aza-[3,5]-spironon-7-yl, cyclopentyl and cyclohexyl are optionally substituted, independently, with 1-5 substituents of $R^9$;

each of $R^3$ and $R^6$, independently, is H, halo, haloalkyl, haloalkoxyl, $C_{1-6}$-alkyl, CN, OH, $OC_{1-6}$-alkyl, S(O)$_o$ $C_{1-6}$-alkyl, $NHC_{1-6}$-alkyl or $C(O)C_{1-6}$-alkyl;

$R^7$ is $C_{1-6}$-alkyl, $C_{2-4}$alkenyl, $C_{2-4}$alkynyl, CN, —$OC_{1-6}$alkyl, —$SC_{1-6}$alkyl, —$NHC_{1-6}$alkyl, —$N(C_{1-3}$alkyl$)_2$, —NHC(=O)$R^9$, —C(=O)NH$R^9$, —NHS(O)$_2R^9$, —S(O)$_2$NH$R^9$, —NH-phenyl, —NH-benzyl, phenyl, pyridyl, pyrimidyl, pyrazinyl, pyridazinyl, pyrazolyl, isoxazolyl, thiazolyl, pyranyl, dihydropyranyl, tetrahydropyranyl, furanyl, dihydrofuranyl, tetrahydrofuranyl, pyrrolyl, pyrrolidinyl, tetrahydropyrrolyl, piperidinyl, piperazinyl, morpholinyl, azetidinyl, 8-oxo-3-aza-bicyclo[3.2.1]oct-3-yl, aza-bicyclo[2.2.1]hept-5-yl, 2-oxo-7-aza-[3,5]-spironon-7-yl, cyclopentyl or cyclohexyl, wherein the $C_{1-6}$-alkyl, $C_{2-4}$alkenyl, $C_{2-4}$alkynyl, —$OC_{1-6}$alkyl, —$SC_{1-6}$alkyl, —$NHC_{1-6}$alkyl, —$N(C_{1-3}$ alkyl$)_2$, —NHC(=O)$R^9$, —C(=O)NH$R^9$, —NHS(O)$_2R^9$, —S(O)$_2$NH$R^9$, —NH-phenyl, —NH-benzyl, phenyl, pyridyl, pyrimidyl, pyrazinyl, pyridazinyl, pyrazolyl, isoxazolyl, thiazolyl, pyranyl, dihydropyranyl, tetrahydropyranyl, furanyl, dihydrofuranyl, tetrahydrofuranyl, pyrrolidinyl, piperidinyl, piperazinyl, morpholinyl, azetidinyl, 8-oxo-3-aza-bicyclo[3.2.1]oct-3-yl, aza-bicyclo[2.2.1]hept-5-yl, 2-oxo-7-aza-[3,5]-spironon-7-yl, cyclopentyl and cyclohexyl are optionally substituted, independently, with 1-5 substituents of $R^9$;

each $R^9$, independently, is halo, haloalkyl, CN, OH, NO$_2$, NH$_2$, acetyl, —C(O)NHCH$_3$, oxo, $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, phenyl, pyridyl, pyrimidyl, pyrazinyl, pyridazinyl, pyrazolyl, isoxazolyl, thiazolyl, morpholinyl, pyrazolyl, isoxazolyl, dihydropyranyl, pyrrolyl, pyrrolidinyl, tetrahydropyrrolyl, piperazinyl, oxetanyl or dioxolyl, wherein each of the $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, phenyl, pyridyl, pyrimidyl, pyrazinyl, pyridazinyl, pyrazolyl, isoxazolyl, thiazolyl, morpholinyl, pyrazolyl, isoxazolyl, dihydropyranyl, pyrrolidinyl, oxetanyl or dioxolyl, is optionally substituted independently with 1-5 substituents of F, Cl, CN, $NO_2$, $NH_2$, OH, oxo, methyl, methoxyl, ethyl, ethoxyl, propyl, propoxyl, isopropyl, isopropoxyl, cyclopropyl, cyclopropylmethoxyl, butyl, butoxyl, isobutoxyl, tert-butoxyl, isobutyl, sec-butyl, tert-butyl, $C_{1-3}$alkylamino-, $C_{1-3}$dialkylamino, $C_{1-3}$thioalkoxyl, or oxetanyl; and —X—Y— taken together is —$CHR^{10}$—$CHR^{10}$—, —$CR^{10}$=$CR^{10}$—, —$NR^{11}$—$CHR^{10}$— or —$CHR^{10}$—$NR^{11}$—, wherein each $R^{10}$, independently, is H, F, Cl, Br, $CF_3$, $OCF_3$, $C_{1-6}$-alkyl, CN, OH, —$OC_{1-6}$-alkyl, —$S(O)_oC_{1-6}$-alkyl, —$NHC_{1-6}$-alkyl or —$C(O)C_{1-6}$-alkyl, wherein the $C_{1-6}$-alkyl and $C_{1-6}$-alkyl portion of —$OC_{1-6}$-alkyl, —$S(O)_oC_{1-6}$-alkyl, —$NHC_{1-6}$-alkyl and —$C(O)C_{1-6}$-alkyl are optionally substituted with 1-3 substituents of F, oxo or OH; and each $R^{11}$, independently, is H, $C_{1-6}$-alkyl or CN.

5. The compound according to claim 1, or a stereoisomer, tautomer or pharmaceutically acceptable salt thereof, wherein $R^1$ is H or F;
$A^3$ is CH or CF;
$A^4$ is CH or CF;
$R^5$ is H or F;
$A^6$ is CH or CF;
$R^8$ is H or F; and
—X—Y— taken together is —$CR^{10}$=$CR^{10}$—, wherein each $R^{10}$, independently, is H, F, Cl, Br, $CF_3$, $OCF_3$, $C_{1-6}$-alkyl, CN, OH, —$OC_{1-3}$-alkyl, —$S(O)_oC_{1-3}$-alkyl, or —$NHC_{1-3}$-alkyl.

6. The compound according to claim 1, or a stereoisomer or pharmaceutically acceptable salt thereof, wherein each of $R^1$, $R^4$, $R^5$ and $R^8$, independently, is H, F, Cl, $CF_3$, $OCF_3$, methyl, ethyl, CN, OH, $OCH_3$, $SCH_3$, $NHCH_3$ or $C(O)CH_3$;

one of $R^2$ and $R^7$, independently, is phenyl, pyridyl, pyrimidyl, pyrazinyl, pyridazinyl, pyrazolyl, isoxazolyl, thiazolyl, pyranyl, dihydropyranyl, tetrahydropyranyl, furanyl, dihydrofuranyl, tetrahydrofuranyl, pyrrolyl, pyrrolidinyl, tetrahydropyrrolyl, piperidinyl, piperazinyl, morpholinyl, azetidinyl, 8-oxo-3-aza-bicyclo[3.2.1]oct-3-yl, aza-bicyclo[2.2.1]hept-5-yl, 2-oxo-7-aza-[3,5]-spironon-7-yl, cyclopentyl, cyclohexyl or —$Si(CH_3)_3$, wherein the phenyl, pyridyl, pyrimidyl, pyrazinyl, pyridazinyl, pyrazolyl, isoxazolyl, thiazolyl, pyranyl, dihydropyranyl, tetrahydropyranyl, furanyl, dihydrofuranyl, tetrahydrofuranyl, pyrrolidinyl, tetrahydropyrrolyl, piperidinyl, piperazinyl, morpholinyl, azetidinyl, 8-oxo-3-aza-bicyclo[3.2.1]oct-3-yl, aza-bicyclo[2.2.1]hept-5-yl, 2-oxo-7-aza-[3,5]-spironon-7-yl, cyclopentyl and cyclohexyl are optionally substituted, independently, with 1-3 substituents of $R^9$;

the other of $R^2$ and $R^7$, independently, is $C_{1-6}$-alkyl, $C_{2-4}$alkenyl, $C_{2-4}$alkynyl, CN, —$OC_{1-6}$alkyl, —$SC_{1-6}$alkyl, —$NHC_{1-6}$alkyl, —$N(C_{1-3}$alkyl$)_2$, —$NHC(=O)R^9$, —$C(=O)NHR^9$, —$NHS(O)_2R^9$, —$S(O)_2NHR^9$, —NH-phenyl or —NH-benzyl, wherein the $C_{1-6}$-alkyl, $C_{2-4}$alkenyl, $C_{2-4}$alkynyl, CN, —$OC_{1-6}$alkyl, —$SC_{1-6}$alkyl, —$NHC_{1-6}$alkyl, —$N(C_{1-3}$alkyl$)_2$, —$NHC(=O)R^9$, —$C(=O)NHR^9$, —$NHS(O)_2R^9$, —$S(O)_2NHR^9$, —NH-phenyl and —NH-benzyl are optionally substituted, independently, with 1-3 substituents of $R^9$;

each of $R^3$ and $R^6$, independently, is H, halo, haloalkyl, haloalkoxyl, $C_{1-6}$-alkyl, CN, OH, $OC_{1-6}$-alkyl, $SC_{1-6}$-alkyl, $NHC_{1-6}$-alkyl or $C(O)C_{1-6}$-alkyl; and each $R^{10}$, independently, is H, F, Cl, $CF_3$, $OCF_3$, methyl, ethyl, CN, OH, $OCH_3$, $SCH_3$, $NHCH_3$ or $C(O)CH_3$.

7. The compound according to claim 1, or a stereoisomer or pharmaceutically acceptable salt thereof, wherein $R^7$ is a ring selected from phenyl, pyridyl, pyrimidyl, pyrazinyl, pyridazinyl, pyrazolyl, isoxazolyl, thiazolyl, pyranyl, dihydropyranyl, tetrahydropyranyl, furanyl, dihydrofuranyl, tetrahydrofuranyl, pyrrolyl, pyrrolidinyl, tetrahydropyrrolyl, piperidinyl, piperazinyl, morpholinyl, said ring optionally substituted, independently, with 1-3 substituents of $R^9$.

8. The compound according to claim 1, or a stereoisomer or pharmaceutically acceptable salt thereof, wherein $R^2$ is halo, haloalkyl, haloalkoxyl, $C_{1-6}$-alkyl, $C_{2-4}$alkenyl, $C_{2-4}$alkynyl, or a ring selected from phenyl, pyridyl, pyrimidyl, pyrazinyl, pyridazinyl, pyrazolyl, isoxazolyl, thiazolyl, pyranyl, dihydropyranyl, tetrahydropyranyl, furanyl, dihydrofuranyl, tetrahydrofuranyl, pyrrolyl, pyrrolidinyl, tetrahydropyrrolyl, piperidinyl, piperazinyl, morpholinyl, azetidinyl, 8-oxo-3-aza-bicyclo[3.2.1]oct-3-yl, aza-bicyclo[2.2.1]hept-5-yl, 2-oxo-7-aza-[3,5]-spironon-7-yl, cyclobutyl, cyclopentyl or cyclohexyl, wherein the $C_{1-6}$-alkyl, $C_{2-4}$alkenyl, $C_{2-4}$alkynyl and ring are optionally substituted, independently, with 1-3 substituents of $R^9$;

each of $R^1$, $R^4$, $R^5$ and $R^8$, independently, is H, F, methyl, CN or OH;

each of $R^3$ and $R^6$, independently, is H, F, Cl, $CF_3$, methyl, CN, OH, $OCH_3$, $SCH_3$ or $NHCH_3$;

$R^7$ is a ring selected from phenyl, pyridyl, pyrimidyl, pyridazinyl, pyrazinyl, triazinyl or thiophenyl, said ring optionally substituted, independently, with 1-3 substituents of $R^9$; and each $R^{10}$, independently, is H, F, Cl, $CF_3$, $OCF_3$, methyl, ethyl, CN, OH, $OCH_3$, $SCH_3$, $NHCH_3$ or $C(O)CH_3$.

9. The compound according to claim 1, or a stereoisomer or pharmaceutically acceptable salt thereof, wherein $A^3$ is $CR^3$;
$A^4$ is $CR^4$;
$R^2$ is halo, haloalkyl, haloalkoxyl, $C_{1-6}$-alkyl, $C_{2-4}$alkenyl, $C_{2-4}$alkynyl, or a ring selected from phenyl, pyridyl, pyrimidyl, pyrazinyl, pyridazinyl, pyrazolyl, isoxazolyl, thiazolyl, pyranyl, dihydropyranyl, tetrahydropyranyl, furanyl, dihydrofuranyl, tetrahydrofuranyl, pyrrolyl, pyrrolidinyl, tetrahydropyrrolyl, piperidinyl, piperazinyl, morpholinyl, azetidinyl, 8-oxo-3-aza-bicyclo[3.2.1]oct-3-yl, aza-bicyclo[2.2.1]hept-5-yl, 2-oxo-7-aza-[3,5]-spironon-7-yl, cyclobutyl, cyclopentyl or cyclohexyl, wherein the $C_{1-6}$-alkyl, $C_{2-4}$alkenyl, $C_{2-4}$alkynyl and ring are optionally substituted, independently, with 1-3 substituents of $R^9$;

each of $R^1$, $R^4$, $R^5$ and $R^8$, independently, is H, F, methyl, CN or OH;

each of $R^3$ and $R^6$, independently, is H, F, Cl, $CF_3$, methyl, CN, OH, $OCH_3$, $SCH_3$ or $NHCH_3$;

$R^7$ is a ring selected from phenyl, pyridyl, pyrimidyl, pyridazinyl, pyrazinyl, triazinyl or thiophenyl, said ring optionally substituted, independently, with 1-3 substituents of $R^9$; and each $R^{10}$, independently, is H, F, Cl, $CF_3$, $OCF_3$, methyl, ethyl, CN, OH, $OCH_3$, $SCH_3$, $NHCH_3$ or $C(O)CH_3$.

10. The compound of claim 1, or a stereoisomer or pharmaceutically acceptable salt thereof, selected from
- 4'-fluoro-7'-(2-fluoro-3-pyridinyl)-2'-methoxyspiro[imidazo[1,5-a]imidazole-7,9'-xanthen]-5-amine;
- (7S)-4'-fluoro-7'-(2-fluoro-3-pyridinyl)-2'-(2-fluoro-4-pyridinyl)spiro[imidazo[1,5-a]imidazole-7,9'-xanthen]-5-amine;
- (7R)-4'-fluoro-7'-(2-fluoro-3-pyridinyl)-2'-(2-fluoro-4-pyridinyl)spiro[imidazo[1,5-a]imidazole-7,9'-xanthen]-5-amine;
- (7R)-2'-(5,6-dihydro-2H-pyran-3-yl)-4'-fluoro-7'-(2-fluoro-3-pyridinyl)spiro[imidazo[1,5-a]imidazole-7,9'-xanthen]-5-amine;
- (7S)-2'-(5,6-dihydro-2H-pyran-3-yl)-4'-fluoro-7'-(2-fluoro-3-pyridinyl)spiro[imidazo[1,5-a]imidazole-7,9'-xanthen]-5-amine;
- (7R)-4'-fluoro-7'-(2-fluoro-3-pyridinyl)-2'-(4-methylphenyl)spiro[imidazo[1,5-a]imidazole-7,9'-xanthen]-5-amine;
- (7S)-4'-fluoro-7'-(2-fluoro-3-pyridinyl)-2'-(4-methylphenyl)spiro[imidazo[1,5-a]imidazole-7,9'-xanthen]-5-amine;
- (7R)-4'-fluoro-7'-(2-fluoro-3-pyridinyl)-2'-(4-morpholinyl)spiro[imidazo[1,5-a]imidazole-7,9'-xanthen]-5-amine;
- (7S)-4'-fluoro-7'-(2-fluoro-3-pyridinyl)-2'-(4-morpholinyl)spiro[imidazo[1,5-a]imidazole-7,9'-xanthen]-5-amine;
- (7R)-2'-(3,6-dihydro-2H-pyran-4-yl)-4'-fluoro-7'-(2-fluoro-3-pyridinyl)spiro[imidazo[1,5-a]imidazole-7,9'-xanthen]-5-amine;
- (7S)-2'-(3,6-dihydro-2H-pyran-4-yl)-4'-fluoro-7'-(2-fluoro-3-pyridinyl)spiro[imidazo[1,5-a]imidazole-7,9'-xanthen]-5-amine;
- (7R)-2'-(4,4-difluoro-1-piperidinyl)-4'-fluoro-7'-(2-fluoro-3-pyridinyl)spiro[imidazo[1,5-a]imidazole-7,9'-xanthen]-5-amine; and
- (7S)-2'-(4,4-difluoro-1-piperidinyl)-4'-fluoro-7'-(2-fluoro-3-pyridinyl)spiro[imidazo[1,5-a]imidazole-7,9'-xanthen]-5-amine;
- (7S)-4'-fluoro-7'-(2-fluoropyridin-3-yl)-2'-methoxy-3,4-dihydro-2H-spiro[imidazo[1,5-a]pyrimidine-8,9'-xanthen]-6-amine; and
- (7R)-4'-fluoro-7'-(2-fluoropyridin-3-yl)-2'-methoxy-3,4-dihydro-2H-spiro[imidazo[1,5-a]pyrimidine-8,9'-xanthen]-6-amine.

11. A pharmaceutical composition comprising a compound according to claim 1 and a pharmaceutically acceptable excipient.

12. A process for preparing a compound of claim 1, the process comprising the step of reacting a compound 20

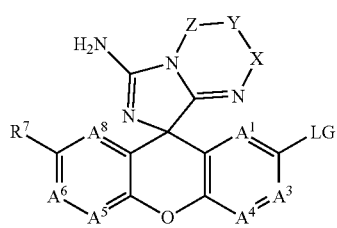

wherein $A^1$, $A^3$, $A^4$, $A^5$, $A^6$, $A^8$, $R^7$, X, Y and Z of compound 20 are as defined in claim 1 and LG is a leaving group selected from Br, Cl or —O—S(=O)$_2$CF$_3$, with a compound having the structure

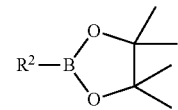

or $R^2$—B(OH)$_2$, wherein $R^7$ is as defined in claim 1 to prepare the compound of claim 1.

* * * * *